United States Patent
To

(10) Patent No.: US 12,220,140 B1
(45) Date of Patent: Feb. 11, 2025

(54) THROMBECTOMY DEVICES WITH LATERAL AND VERTICAL BIAS

(71) Applicant: AVANTEC VASCULAR CORPORATION, Sunnyvale, CA (US)

(72) Inventor: John To, Sunnyvale, CA (US)

(73) Assignee: AVANTEC VASCULAR CORPORATION, Sunnyvale, CA (US)

( * ) Notice: Subject to any disclaimer, the term of this patent is extended or adjusted under 35 U.S.C. 154(b) by 0 days.

(21) Appl. No.: 18/807,575

(22) Filed: Aug. 16, 2024

Related U.S. Application Data

(60) Provisional application No. 63/520,029, filed on Aug. 16, 2023.

(51) Int. Cl.
*A61B 17/22* (2006.01)
*A61B 17/00* (2006.01)
*A61B 17/3205* (2006.01)

(52) U.S. Cl.
CPC ........ *A61B 17/22* (2013.01); *A61B 17/00234* (2013.01); *A61B 17/3205* (2013.01); *A61B 2017/00238* (2013.01); *A61B 2017/00292* (2013.01); *A61B 2017/00398* (2013.01); *A61B 2017/00477* (2013.01); *A61B 2017/22038* (2013.01); *A61B 2017/22079* (2013.01); *A61B 2217/005* (2013.01)

(58) Field of Classification Search
CPC ................ A61B 17/22; A61B 17/3205; A61B 2017/00292; A61B 2017/00477
See application file for complete search history.

(56) References Cited

U.S. PATENT DOCUMENTS

| | | |
|---|---|---|
| 3,358,472 A | 12/1967 | Klipping et al. |
| 4,167,944 A | 9/1979 | Banko |
| 4,306,570 A | 12/1981 | Matthews |
| 4,445,509 A | 5/1984 | Auth |
| 4,598,710 A | 7/1986 | Kleinberg et al. |
| 4,598,716 A | 7/1986 | Hileman |
| 4,631,052 A | 12/1986 | Kensey |
| 4,669,469 A | 6/1987 | Gifford, III et al. |
| 4,690,140 A | 9/1987 | Mecca |
| 4,696,667 A | 9/1987 | Masch |
| 4,732,154 A | 3/1988 | Shiber |

(Continued)

FOREIGN PATENT DOCUMENTS

| | | |
|---|---|---|
| DE | 20304580 | 9/2004 |
| EP | 0254414 | 8/1992 |

(Continued)

OTHER PUBLICATIONS

U.S. Appl. No. 18/805,071, filed Mar. 11, 2022, To, et al.—owned by Applicant.

(Continued)

*Primary Examiner* — Ryan J. Severson
(74) *Attorney, Agent, or Firm* — Brian S. Boyer; SYNDICATED LAW, PC

(57) ABSTRACT

Thrombectomy systems having curved tubular cutting devices, and methods of using them, are provided. These systems, devices, and methods can (i) effectively cut and remove a variety of thrombus tissue from blood vessels, including soft, tough, and hard tissue; (ii) safely self-collect and remove tissue particles to avoid release of emboli; and, (iii) effectively treat a blood vessel with a reduced risk of suffering vessel injuries that can lead to increased stenosis.

20 Claims, 18 Drawing Sheets

(56) References Cited

U.S. PATENT DOCUMENTS

| | | |
|---|---|---|
| 4,770,652 A | 9/1988 | Mahurkar |
| 4,781,186 A | 11/1988 | Simpson et al. |
| 4,790,812 A | 12/1988 | Hawkins et al. |
| 4,804,364 A | 2/1989 | Dieras et al. |
| 4,808,153 A | 2/1989 | Parisi |
| 4,844,064 A | 7/1989 | Thimsen |
| 4,857,045 A | 8/1989 | Rydell |
| 4,857,046 A | 8/1989 | Stevens et al. |
| 4,867,157 A | 9/1989 | Gurk-Burleson |
| 4,886,490 A | 12/1989 | Shiber |
| 4,887,599 A | 12/1989 | Muller |
| 4,894,051 A | 1/1990 | Shiber |
| 4,911,148 A | 3/1990 | Sosnowski |
| 4,950,277 A | 8/1990 | Farr |
| 4,994,067 A | 2/1991 | Summers |
| 4,994,087 A | 2/1991 | Konrad et al. |
| 5,041,082 A | 8/1991 | Shiber |
| 5,047,040 A | 9/1991 | Simpson et al. |
| 5,074,841 A | 12/1991 | Ademovic |
| 5,100,426 A | 3/1992 | Nixon |
| 5,114,399 A | 5/1992 | Kovalcheck |
| 5,122,134 A | 6/1992 | Borzone et al. |
| 5,231,989 A | 8/1993 | Middleman et al. |
| 5,242,461 A | 9/1993 | Kortenbach et al. |
| 5,267,955 A | 12/1993 | Hanson |
| 5,282,813 A | 2/1994 | Redha |
| 5,282,821 A | 2/1994 | Donahue |
| 5,284,128 A | 2/1994 | Hart |
| 5,304,189 A | 4/1994 | Goldberg et al. |
| 5,312,427 A | 5/1994 | Shturman |
| 5,314,438 A | 5/1994 | Shturman |
| 5,320,635 A | 6/1994 | Smith |
| 5,332,329 A | 7/1994 | Hill et al. |
| 5,334,211 A | 8/1994 | Shiber |
| 5,356,418 A | 10/1994 | Shturman |
| 5,358,472 A | 10/1994 | Vance et al. |
| 5,360,432 A | 11/1994 | Shturman |
| 5,370,609 A | 12/1994 | Drasler et al. |
| 5,372,587 A | 12/1994 | Hammerslag et al. |
| 5,409,454 A | 4/1995 | Fischell et al. |
| 5,417,703 A | 5/1995 | Brown et al. |
| 5,423,799 A | 6/1995 | Shiu |
| 5,429,604 A | 7/1995 | Hammersmark et al. |
| 5,429,617 A | 7/1995 | Hammersmark et al. |
| 5,431,173 A | 7/1995 | Chin et al. |
| 5,456,680 A | 10/1995 | Taylor et al. |
| 5,474,532 A | 12/1995 | Steppe |
| 5,489,291 A | 2/1996 | Wiley |
| 5,501,653 A | 3/1996 | Chin |
| 5,520,609 A | 5/1996 | Moll et al. |
| 5,529,580 A | 6/1996 | Kusunoki et al. |
| 5,540,706 A | 7/1996 | Aust |
| 5,554,163 A | 9/1996 | Shturman |
| 5,556,408 A | 9/1996 | Farhat |
| 5,569,197 A | 10/1996 | Helmus |
| 5,569,275 A | 10/1996 | Kotula |
| 5,584,843 A | 12/1996 | Wulfman |
| 5,618,294 A | 4/1997 | Aust |
| 5,626,562 A | 5/1997 | Castro |
| 5,632,755 A | 5/1997 | Nordgren |
| 5,634,178 A | 5/1997 | Sugiura |
| 5,634,883 A | 6/1997 | Moll |
| 5,643,178 A | 7/1997 | Moll |
| 5,643,251 A | 7/1997 | Hillsman |
| 5,643,297 A | 7/1997 | Nordgren |
| 5,643,298 A | 7/1997 | Nordgren |
| 5,649,941 A | 7/1997 | Lary |
| 5,656,562 A | 8/1997 | Wu |
| 5,665,062 A | 9/1997 | Houser |
| 5,665,098 A | 9/1997 | Kelly |
| 5,669,926 A | 9/1997 | Aust |
| 5,690,634 A | 11/1997 | Muller |
| 5,690,643 A | 11/1997 | Wijay |
| 5,695,506 A | 12/1997 | Pike |
| 5,716,327 A | 2/1998 | Warner |
| 5,725,543 A | 3/1998 | Redha |
| 5,728,129 A | 3/1998 | Summers |
| 5,733,297 A | 3/1998 | Wang |
| 5,743,456 A | 4/1998 | Jones |
| 5,746,758 A | 5/1998 | Nordgren |
| 5,749,885 A | 5/1998 | Sjostrom |
| 5,755,731 A | 5/1998 | Grinberg |
| 5,766,196 A | 6/1998 | Griffiths |
| 5,772,329 A | 6/1998 | Bardon |
| 5,779,721 A | 7/1998 | Nash |
| 5,782,834 A | 7/1998 | Lucey |
| 5,820,592 A | 10/1998 | Hammerslag |
| 5,826,582 A | 10/1998 | Sheehan |
| 5,828,582 A | 10/1998 | Conklen |
| 5,843,103 A | 12/1998 | Wulfman |
| 5,851,208 A | 12/1998 | Trott |
| 5,851,212 A | 12/1998 | Zirps |
| 5,865,082 A | 2/1999 | Cote |
| 5,865,098 A | 2/1999 | Anelli |
| 5,873,882 A | 2/1999 | Straub |
| 5,876,414 A | 3/1999 | Straub |
| 5,882,329 A | 3/1999 | Patterson |
| 5,882,333 A | 3/1999 | Schaer |
| 5,885,098 A | 3/1999 | Witkowski |
| 5,890,643 A | 4/1999 | Razon |
| 5,895,399 A | 4/1999 | Barbut |
| 5,895,508 A | 4/1999 | Halow |
| 5,897,566 A | 4/1999 | Shturman |
| 5,902,263 A | 5/1999 | Patterson |
| 5,902,283 A | 5/1999 | Darouiche |
| 5,902,313 A | 5/1999 | Redha |
| 5,910,150 A | 6/1999 | Saadat |
| 5,941,869 A | 8/1999 | Patterson |
| 5,941,893 A | 8/1999 | Saadat |
| 6,001,112 A | 12/1999 | Taylor |
| 6,015,420 A | 1/2000 | Wulfman |
| 6,027,450 A | 2/2000 | Brown |
| 6,027,514 A | 2/2000 | Stine |
| 6,042,593 A | 3/2000 | Storz |
| 6,048,339 A | 4/2000 | Zirps |
| 6,053,923 A | 4/2000 | Veca |
| 6,066,153 A | 5/2000 | Lev |
| 6,080,170 A | 6/2000 | Nash |
| 6,086,153 A | 7/2000 | Heidmann |
| 6,090,118 A | 7/2000 | McGuckin |
| 6,113,615 A | 9/2000 | Wulfman |
| 6,132,444 A | 10/2000 | Shturman |
| 6,139,557 A | 10/2000 | Passafaro |
| 6,142,955 A | 11/2000 | Farascioni |
| 6,146,395 A | 11/2000 | Kanz |
| 6,152,938 A | 11/2000 | Curry |
| 6,156,046 A | 12/2000 | Passafaro |
| 6,165,209 A | 12/2000 | Patterson |
| 6,183,487 B1 | 2/2001 | Barry |
| 6,206,898 B1 | 3/2001 | Honeycutt |
| 6,237,405 B1 | 5/2001 | Leslie |
| 6,238,405 B1 | 5/2001 | Findlay |
| 6,241,744 B1 | 6/2001 | Imran |
| 6,258,098 B1 | 7/2001 | Taylor |
| 6,258,109 B1 | 7/2001 | Barry |
| 6,264,630 B1 | 7/2001 | Mickley |
| 6,284,830 B1 | 9/2001 | Gottschalk |
| 6,299,622 B1 | 10/2001 | Snow |
| 6,319,242 B1 | 11/2001 | Patterson |
| 6,325,067 B1 | 12/2001 | Sterman et al. |
| 6,355,027 B1 | 3/2002 | Le |
| 6,371,928 B1 | 4/2002 | Mcfann |
| 6,406,422 B1 | 6/2002 | Landesberg |
| 6,406,442 B1 | 6/2002 | McFann |
| 6,451,036 B1 | 6/2002 | Heitzmann |
| 6,454,779 B1 | 9/2002 | Taylor |
| 6,482,215 B1 | 11/2002 | Shiber |
| 6,482,217 B1 | 11/2002 | Pintor |
| 6,494,890 B1 | 12/2002 | Shturman |
| 6,497,711 B1 | 12/2002 | Plaia |
| 6,554,846 B2 | 4/2003 | Hamilton |
| 6,554,848 B2 | 4/2003 | Boylan |
| 6,562,049 B1 | 5/2003 | Norlander |
| 6,565,195 B2 | 5/2003 | Blair |

(56) References Cited

U.S. PATENT DOCUMENTS

| | | |
|---|---|---|
| 6,565,588 B1 | 5/2003 | Clement |
| 6,572,630 B1 | 6/2003 | McGucin |
| 6,578,851 B1 | 6/2003 | Bryant |
| 6,579,298 B1 | 6/2003 | Johnson |
| 6,579,299 B2 | 6/2003 | McGuckin |
| 6,596,005 B1 | 7/2003 | Kanz |
| 6,602,264 B1 | 8/2003 | McGuckin |
| 6,610,077 B1 | 8/2003 | Hancock et al. |
| 6,620,148 B1 | 9/2003 | Tsugita |
| 6,623,495 B2 | 9/2003 | Findlay |
| 6,629,953 B1 | 10/2003 | Boyd |
| 6,638,233 B2 | 10/2003 | Corvi |
| 6,638,288 B1 | 10/2003 | Shturman |
| RE38,335 E | 11/2003 | Aust |
| 6,652,548 B2 | 11/2003 | Evans et al. |
| 6,656,195 B2 | 12/2003 | Peters |
| 6,658,195 B1 | 12/2003 | Senshu |
| 6,666,854 B1 | 12/2003 | Lange |
| 6,666,874 B2 | 12/2003 | Heitzmann |
| 6,682,545 B1 | 1/2004 | Kester |
| 6,702,830 B1 | 3/2004 | Demarais |
| 6,746,422 B1 | 6/2004 | Noriega |
| 6,758,851 B2 | 7/2004 | Shiber |
| 6,790,215 B2 | 9/2004 | Findlay |
| 6,800,085 B2 | 10/2004 | Selmon |
| 6,802,284 B2 | 10/2004 | Hironaka |
| 6,808,531 B2 | 10/2004 | Lafontaine |
| 6,818,001 B2 | 11/2004 | Wulfman et al. |
| 6,818,002 B2 | 11/2004 | Shiber |
| 6,830,577 B2 | 12/2004 | Nash |
| 6,843,797 B2 | 1/2005 | Nash |
| 6,860,235 B2 | 3/2005 | Anderson |
| 6,866,854 B1 | 3/2005 | Chang |
| 6,868,854 B2 | 3/2005 | Kempe |
| 6,876,414 B2 | 4/2005 | Hara |
| 6,899,704 B2 | 5/2005 | Sterman et al. |
| 6,936,056 B2 | 8/2005 | Nash |
| 6,991,409 B2 | 1/2006 | Noland et al. |
| 6,997,934 B2 | 2/2006 | Snow |
| 7,008,375 B2 | 3/2006 | Weisel |
| 7,025,751 B2 | 4/2006 | Silva |
| 7,033,357 B2 | 4/2006 | Baxter |
| 7,037,316 B2 | 5/2006 | McGuckin |
| RE39,152 E | 6/2006 | Aust |
| 7,122,017 B2 | 10/2006 | Moutafis et al. |
| 7,169,161 B2 | 1/2007 | Bonnette et al. |
| 7,172,610 B2 | 2/2007 | Heitzmann |
| 7,172,810 B2 | 2/2007 | Hashimoto |
| 7,179,269 B2 | 2/2007 | Welch et al. |
| 7,235,088 B2 | 6/2007 | Pintor |
| 7,316,697 B2 | 1/2008 | Shiber |
| 7,344,546 B2 | 3/2008 | Wulfman |
| 7,344,548 B2 | 3/2008 | Toyota |
| 7,381,198 B2 | 6/2008 | Noriega |
| 7,399,307 B2 | 7/2008 | Evans |
| 7,479,147 B2 | 1/2009 | Honeycutt |
| 7,501,114 B2 | 3/2009 | Sehgal et al. |
| 7,534,249 B2 | 5/2009 | Nash |
| 7,645,290 B2 | 1/2010 | Lucas |
| 7,655,016 B2 | 2/2010 | Demarais et al. |
| 7,666,161 B2 | 2/2010 | Nash |
| 7,670,597 B2 | 3/2010 | Sehgal et al. |
| 7,734,332 B2 | 6/2010 | Sher |
| 7,771,445 B2 | 8/2010 | Heitzmann |
| 7,875,018 B2 | 1/2011 | Tockman |
| 7,879,022 B2 | 2/2011 | Bonnette |
| 7,892,230 B2 | 2/2011 | Woloszko |
| 7,955,345 B2 | 6/2011 | Kucharczyk et al. |
| 7,981,128 B2 | 7/2011 | To |
| 8,007,500 B2 | 8/2011 | Lin |
| 8,007,506 B2 | 8/2011 | To |
| 8,015,420 B2 | 9/2011 | Cherian |
| 8,052,704 B2 | 11/2011 | Olson |
| 8,057,395 B2 | 11/2011 | Lenker et al. |
| 8,057,497 B1 | 11/2011 | Raju et al. |
| 8,070,762 B2 | 12/2011 | Escudero et al. |
| 8,070,791 B2 | 12/2011 | Ferrera et al. |
| 8,197,493 B2 | 6/2012 | Ferrera et al. |
| 8,226,679 B2 | 7/2012 | Johnson et al. |
| 8,236,016 B2 | 8/2012 | To et al. |
| 8,252,010 B1 | 8/2012 | Raju et al. |
| 8,298,244 B2 | 10/2012 | Garcia et al. |
| 8,337,516 B2 | 12/2012 | Escudero |
| 8,361,094 B2 | 1/2013 | To et al. |
| 8,469,979 B2 | 6/2013 | Olson |
| 8,475,483 B2 | 7/2013 | Schmitz et al. |
| 8,517,994 B2 | 8/2013 | Li |
| 8,535,662 B2 | 9/2013 | Chen et al. |
| 8,545,447 B2 | 10/2013 | Demarais |
| 8,568,432 B2 | 10/2013 | Straub |
| 8,572,630 B2 | 10/2013 | Woundy |
| 8,574,262 B2 | 11/2013 | Ferrera et al. |
| 8,579,926 B2 | 11/2013 | Pintor |
| 8,585,726 B2 | 11/2013 | Yoon |
| 8,613,721 B2 | 12/2013 | Wulfman et al. |
| 8,622,992 B2 | 1/2014 | Baxter et al. |
| 8,628,549 B2 | 1/2014 | To et al. |
| 8,628,790 B2 | 1/2014 | To et al. |
| 8,632,560 B2 | 1/2014 | Pal et al. |
| 8,647,355 B2 | 2/2014 | Escudero |
| 8,715,150 B2 | 4/2014 | Creighton |
| 8,721,676 B1 | 5/2014 | Janardhan et al. |
| 8,747,350 B2 | 6/2014 | Chin |
| 8,777,976 B2 | 7/2014 | Brady et al. |
| 8,783,151 B1 | 7/2014 | Janardhan et al. |
| 8,784,434 B2 | 7/2014 | Rosenbluth et al. |
| 8,795,278 B2 | 8/2014 | Schmitz et al. |
| 8,795,306 B2 | 8/2014 | Smith et al. |
| 8,803,030 B1 | 8/2014 | Janardhan et al. |
| 8,845,675 B2 | 9/2014 | Johnson et al. |
| 8,845,678 B1 | 9/2014 | Janardhan et al. |
| 8,852,205 B2 | 10/2014 | Brady et al. |
| 8,852,227 B1 | 10/2014 | Janardhan et al. |
| 8,859,934 B1 | 10/2014 | Janardhan et al. |
| 8,866,049 B1 | 10/2014 | Janardhan et al. |
| 8,872,068 B1 | 10/2014 | Janardhan et al. |
| 8,876,414 B2 | 11/2014 | Taniguchi |
| 8,881,849 B2 | 11/2014 | Shen et al. |
| 8,888,801 B2 | 11/2014 | To et al. |
| 8,895,891 B2 | 11/2014 | Janardhan et al. |
| 8,926,491 B2 | 1/2015 | Creighton |
| 8,926,680 B2 | 1/2015 | Ferrera et al. |
| 8,932,208 B2 | 1/2015 | Kendale et al. |
| 8,932,321 B1 | 1/2015 | Janardhan et al. |
| 8,951,201 B2 | 2/2015 | Mesallum |
| 8,979,793 B2 | 3/2015 | Hofmann |
| 9,005,649 B2 | 4/2015 | Ho et al. |
| 9,050,127 B2 | 6/2015 | Bonnette et al. |
| 9,095,371 B2 | 8/2015 | Escudero et al. |
| 9,107,590 B2 | 8/2015 | Hansmann et al. |
| 9,179,931 B2 | 11/2015 | Janardhan et al. |
| 9,179,995 B2 | 11/2015 | Janardhan et al. |
| 9,198,679 B2 | 12/2015 | To et al. |
| 9,198,687 B2 | 12/2015 | Fulkerson et al. |
| 9,204,893 B2 | 12/2015 | Rizk et al. |
| 9,220,522 B2 | 12/2015 | Fulkerson et al. |
| 9,220,530 B2 | 12/2015 | Moberg |
| 9,238,122 B2 | 1/2016 | Malhi et al. |
| 9,254,144 B2 | 2/2016 | Nguyen et al. |
| 9,308,016 B2 | 4/2016 | Escudero et al. |
| 9,314,263 B2 | 4/2016 | Escudero et al. |
| 9,345,511 B2 | 5/2016 | Smith |
| 9,393,035 B2 | 7/2016 | Yu |
| 9,445,828 B2 | 9/2016 | Turjman et al. |
| 9,492,192 B2 | 11/2016 | To et al. |
| 9,492,193 B2 | 11/2016 | To et al. |
| 9,498,247 B2 | 11/2016 | Patel et al. |
| 9,498,600 B2 | 11/2016 | Rosenthal et al. |
| 9,526,863 B2 | 12/2016 | Baxter et al. |
| 9,526,865 B2 | 12/2016 | Quick et al. |
| 9,604,291 B2 | 3/2017 | Kountanya et al. |
| 9,656,008 B2 | 5/2017 | Wulfman et al. |
| 9,668,767 B2 | 6/2017 | To et al. |
| 9,675,376 B2 | 6/2017 | To et al. |

(56) References Cited

U.S. PATENT DOCUMENTS

| | | |
|---|---|---|
| 9,700,332 B2 | 7/2017 | Marchand et al. |
| 9,717,520 B2 | 8/2017 | Zeroni et al. |
| 9,737,318 B2 | 8/2017 | Monstadt et al. |
| 9,770,258 B2 | 9/2017 | Smith et al. |
| 9,808,277 B2 | 11/2017 | Nash et al. |
| 9,855,071 B2 | 1/2018 | Shaltis |
| 9,883,873 B2 | 2/2018 | Kulas et al. |
| 9,931,166 B2 | 4/2018 | Sauro et al. |
| 9,968,371 B2 | 5/2018 | Todd et al. |
| 9,976,356 B2 | 5/2018 | Burhan et al. |
| 9,993,325 B2 | 5/2018 | Ren et al. |
| 10,004,531 B2 | 6/2018 | Rosenbluth et al. |
| 10,016,211 B2 | 7/2018 | Ferrera et al. |
| 10,022,145 B2 | 7/2018 | Simpson et al. |
| 10,028,759 B2 | 7/2018 | Wallace et al. |
| 10,028,767 B2 | 7/2018 | Germain et al. |
| 10,045,790 B2 | 8/2018 | Cox et al. |
| 10,098,651 B2 | 10/2018 | Marchand et al. |
| 10,154,853 B2 | 12/2018 | To et al. |
| 10,154,854 B2 | 12/2018 | To et al. |
| 10,172,638 B2 | 1/2019 | Palme et al. |
| 10,226,275 B2 | 3/2019 | Escudero et al. |
| 10,226,277 B2 | 3/2019 | Smith et al. |
| 10,238,406 B2 | 3/2019 | Cox et al. |
| 10,251,667 B2 | 4/2019 | Cohen et al. |
| 10,258,358 B2 | 4/2019 | Ulm, III |
| 10,258,409 B2 | 4/2019 | Ben-Oren et al. |
| 10,278,719 B2 | 5/2019 | Ulm, III |
| 10,292,677 B2 | 5/2019 | Johnson et al. |
| 10,292,722 B2 | 5/2019 | Brady et al. |
| 10,292,803 B2 | 5/2019 | Monstadt et al. |
| 10,299,811 B2 | 5/2019 | Brady et al. |
| 10,307,175 B2 | 6/2019 | McGuckin et al. |
| 10,321,925 B2 | 6/2019 | Ulm, III |
| 10,335,260 B2 | 7/2019 | Janardhan et al. |
| 10,342,655 B2 | 7/2019 | Janardhan et al. |
| 10,349,974 B2 | 7/2019 | Patel et al. |
| 10,357,275 B2 | 7/2019 | Majercak et al. |
| 10,376,275 B2 | 8/2019 | Nguyen et al. |
| 10,376,678 B2 | 8/2019 | Levine |
| 10,383,751 B2 | 8/2019 | Ferrera et al. |
| 10,413,310 B2 | 9/2019 | Ferrera et al. |
| 10,420,572 B2 | 9/2019 | Ulm, III |
| 10,426,512 B2 | 10/2019 | Avneri et al. |
| 10,441,311 B2 | 10/2019 | Smith et al. |
| 10,449,269 B2 | 10/2019 | Fahmy et al. |
| 10,456,236 B2 | 10/2019 | Nguyen et al. |
| 10,463,389 B2 | 11/2019 | McGuckin et al. |
| 10,470,797 B1 | 11/2019 | Rai et al. |
| 10,492,822 B2 | 12/2019 | Chen et al. |
| 10,507,036 B2 | 12/2019 | Schuman et al. |
| 10,512,479 B2 | 12/2019 | Nguyen et al. |
| 10,524,824 B2 | 1/2020 | Rottenberg et al. |
| 10,531,883 B1 | 1/2020 | Deville et al. |
| 10,555,752 B2 | 2/2020 | Robertson et al. |
| 10,555,753 B2 | 2/2020 | Moberg et al. |
| 10,568,655 B2 | 2/2020 | Simpson et al. |
| 10,569,049 B2 | 2/2020 | Garrison et al. |
| 10,588,649 B2 | 3/2020 | Brady et al. |
| 10,588,656 B2 | 3/2020 | Trosper et al. |
| 10,595,818 B2 | 3/2020 | Levine |
| 10,603,467 B2 | 3/2020 | Alvarez et al. |
| 10,624,659 B2 | 4/2020 | Gamba et al. |
| 10,646,247 B2 | 5/2020 | Wilson et al. |
| 10,667,833 B2 | 6/2020 | Vale et al. |
| 10,682,152 B2 | 6/2020 | Vale et al. |
| 10,702,367 B2 | 7/2020 | Sachar et al. |
| 10,722,253 B2 | 7/2020 | Deville et al. |
| 10,743,894 B2 | 8/2020 | Brady et al. |
| 10,743,895 B2 | 8/2020 | Losordo et al. |
| 10,751,159 B2 | 8/2020 | Janardhan et al. |
| 10,765,446 B2 | 9/2020 | Higgins et al. |
| 10,774,596 B2 | 9/2020 | Zhang et al. |
| 10,779,843 B2 | 9/2020 | Wallace et al. |
| 10,799,331 B2 | 10/2020 | Hauser et al. |
| 10,835,268 B2 | 11/2020 | Wallace et al. |
| 10,835,271 B2 | 11/2020 | Ma |
| 10,842,498 B2 | 11/2020 | Vale et al. |
| 10,842,513 B2 | 11/2020 | Greenhalgh et al. |
| 10,856,894 B2 | 12/2020 | Wallace et al. |
| 10,863,999 B2 | 12/2020 | Wallace et al. |
| 10,888,342 B2 | 1/2021 | Wallace et al. |
| 10,888,343 B2 | 1/2021 | Wallace et al. |
| 10,932,799 B2 | 3/2021 | Sirivong |
| 10,939,934 B2 | 3/2021 | Lockard et al. |
| 10,952,760 B2 | 3/2021 | Brady et al. |
| 10,960,178 B2 | 3/2021 | Savastano et al. |
| 11,000,682 B2 | 5/2021 | Merritt et al. |
| 11,026,709 B2 | 6/2021 | Greenhalgh et al. |
| 11,058,451 B2 | 7/2021 | Marchand et al. |
| 11,065,018 B2 | 7/2021 | Buck et al. |
| 11,071,733 B1 | 7/2021 | Zaidi et al. |
| 11,076,808 B2 | 8/2021 | Levine |
| 11,077,188 B2 | 8/2021 | Kauvar et al. |
| 11,103,265 B2 | 8/2021 | Wallace et al. |
| 11,154,314 B2 | 10/2021 | Quick |
| 11,160,572 B2 | 11/2021 | Ulm, III |
| 11,191,558 B2 | 12/2021 | Nguyen et al. |
| 11,197,684 B1 | 12/2021 | Ngo et al. |
| 11,197,771 B2 | 12/2021 | Ferrera et al. |
| 11,207,096 B2 | 12/2021 | To et al. |
| 11,224,449 B2 | 1/2022 | Chou et al. |
| 11,229,445 B2 | 1/2022 | Ogle |
| 11,246,965 B2 | 1/2022 | Chen et al. |
| 11,253,291 B2 | 2/2022 | Wallace et al. |
| 11,259,824 B2 | 3/2022 | Brady et al. |
| 11,259,835 B2 | 3/2022 | Smith et al. |
| 11,291,463 B2 | 4/2022 | Atchaneeyasakul et al. |
| 11,304,723 B1 | 4/2022 | To et al. |
| 11,317,940 B2 | 5/2022 | Smith et al. |
| 11,337,714 B2 | 5/2022 | Ferrera et al. |
| 11,369,405 B2 | 6/2022 | Vardi et al. |
| 11,376,028 B1 | 7/2022 | Saadat et al. |
| 11,382,652 B2 | 7/2022 | Wasdyke et al. |
| 11,383,068 B2 | 7/2022 | Tran et al. |
| 11,395,675 B2 | 7/2022 | Echarri et al. |
| 11,399,711 B2 | 8/2022 | Cooper et al. |
| 11,406,403 B2 | 8/2022 | Casey et al. |
| 11,406,404 B2 | 8/2022 | Griffin |
| 11,433,218 B2 | 9/2022 | Quick et al. |
| 11,446,045 B2 | 9/2022 | Vale et al. |
| 11,458,286 B2 | 10/2022 | Bajema et al. |
| 11,471,183 B1 | 10/2022 | Deaton et al. |
| 11,478,262 B2 | 10/2022 | Ngo et al. |
| 11,497,512 B2 | 11/2022 | Wallace et al. |
| 11,497,514 B2 | 11/2022 | Greenhalgh et al. |
| 11,497,521 B2 | 11/2022 | Mallaby |
| 11,529,157 B2 | 12/2022 | Brady et al. |
| 11,529,158 B2 | 12/2022 | Hauser |
| 11,529,331 B2 | 12/2022 | Zeligs et al. |
| 11,534,593 B2 | 12/2022 | Franano et al. |
| 11,547,415 B2 | 1/2023 | Chou et al. |
| 11,553,935 B2 | 1/2023 | Buck et al. |
| 11,553,942 B2 | 1/2023 | Bonnette et al. |
| 11,559,382 B2 | 1/2023 | Merritt et al. |
| 11,576,724 B2 | 2/2023 | Ben-Oren et al. |
| 11,596,438 B2 | 3/2023 | Walzman |
| 11,596,769 B2 | 3/2023 | Walzman |
| 11,617,592 B2 | 4/2023 | Nayak et al. |
| 11,627,973 B2 | 4/2023 | Wallace et al. |
| 11,628,282 B2 | 4/2023 | Casey |
| 11,633,201 B2 | 4/2023 | Girdhar et al. |
| 11,642,145 B2 | 5/2023 | Vale et al. |
| 11,666,350 B2 | 6/2023 | Nguyen et al. |
| 11,712,256 B2 | 8/2023 | Vale et al. |
| 11,730,924 B2 | 8/2023 | Saadat et al. |
| 11,730,925 B2 | 8/2023 | Saadat et al. |
| 11,737,770 B2 | 8/2023 | Fitz et al. |
| 11,737,771 B2 | 8/2023 | Whelan |
| 11,751,893 B2 | 9/2023 | Bowman et al. |
| 11,751,900 B2 | 9/2023 | Vetter et al. |
| 11,771,450 B2 | 10/2023 | Wallace et al. |
| 11,771,875 B2 | 10/2023 | Malek et al. |
| 11,779,364 B2 | 10/2023 | Casey et al. |

(56) References Cited

U.S. PATENT DOCUMENTS

| | | |
|---|---|---|
| 11,779,406 B2 | 10/2023 | Sganga et al. |
| 11,786,269 B2 | 10/2023 | Escudero et al. |
| 11,786,699 B2 | 10/2023 | Ogle et al. |
| 11,793,400 B2 | 10/2023 | Patel et al. |
| 11,793,531 B2 | 10/2023 | Nguyen et al. |
| 11,793,542 B2 | 10/2023 | Pons |
| 11,801,114 B2 | 10/2023 | Lang |
| 11,812,980 B2 | 11/2023 | Wallace et al. |
| 11,819,228 B2 | 11/2023 | Buck et al. |
| 11,864,779 B2 | 1/2024 | Dinh |
| 12,089,867 B2 | 9/2024 | To et al. |
| 2001/0004700 A1 | 6/2001 | Honeycutt |
| 2001/0005909 A1 | 6/2001 | Findlay |
| 2002/0004680 A1 | 1/2002 | Plaia |
| 2002/0007190 A1 | 1/2002 | Wulfman |
| 2002/0029057 A1 | 3/2002 | McGuckin |
| 2002/0077642 A1 | 6/2002 | Patel |
| 2002/0077842 A1 | 6/2002 | Charisius |
| 2002/0107479 A1 | 8/2002 | Bates |
| 2002/0151918 A1 | 10/2002 | Lafontaine |
| 2002/0168467 A1 | 11/2002 | Puech |
| 2002/0169467 A1 | 11/2002 | Heitzmann |
| 2002/0169487 A1 | 11/2002 | Graindorge |
| 2002/0198550 A1 | 12/2002 | Nash |
| 2003/0018346 A1 | 1/2003 | Follmer |
| 2003/0078606 A1 | 4/2003 | Lafontaine |
| 2003/0100911 A1 | 5/2003 | Nash |
| 2003/0114869 A1 | 6/2003 | Nash |
| 2003/0125758 A1 | 7/2003 | Simpson |
| 2003/0139751 A1 | 7/2003 | Evans |
| 2003/0139802 A1 | 7/2003 | Wulfman |
| 2004/0006358 A1 | 1/2004 | Wulfman |
| 2004/0238312 A1 | 3/2004 | Sudau |
| 2004/0243162 A1 | 3/2004 | Wulfman |
| 2004/0087988 A1 | 5/2004 | Heitzmann |
| 2004/0097995 A1 | 5/2004 | Nash |
| 2004/0102772 A1 | 5/2004 | Baxter |
| 2004/0103516 A1 | 6/2004 | Bolduc |
| 2004/0147934 A1 | 7/2004 | Kiester |
| 2004/0167533 A1 | 8/2004 | Wilson |
| 2004/0167553 A1 | 8/2004 | Simpson |
| 2004/0167554 A1 | 8/2004 | Simpson |
| 2004/0181249 A1 | 9/2004 | Torrance |
| 2004/0199051 A1 | 10/2004 | Weisel |
| 2004/0202772 A1 | 10/2004 | Matsuda |
| 2004/0220519 A1 | 11/2004 | Wulfman |
| 2004/0230212 A1 | 11/2004 | Wulfman |
| 2004/0230213 A1 | 11/2004 | Wulfman |
| 2004/0235611 A1 | 11/2004 | Nistal |
| 2004/0236312 A1 | 11/2004 | Nistal |
| 2005/0004585 A1 | 1/2005 | Hall |
| 2005/0020327 A1 | 1/2005 | Chung |
| 2005/0020974 A1 | 1/2005 | Noriega |
| 2005/0059990 A1 | 3/2005 | Ayala |
| 2005/0113853 A1 | 5/2005 | Noriega |
| 2005/0149084 A1 | 7/2005 | Kanz |
| 2005/0177068 A1 | 8/2005 | Simpson |
| 2005/0197661 A1 | 9/2005 | Simpson |
| 2005/0197861 A1 | 9/2005 | Omori |
| 2005/0222519 A1 | 10/2005 | Simpson |
| 2005/0240146 A1 | 10/2005 | Nash |
| 2006/0020327 A1 | 1/2006 | Lashinski |
| 2006/0074442 A1 | 4/2006 | Noriega |
| 2006/0229646 A1 | 10/2006 | Sparks |
| 2006/0239982 A1 | 10/2006 | Simpson |
| 2006/0241564 A1 | 10/2006 | Corcoran |
| 2007/0135733 A1 | 6/2007 | Soukup |
| 2007/0225739 A1 | 9/2007 | Pintor |
| 2007/0250000 A1 | 10/2007 | Magnin |
| 2007/0282303 A1 | 12/2007 | Nash |
| 2007/0282350 A1 | 12/2007 | Hernest |
| 2007/0282358 A1 | 12/2007 | Remiszewski |
| 2008/0004643 A1 | 1/2008 | To |
| 2008/0004644 A1 | 1/2008 | To |
| 2008/0004645 A1 | 1/2008 | To |
| 2008/0004646 A1 | 1/2008 | To |
| 2008/0004647 A1 | 1/2008 | To |
| 2008/0045986 A1 | 2/2008 | To et al. |
| 2008/0103516 A1 | 5/2008 | Wulfman |
| 2008/0140101 A1 | 6/2008 | Carley |
| 2008/0234715 A1 | 9/2008 | Pesce |
| 2008/0249364 A1 | 10/2008 | Korner |
| 2009/0018565 A1 | 1/2009 | To et al. |
| 2009/0018566 A1 | 1/2009 | Escudero |
| 2009/0018567 A1 | 1/2009 | Escudero |
| 2009/0024085 A1 | 1/2009 | To |
| 2009/0043330 A1 | 2/2009 | To |
| 2009/0043380 A1 | 2/2009 | Blaha et al. |
| 2009/0234378 A1 | 9/2009 | Escudero |
| 2010/0010492 A1 | 1/2010 | Lockard |
| 2010/0049225 A1 | 2/2010 | To |
| 2010/0119578 A1 | 5/2010 | To et al. |
| 2010/0174302 A1 | 7/2010 | Heitzmann |
| 2010/0324567 A1 | 12/2010 | Root |
| 2010/0324576 A1 | 12/2010 | Pintor |
| 2011/0040315 A1 | 2/2011 | To |
| 2011/0112563 A1 | 5/2011 | To |
| 2011/0152906 A1 | 6/2011 | Escudero |
| 2011/0152907 A1 | 6/2011 | Escudero |
| 2011/0270289 A1 | 11/2011 | To |
| 2011/0301626 A1 | 12/2011 | To |
| 2012/0083810 A1 | 4/2012 | Escudero |
| 2013/0085515 A1 | 4/2013 | To |
| 2013/0090674 A1 | 4/2013 | Escudero |
| 2013/0096587 A1 | 4/2013 | Smith |
| 2013/0103062 A1 | 4/2013 | To |
| 2013/0103063 A1 | 4/2013 | Escudero |
| 2013/0158578 A1 | 6/2013 | Ghodke |
| 2013/0296901 A1 | 11/2013 | Olson |
| 2014/0039532 A1 | 2/2014 | Vrba |
| 2014/0058423 A1 | 2/2014 | Smith |
| 2014/0107680 A1 | 2/2014 | Escudero |
| 2015/0224585 A1 | 8/2015 | Kuroda |
| 2017/0273698 A1 | 9/2017 | McGuckin et al. |
| 2018/0193056 A1 | 7/2018 | Colyer et al. |
| 2020/0029801 A1 | 1/2020 | Tachibana et al. |
| 2020/0029998 A1 | 1/2020 | Ogle et al. |
| 2020/0060718 A1 | 2/2020 | Patel et al. |
| 2020/0129202 A1 | 4/2020 | Schoenle et al. |
| 2020/0315654 A1 | 10/2020 | Patel et al. |
| 2020/0352552 A1 | 11/2020 | Rousso et al. |
| 2021/0186541 A1 | 6/2021 | Thress |
| 2021/0378694 A1 | 12/2021 | Thress et al. |
| 2022/0039815 A1 | 2/2022 | Thress et al. |
| 2022/0142638 A1 | 5/2022 | Enright et al. |
| 2022/0151647 A1 | 5/2022 | Dolendo et al. |
| 2022/0152355 A1 | 5/2022 | Dolendo et al. |
| 2022/0387071 A1 | 12/2022 | To et al. |
| 2023/0218310 A1 | 7/2023 | Scheinblum et al. |
| 2023/0241302 A1 | 8/2023 | Merritt et al. |
| 2023/0248380 A1 | 8/2023 | Long et al. |
| 2023/0310751 A1 | 10/2023 | Merritt et al. |
| 2023/0389932 A1 | 10/2023 | Ozenne et al. |
| 2023/0355938 A1 | 11/2023 | Merritt et al. |
| 2024/0081857 A1 | 3/2024 | Luong et al. |
| 2024/0082540 A1 | 3/2024 | Brodt et al. |
| 2024/0157041 A1 | 5/2024 | Zikry et al. |

FOREIGN PATENT DOCUMENTS

| | | |
|---|---|---|
| EP | 0817594 | 3/1996 |
| EP | 0817595 | 3/1996 |
| EP | 0950456 A1 | 10/1999 |
| EP | 1158910 | 1/2000 |
| EP | 1176915 | 2/2002 |
| EP | 1178315 | 2/2002 |
| EP | 1315460 | 6/2003 |
| EP | 1603486 B1 | 6/2006 |
| EP | 1722694 | 11/2006 |
| EP | 1870044 | 12/2007 |
| EP | 1617893 A4 | 8/2008 |
| EP | 2579791 B1 | 6/2010 |
| EP | 2462881 | 6/2012 |
| EP | 2617372 B1 | 7/2013 |

(56) References Cited

FOREIGN PATENT DOCUMENTS

| | | |
|---|---|---|
| EP | 2641551 | 9/2013 |
| EP | 2424608 B1 | 3/2014 |
| EP | 2211732 B1 | 5/2018 |
| EP | 2164409 B1 | 8/2018 |
| EP | 3027126 B1 | 10/2019 |
| EP | 2931151 B1 | 11/2019 |
| JP | H0380872 | 4/1991 |
| JP | 2006511256 | 4/2006 |
| JP | 2011136180 A | 7/2011 |
| JP | 2013531542 A | 8/2013 |
| JP | 6266108 B2 | 1/2018 |
| JP | 6356604 B2 | 7/2018 |
| WO | WO 1992/001423 | 2/1992 |
| WO | WO 1992/014506 | 9/1992 |
| WO | WO 1994/024946 | 11/1994 |
| WO | WO 1995/021576 | 8/1995 |
| WO | WO 1996/029941 | 10/1996 |
| WO | WO 1996/029942 | 10/1996 |
| WO | WO 1999/023958 | 5/1999 |
| WO | WO 1999/035977 | 7/1999 |
| WO | WO 2000/054659 | 9/2000 |
| WO | WO 2000/054859 | 9/2000 |
| WO | WO 2001/064115 | 9/2001 |
| WO | WO 2001/074255 | 10/2001 |
| WO | WO 2001/076680 | 10/2001 |
| WO | WO 2005/084562 | 9/2005 |
| WO | WO 2005/123169 | 12/2005 |
| WO | WO 2006/028886 | 3/2006 |
| WO | WO 2007/010389 | 1/2007 |
| WO | WO 2008/005888 | 1/2008 |
| WO | WO 2008/005891 | 1/2008 |
| WO | WO 2009/005779 | 1/2009 |
| WO | WO 2009/054968 | 4/2009 |
| WO | WO 2009/126309 | 10/2009 |
| WO | WO 2009/144580 | 12/2009 |
| WO | WO 2010/050391 | 5/2010 |
| WO | WO 2010/054121 | 5/2010 |
| WO | WO 2011/044533 | 4/2011 |
| WO | WO 2013/056262 | 4/2013 |
| WO | WO 2013/172970 | 11/2013 |
| WO | WO 2015/017114 | 2/2015 |
| WO | WO 2016/001932 | 1/2016 |
| WO | WO 2020/234203 | 11/2020 |
| WO | PCT/US22/32428 | 6/2022 |
| WO | PCT/US2024/042773 | 8/2024 |

OTHER PUBLICATIONS

U.S. Appl. No. 63/126,847 (priority for U.S. Appl. No. 17/518,294, cited herein), filed Dec. 17, 2020, To, et al.—owned by Applicant.
U.S. Appl. No. 63/197,970 (priority for U.S. Appl. No. 17/518,294, cited herein), filed Jun. 7, 2021, To, et al.—owned by Applicant.
U.S. Appl. No. 63/520,029, filed Aug. 16, 2023, To, et al.—owned by Applicant.
Written opinion and search report for PCT/US22/32428, To—owned by Applicant, Jun. 7, 2022.
Extended European Search Reoort for EP 22820858, Mar. 27, 2024, To—owned by Applicant.
Caranfa, J.T., et al. Mechanical endovascular therapy for acute ischemic stroke: An indirect treatment comparison between Solitaire and Penumbra thrombectomy devices. PLoS ONE 13(3): e0191657 (2018) https://doi.org/10.1371/journal.pone.0191657.
Ikeno et al. Initial Experience with the Novel 6 F r-Compatible System for Debulking De Novo Coronary Arterial Lesions. Catheterization and Cardiovascular Interventions 62:308-17. (2004).
Kanjwal et al. Peripheral Arterial Disease—a Silent Killer. JK-Practitioner 11(4):225-32 (2004).
Nakamura et al. Efficacy and Feasibility of Helixcision for Debulking Neointimal Hyperplasia for In-Stent Restenosis. Catheterization and Cardiovascular Interventions 57:460-66 (2002).
Written opinion and search report for PCT/US2024/042773, To, et al.—owned by Applicant, Aug. 16, 2024.

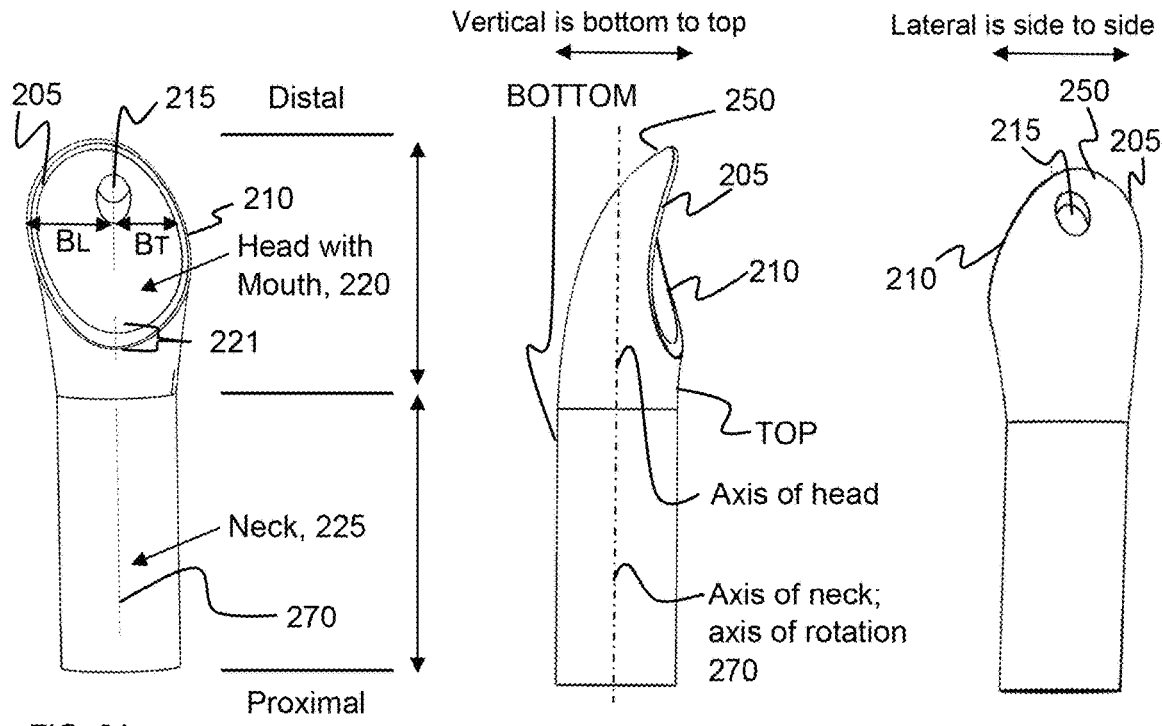
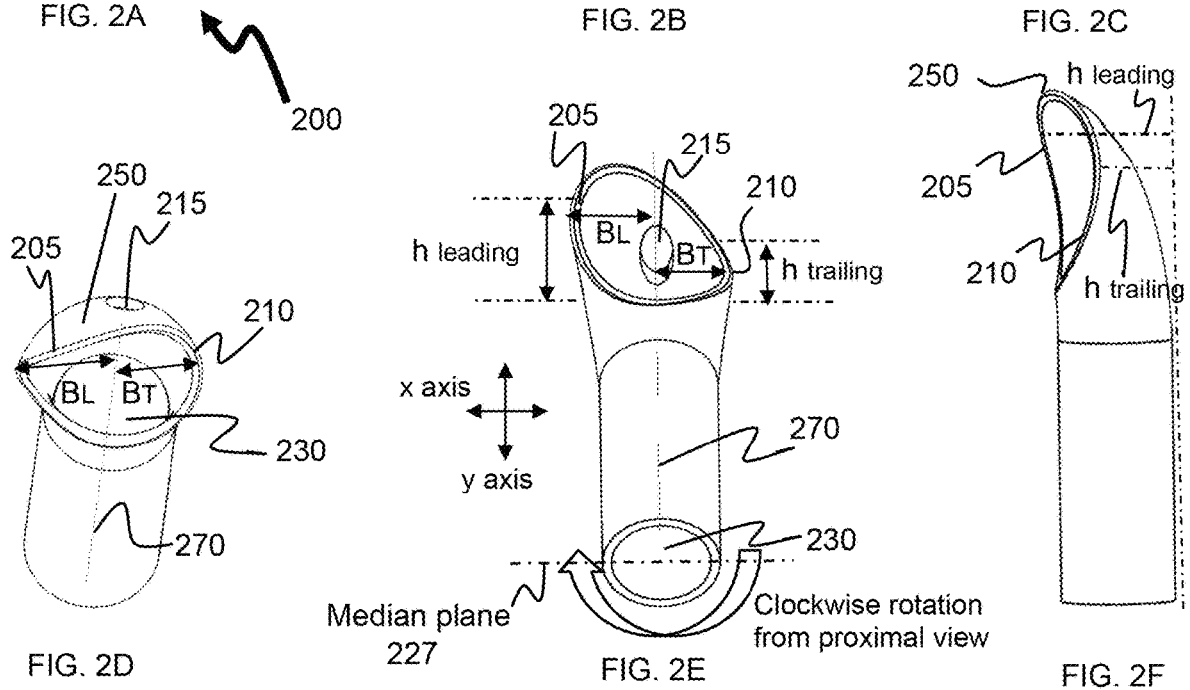

So = ΔB_L = sweep or length of deflection or deflection distance

Cutting edge for clockwise rotation from a proximal user perspective clockwise rotation from a proximal user perspective clockwise rotation from a proximal user perspective

THROMBECTOMY DEVICES WITH LATERAL AND VERTICAL BIAS

CROSS REFERENCES TO RELATED APPLICATIONS

This application claims the benefit of U.S. Provisional Application No. 63/520,029, filed Aug. 16, 2023, which is hereby incorporated by reference herein in it's entirety.

BACKGROUND

Field of the Invention

The teachings herein are directed generally to medical devices and methods, including devices and methods for performing thrombectomies.

Description of the Related Art

A thrombectomy is the removal of a blood clot from a blood vessel. Blood clots are made up of platelets and a meshwork of protein strands called fibrin. Clots in arteries have a different composition than clots in veins, in which clots in arteries contain mostly platelets and clots in veins contain mostly fibrin. Common applications for thrombectomies include any location in a blood vessel where a thrombus may occur. The thrombectomy removes the blood clot from the wall of a blood vessel to help alleviate symptoms of the condition, as well as the downstream complications that can include further vasculature complications, and perhaps even death from the release of an embolus.

State-of-the-art thrombectomy devices leave much to be desired, as many problems remain to be solved in the art, including (i) dragging expanded baskets along veins which can injure the vein walls or valves, (ii) clogging suction in the operation of the devices; (iii) removing too much blood while removing the thrombus; (iv) failing in the removal of tough or mature thrombi; and (v) failing to be versatile enough to handle each of the variety of soft, tough, fibrous, and hard tissue effectively, either not cutting all types of tissue or breaking up the tissue into pieces that can become dangerous emboli that can clog blood vessels downstream and, in some cases, cause death.

A versatile device that can handle each of the variety of soft, tough, fibrous, and hard tissue effectively, can also be useful in removing an atheroma from the lumen of an artery. Atherosclerosis is also referred to as plaque on the luminal wall of an artery. Plaque includes deposits of fatty substances, cholesterol, cellular waste products, calcium, and fibrin. Both the atherosclerosis and thrombus pose a risk of fragmenting into the blood stream, and moving to the heart, brain, or lungs, causing health complications and often proving to be fatal.

One of skill will appreciate the devices and systems taught herein that (i) can effectively cut and remove all types of thrombus and atheroma tissue, whether soft, tough, or hard; (ii) can safely collect and remove such while avoiding the release of tissue fragments, such as emboli; and (iii) can effectively treat a blood vessel with a reduced risk of suffering vessel injuries that can lead to increased stenosis. Of particular interest herein, among the several indications taught for the technologies, is (i) the removal of a venous thrombus, and (ii) the removal of a pulmonary arterial thrombus, also referred to as a pulmonary embolism.

SUMMARY

Thrombectomy systems, devices, and methods of using them are provided. Several embodiments are taught for the technologies herein, and these embodiments include systems, methods, and devices for (i) the removal of arterial and venous thrombus, and (ii) the removal of a pulmonary arterial thrombus, also referred to as a pulmonary embolism. In some embodiments, the systems, devices, and methods taught herein can be used in atherectomies. The technologies taught herein can effectively cut and remove all types of thrombus and atheroma tissue, whether soft, tough, or hard, which will be appreciated by those of skill.

A thrombectomy device is provided. In some embodiments, the thrombectomy device includes
 a flexible rotating shaft with a proximal end, a distal end, and a lumen;
 a curved, tubular cutter operably connected to the distal end of the flexible rotating shaft, the tubular cutter including a head with an axis with a mouth having a z-axis, a neck connected to the head and having an axis of rotation, and an angle, $\theta z$, ranging from 90° to 135°, between the z-axis of the mouth and the axis of rotation, the mouth the configured with
    a leading edge having a highest height, h-leading;
    a trailing edge having a lowest height, h-trailing;
    a vertical bias ratio of h-leading/h-trailing ranging from 1.05 to 2.0;
    a distance, $B_L$, between the axis of rotation and the leading edge;
    a distance, $B_T$, between the axis of rotation and the trailing edge; and,
    a lateral bias ratio of $B_L/B_T$ ranging from 1.05 to 2.0;
 a delivery sheath for delivering the cutter to a target site in a subject having a tissue for removal; and,
 a vacuum port configured for operable communication with a vacuum source to facilitate transport of the tissue out of the subject.

In some embodiments, the devices include a delivery sheath for a safe delivery of the cutter to the target site for the tissue removal. The proviso, however, is that in some embodiments, the devices do not include a delivery sheath by preference or by design.

In some embodiments, the cutter is deflected from the axis of rotation to create a deflection distance between the leading edge of the cutter and the axis of rotation.

In some embodiments, the axis of the head is at a vertical angle, $\phi$, with the axis of rotation, wherein $\phi$ ranges from 0° to 90° to create a deflection distance between the leading edge of the cutter and the axis of rotation.

In some embodiments, the axis of the head is at a lateral angle, $\theta o$, with the axis of rotation, wherein $\theta o$ ranges from 0° to 90° to create a deflection distance between the leading edge of the cutter and the axis of rotation.

In some embodiments, the flexible rotating shaft is deflected at an angle, $\theta m$, with the axis of rotation to form a curve region in the flexible rotating shaft, wherein $\theta m$ ranges from 0-90 degrees to create a deflection distance between the leading edge of the cutter and the axis of rotation.

In some embodiments, the mouth has a cross-sectional area that is equal to, or less than, the lumen of the flexible, rotating shaft.

In some embodiments, the z-axis of the mouth is an angle, $\theta r$, from a plane containing the curve region to open the mouth toward the target site for the tissue for removal.

In some embodiments, the device further includes a straightening sheath.

Systems are also provided. In some embodiments, a system includes the devices taught herein, along with a handle that includes a motor operably connected to a drive assembly that includes the flexible rotating shaft and the cutter, the motor configured to provide a rotational movement to the flexible, rotating shaft for rotating the cutter.

In some embodiments, a system includes the devices taught herein, and the delivery sheath is a straightening sheath.

In some embodiments, a system includes the devices taught herein, wherein the z-axis of the mouth is an angle, θr, from a plane containing the curve region to open the mouth toward the target site for the tissue for removal.

In some embodiments, a system includes the devices taught herein, along with a vacuum source, and wherein the vacuum port is in operable connection with the vacuum for removal of the tissue from the system.

In some embodiments, the systems include a delivery sheath for a safe delivery of the cutter to the target site for the tissue removal. The proviso, however, is that in some embodiments, the systems do not include a delivery sheath by preference or by design.

In some embodiments, a system includes the devices taught herein, wherein the delivery sheath is a straightening sheath, the system further comprising a vacuum source; wherein the vacuum port is in operable connection with the vacuum for removal of the tissue from the system.

Methods of treatment are also provided, and any blood vessel can be treated using the devices and systems taught herein. In some embodiments, a method of performing a thrombectomy using any device taught herein is provided. The method can include:
 creating a point of entry in a vascular lumen of the subject;
 inserting the thrombectomy device into the vascular lumen;
 delivering the cutter to the target site in the delivery sheath, the target site having the tissue for removal;
 cutting the tissue from the vascular lumen with the cutter of the thrombectomy device;
 and,
 removing the thrombectomy device from the vascular lumen of the subject.

In some embodiments, the methods include using a delivery sheath for a safe delivery of the cutter to the target site for the tissue removal. The proviso, however, is that in some embodiments, the methods do not include using a delivery sheath by preference or by design.

In some embodiments, the method further includes inserting a guidewire in the point of entry and delivering the guidewire to the target location of the thrombus, and guiding the thrombectomy device to the location of the thrombus on the guidewire.

In some embodiments, the method further includes discharging the tissue from the vascular lumen with a vacuum.

In some embodiments, the method includes:
 creating a point of entry in a vascular lumen of the subject;
 inserting the thrombectomy device into the vascular lumen, the thrombectomy device having a deflection distance;
 delivering the cutter to the target site, the target site having the tissue for removal;
 cutting tissue from the vascular lumen with the cutter of the thrombectomy device;
 and,
 removing the thrombectomy device from the vascular lumen of the subject.

In some embodiments, the method includes inserting a guidewire in the point of entry and delivering the guidewire to the target location of the tissue, and guiding the cutter to the location of the thrombus on the guidewire.

In some embodiments, the method includes discharging the tissue from the vascular lumen with a vacuum.

In the course of the teachings of the above in the following detailed description, methods of making thrombectomy tubular cutters, thrombectomy devices, and thrombectomy systems are also provided. Methods of treating any vein or artery is provided including, for example, (i) the removal of a venous thrombus, (ii) the removal of a pulmonary arterial thrombus, also referred to as a pulmonary embolism, and (iii) the removal of arterial plaque.

BRIEF DESCRIPTION OF THE FIGURES

FIGS. 2A-2H illustrate a thrombectomy tubular cutter, according to some embodiments.

DETAILED DESCRIPTION

Figure 1A:
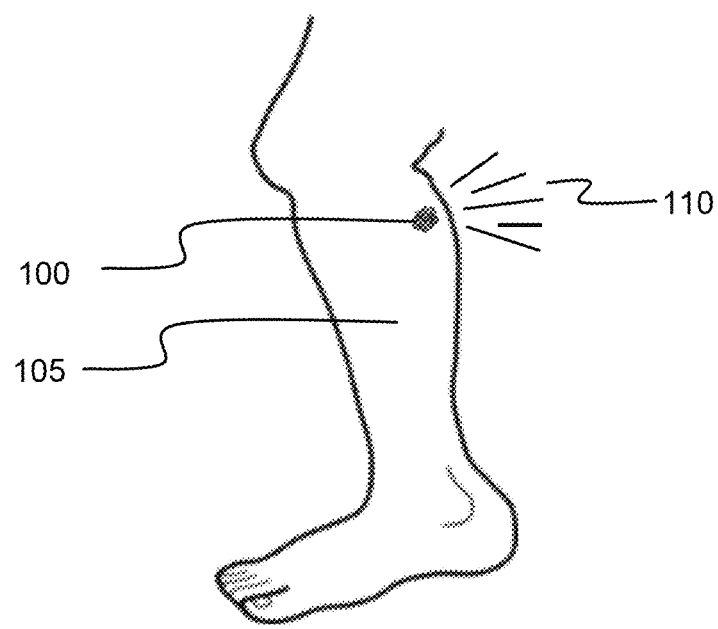
FIGS. 1A-1E illustrate a human leg containing a thrombus, a partial blockage of a blood vessel from the thrombus, the release of an embolus, a total blockage of the blood vessel from the thrombus, and an accumulation of platelets behind a thrombus.

Thrombectomy devices, and methods of using them are provided, namely devices and methods that (i) can effectively cut and remove thrombus tissue; (ii) can safely collect and remove plaque particles to avoid release of emboli; (iii) can effectively treat a blood vessel with a reduced risk of suffering vessel injuries. And, importantly, one of skill will certainly appreciate having a thrombectomy device that, (iv) can also handle tight or tough lesions having little to no luminal opening in the lesion. The thrombectomy devices can have a cutting head that includes the shape of a tubular cutter with a cutting edge that removes thrombus tissue from a blood vessel when rotating the head in the lumen of the blood vessel. Several embodiments are taught for the technologies herein, and these embodiments include systems, methods, and devices for (i) the removal of a venous thrombus, and (ii) the removal of a pulmonary arterial thrombus, also referred to as a pulmonary embolism.

One of skill will appreciate that a "subject" receiving a thrombectomy can be a "patient" that is receiving the thrombectomy. As such, the term "subject" and "patient" can be used interchangeably and refer to an animal such as a mammal including, but not limited to, non-primates such as, for example, a cow, pig, horse, cat, dog, rabbit, rat and mouse; and primates such as, for example, a monkey or a human. The subject can also be a cadaver, in some embodiments, or a portion of a cadaver.

The devices, systems, and methods taught herein can remove blood clots from arteries or veins, for example, in your heart, brain, lungs, abdomen, arms, and legs. Arterial clots can also take root in your kidneys, intestines, or eyes, although considered rare. In some embodiments, the blood clot is stationary, which is a "thrombosis" that can block blood flow, and the devices, systems, and methods taught herein can remove the thrombosis. If the blood clot breaks loose and moves in the blood vessel, it becomes an "embolism" which can travel to other parts of the body and become dangerous and even fatal.

Arterial thrombi can be referred to as white thrombi, and are characterized by predominance of platelets. Venous thrombi can be referred to as red thrombi, and are characterized by predominance of red blood cells. A thrombus can start soft and become more fibrous and harder over time. Thrombus formation can play a major role in the formation and histopathologic disorders of in arteries and old saphenous vein grafts (SVGs). A non-occlusive thrombus can be formed by silent plaque rupture or erosion. As the thrombus increases in size to become flow occlusive, a provisional matrix forms at healed lesions as an organized thrombus which may contain fibrin and be infiltrated by smooth muscle cell granulation tissue with proteoglycans and type III collagen. The thrombus proximal and distal to the site of a plaque rupture, for example, can be replaced by fibrous plaque in some embodiments. In some embodiments, the devices, systems, and methods can be used to treat SVGs. In some embodiments, the devices, systems, and methods can be used to inhibit the onset of plaque formation that would follow the development of the thrombus.

The devices, systems, and methods taught herein can be used, for example, to treat, or inhibit the onset of, symptoms by removing the blood clots from arteries or veins of a subject. As such, the devices, systems, and methods taught herein can remove arterial clots or venous clots. In some embodiments, the devices, systems, and methods treat, or inhibit the onset of, symptoms from a clot in the arms or legs including redness and warmth with swelling, tenderness, intense cramping, or any combination thereof. In some embodiments, the devices, systems, and methods treat, or inhibit the onset of, symptoms from a clot in the abdomen including stomach pain, diarrhea, vomiting, or any combination thereof. In some embodiments, the devices, systems, and methods treat, or inhibit the onset of, symptoms from a clot in the heart including breathing problems, nausea, dizziness, sweating, pain and heaviness in the chest, or any combination thereof. In some embodiments, the devices, systems, and methods treat, or inhibit the onset of, symptoms from a clot in the lungs including coughing-up of blood and a racing heart, shortness of breath, sweating, fever, sharp chest pain, or any combination thereof. In some embodiments, the devices, systems, and methods treat, or inhibit the onset of, symptoms from a clot in the brain including a headache; dizziness; difficulty talking; difficulty seeing clearly; weakness in the subject's face, arms, or legs; or any combination thereof.

The devices, systems, and methods taught herein can be used, for example, to remove three types of blood clots that form in the veins. In some embodiments, the devices, systems, and methods taught herein can be used, to remove (i) a superficial venous thrombosis close to the surface of skin; (ii) a deep vein thrombosis (DVT) that forms deep in the body including in the lower leg, thigh, pelvis, arm, intestines, liver, kidney, or brain; and, (iii) a pulmonary embolism (PE) in the lungs.

Figure 1B:
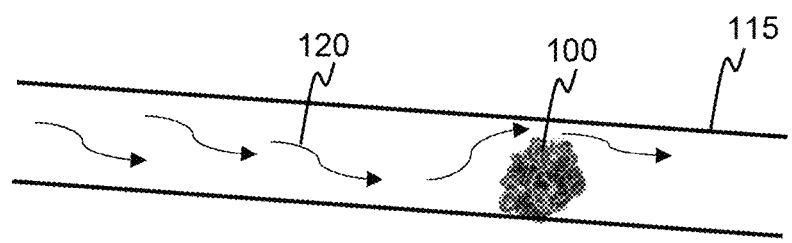
Figure 1C:
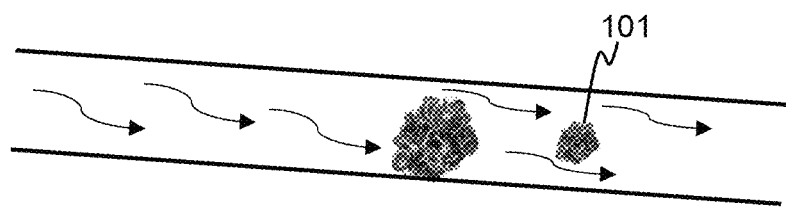
Figure 1D:
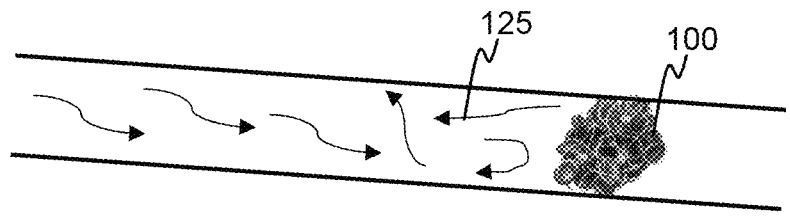
Figure 1E:
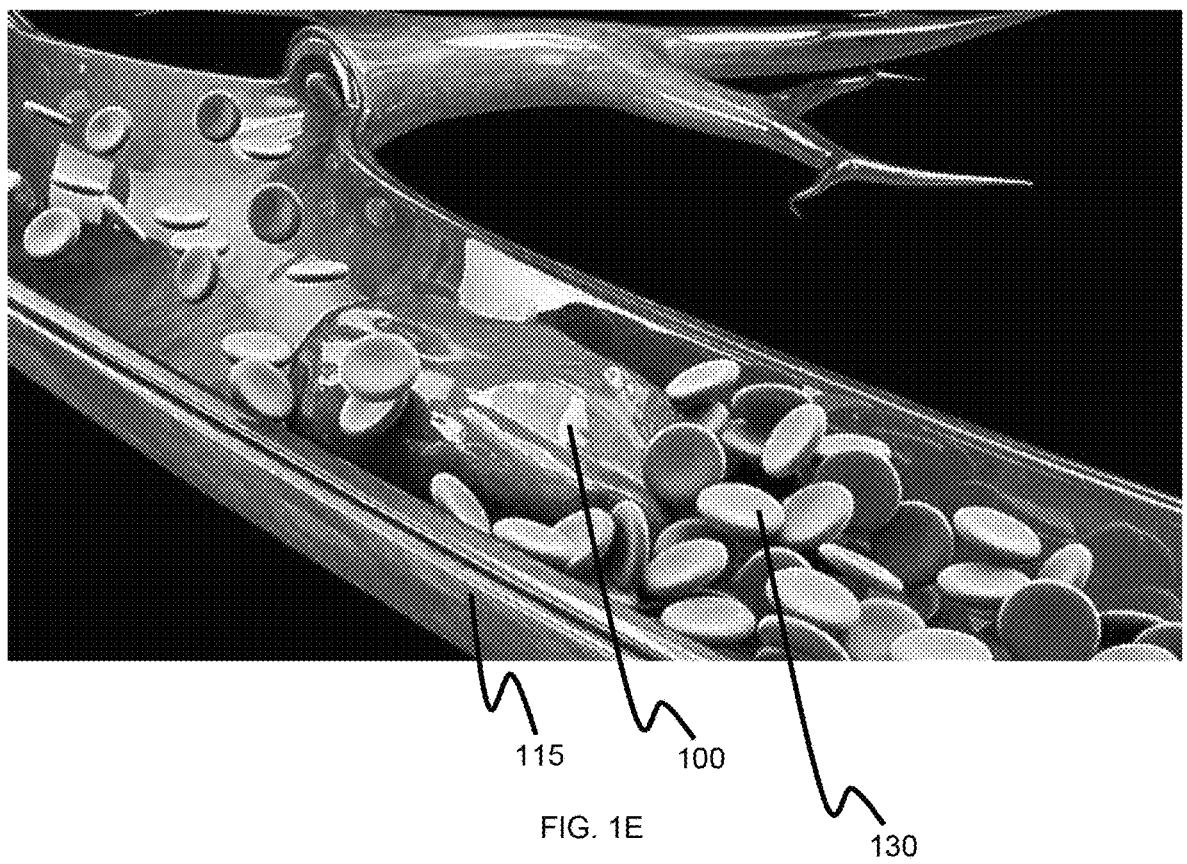

FIGS. 1A-1E illustrate a human leg containing a thrombus, a partial blockage of a blood vessel from the thrombus, the release of an embolus, a total blockage of the blood vessel from the thrombus, an accumulation of platelets behind a thrombus. FIG. 1A illustrates a subject's leg 105 with symptomatic pain 110 from a thrombus 100 in a blood vessel 115 in the subject's leg 105. FIG. 1B illustrates a partial blockage of the blood vessel 115 from the thrombus 100 that has deposited on the wall of the blood vessel 115. FIG. 1C illustrates the release of an emboli 101 within the blood vessel 115 which, one of skill will appreciate, can result in a more serious set of symptoms that can include death. FIG. 1D illustrates a total blockage of the blood vessel 115 from the thrombus 100 that results in backflow, or pooling, 125 behind the thrombus 100 in the blood vessel 115. FIG. 1E is a more anatomically correct illustration of the blood vessel 115 containing the thrombus 100, in which there is an accumulation of platelets behind the thrombus 100.

The thrombectomy devices taught herein can include a flexible rotating shaft with a proximal end, a distal end, and a lumen; a tubular cutter at the distal end of the rotating shaft, the tubular cutter having a proximal end and a distal end, and a top and a bottom, the tubular cutter configured with a mouth having a rim with a cutting edge, the mouth having (i) an inlet; and (ii) an outlet in communication with the lumen of the flexible rotating shaft; and, a neck having a central axis, the neck configured to operably connect and communicate with the lumen of the flexible rotating shaft. The systems can also include a vacuum port configured for operable communication with a vacuum source.

In some embodiments, methods of treating a thrombosis are provided. These methods can include creating a point of entry into the vasculature of the subject, advancing a thrombectomy device taught herein to the site of the thrombus through the point of entry, removing the thrombus with the thrombectomy device, and removing the thrombectomy device from the subject. In some embodiments, the methods include advancing a guidewire to the site of the thrombus, advancing the thrombectomy device to the thrombus over the guidewire, and removing the guidewire from the subject. In some embodiments, the method is used to treat a venous thrombosis. In some embodiments, the method is used to treat a superficial vein thrombosis. In some embodiments, the method is used to treat a deep vein thrombosis (DVT). In some embodiments, the method is used to treat a saphenous vein thrombosis. In some embodiments, the method is used to treat a renal vein thrombosis. In some embodiments, the method is used to treat an arterial thrombosis.

Figure 2G:
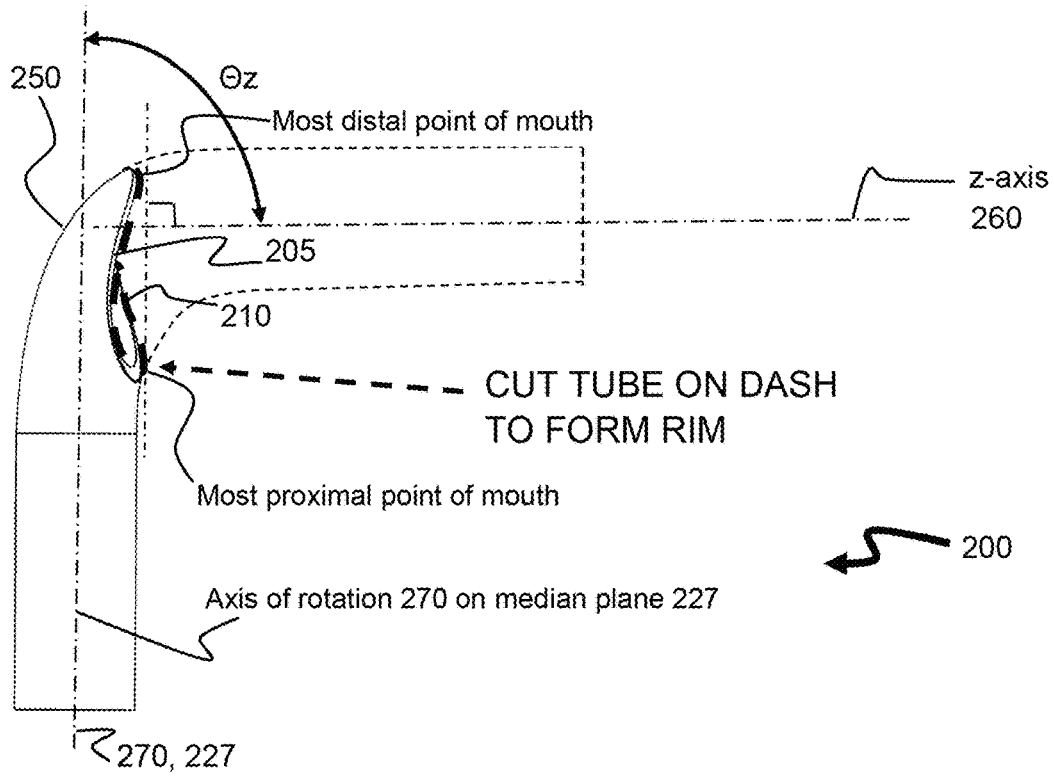

The thrombectomy tubular cutter can be referred to as a "tubular cutter", "cutter", "cutting head", or the like, in some embodiments. FIGS. 2A-2H illustrate various views showing features of a thrombectomy tubular cutter, according to some embodiments. FIG. 2A is a top-down view of the thrombectomy tubular cutter. As shown in FIG. 2A, the tubular cutter 200 can have a head with mouth 220 and a neck 225 having a lumen or throat 230 with a central axis 270, which can also be referred to as an "axis of rotation" in some embodiments. The head or mouth 220 of the thrombectomy tubular cutter 200 can have a rim 221 that has a cutting edge 205. In some embodiments, the thrombectomy tubular cutter 200 can have a guidewire port 215 located to guide the thrombectomy tubular cutter 200 on a guidewire (not shown) into a vascular lumen to a target site of a thrombus 100. In some embodiments, the thrombectomy tubular cutter 200 does not have a guidewire port 215. In some embodiments, the rim 221 can have a curvature.

In some embodiments, the rim 221 can have a trailing edge 210, noting that the relationship between the cutting edge 205 and the trailing edge 210 is a design feature that can vary in the cutters taught herein. For example, the cutting edge 205 can be referred to as "the leading edge", the leading edge 205 configured to reach the target site of tissue excision first, before the trailing edge 210, upon a rotation of the cutting head 200. The top and bottom of the cutter are shown in FIG. 2B, the axis of the head and the axis of the neck (axis of rotation), where the axis of the head is concentric with the axis of the neck, along with a description of how the term "vertical" describes a top-to-bottom or bottom-to-top orientation. From a viewpoint of the user, viewing the cutting head 200 from the proximal end with the top side of the cutter oriented upward, a left-hand, or counter clockwise rotation of the cutting head 200 would require the leading edge 205 to be on the right side. Likewise, from the viewpoint of the user, viewing the cutting head 200 from the proximal end with the top side of the cutter oriented upward, a right-hand, or clockwise rotation of the cutting head 200 would require the leading edge 205 to be on the left side.

A desirable design feature that can be included in the configuration of the cutter is a "bias" of the cutting surface. The "bias" can be defined as an imbalance of distances between the leading edge 205 from the axis of rotation 270, referred to as $B_L$ and the trailing edge 210 from the axis of rotation 270, referred to as $B_T$. In some embodiments $B_L$ is greater than $B_T$. $B_L$ is measured at the furthest point away from and normal to the axis of rotation on the leading edge. Br is measured at the furthest point away from and normal to the axis of rotation on the trailing edge. Since the actual relative differences between $B_L$ and $B_T$ can depend on the size of the cutting head, it should be appreciated that the bias, a can be expressed as a ratio, which can be referred as a "lateral bias" ratio in some embodiments. In some embodiments, the ratio of $B_L/B_T$ can range from 1.00 to 2.00, 1.05 to 2.00, 1.10 to 2.00, 1.15 to 2.00, 1.20 to 2.00, 1.25 to 2.00, 1.30 to 2.00, 1.35 to 2.00, 1.40 to 2.00, 1.45 to 2.00, 1.50 to 2.00, from 1.00 to 1.95, from 1.00 to 1.90, from 1.00 to 1.85, from 1.00 to 1.80, from 1.00 to 1.75, from 1.00 to 1.70, from 1.00 to 1.65, from 1.00 to 1.60, from 1.00 to 1.55, from 1.00 to 1.50, from 1.00 to 1.45, from 1.00 to 1.40, from 1.00 to 1.35, from 1.00 to 1.30, from 1.00 to 1.25, from 1.00 to 1.20, from 1.00 to 1.15, from 1.00 to 1.10, from 1.00 to 1.05, or any ratio or range therein in increments of 0.01. In some embodiments, the $B_L$ is greater than $B_T$ by 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or any amount or range therein in increments of 0.1%. In some embodiments, the $B_L$ is greater than $B_T$ by 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or any amount or range therein in increments of 0.1%. In some embodiments, the $B_L$ is greater than $B_T$ by 1.0×, 2.0×, 3.0×, 4.0×, or any amount or range therein in amounts of 0.1×.

FIGS. 2B and 2F are lateral views of the thrombectomy tubular cutter 200 showing the overlap of curvatures of the cutting edge 205 and trailing edge 210 that can be configured to facilitate an efficient removal of the thrombus 100, in some embodiments. The presence of a smooth, non-cutting surface 250 on the distal end of the head is noted. In these embodiments, the curvature can include the cutting edge 205 and the trailing edge 210.

FIG. 2C is a view from the bottom that shows the optional guidewire port 215 of the thrombectomy tubular cutter 200, the cutting edge 205 and the trailing edge 210, along with a description of how the term "lateral" describes a side to side orientation. FIG. 2D is a distal-to-proximal perspective view showing the lumen or throat 230, as it is configured relative to the optional guidewire port 215 (sharing concentric axes with the throat 230 in this embodiment), the cutting edge 205, and the trailing edge 210 of the thrombectomy tubular cutter 200.

A cutting head 200 configured for the right-hand, or clockwise rotation from a proximal viewpoint of the user is illustrated in FIG. 2E, and it should be appreciated that the left-hand, or counterclockwise rotation is the mirror image, which means the leading edge 205 and trailing edge 210 will be switched.

FIG. 2E is a proximal-to-distal perspective view showing the lumen or throat 230, as it is configured relative to the optional guidewire port 215 (sharing concentric axes with the throat 230 in this embodiment), the cutting edge 205, and the trailing edge 210 of the tubular cutter 200. It should be appreciated that the lumen 230 and optional guidewire port 215 do not have to share concentric axes in some embodiments.

FIGS. 2E and 2F provide perspective views of the leading edge 205 and the trailing edge 210, showing how the leading edge 205 can be configured to lead the trailing edge. FIG. 2E is a top down perspective, having 0° rotation from the median plane 227 of the neck 225, in which the height, h-leading, of leading edge 205 is more than the height, h-trailing, of trailing edge 210 as measured from the bottom of the neck. The h-leading is measured at the highest point of the leading edge and normal to the bottom of the cutter, and h-trailing is measured at the lowest point of the trailing edge and normal to the bottom of the cutter. Since the relative differences in height, Δh, can depend on the size of the cutting head, it should be appreciated that the relative differences in height, Δh, can be expressed as a ratio, which can be referred to as a "vertical bias" ratio in some embodiments. In some embodiments the ratio of h-leading/h-trailing can range from 1.00 to 2.00, 1.05 to 2.00, 1.10 to 2.00, 1.15 to 2.00, 1.20 to 2.00, 1.25 to 2.00, 1.30 to 2.00, 1.35 to 2.00, 1.40 to 2.00, 1.45 to 2.00, 1.50 to 2.00, from 1.00 to 1.95, from 1.00 to 1.90, from 1.00 to 1.85, from 1.00 to 1.80, from 1.00 to 1.75, from 1.00 to 1.70, from 1.00 to 1.65, from 1.00 to 1.60, from 1.00 to 1.55, from 1.00 to 1.50, from 1.00 to 1.45, from 1.00 to 1.40, from 1.00 to 1.35, from 1.00 to 1.30, from 1.00 to 1.25, from 1.00 to 1.20, from 1.00 to 1.15, from 1.00 to 1.10, from 1.00 to 1.05, or any ratio or range therein in increments of 0.01. In some embodiments, the h-leading is greater than h-trailing by 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or any amount or range therein in increments of 0.1%. In some embodiments, the h-leading is greater than h-trailing by 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or any amount or range therein in increments of 0.1%. In some embodiments, the h-leading is greater than h-trailing by 1.00×, 2.00×, 3.00×, 4.00×, or any amount or range therein in amounts of 0.01×

FIG. 2G illustrates how a curved, tubular cutter can be fabricated, in some embodiments, in which a curved tube is cut to form a rim with a desired configuration. For example, the rim can be configured helical, in some embodiments, and with a cutting edge 205 and a trailing edge 210, at least in some embodiments. The curve of the tube can be used to configure an angle, $\Theta z$, between the z-axis of the mouth and the central axis 270 of the neck or throat 230, in some embodiments.

The z-axis of the mouth is defined as a line (i) orthogonal to a line connecting the most distal point of the mouth to the most proximal point of the mouth on the y-axis and (ii) orthogonal to the median plane on the x-axis, referring to FIG. 2E.

It should be appreciated that the angle, $\Theta z$, between the z-axis of the mouth and the central axis 270 of the neck or throat 230 can be configured independent of the angle of the curve of tube, merely by angling the cut of the tube on the dash to form the rim. Such variations in the fabricating methods can be used to form rims and mouths of varying desirable configurations.

The thrombectomy tubular cutter 200 can be made of any medical grade material that is known be useful in the making of cutting devices that are used in vivo in a subject in a sterile surgical environment. In some embodiments, the thrombectomy tubular cutter 200 can be made polymers such as PEEK, polycarbonate, PET, polyacrylamide, PEBAX, polyethylene, or a fluoropolymer such as FEP, PTFE, or PVDF. In some embodiments, the thrombectomy tubular cutter 200 can be made of a surgical grade metal such as stainless steel, titanium alloys, or cobalt alloys. In some embodiments the cutter can be made of ceramic or glass. In some embodiments, the thrombectomy tubular cutter 200 can be coated with a lubricious coating such as silicone oil, parylene, a hydrophilic coating, a diamond coating, a fluoropolymer coating, a ceramic coating, or any combination thereof. Such coatings can facilitate trouble free use of the thrombectomy tubular cutter. For example, such coatings can help to reduce friction in engulfing and conveying clot into shaft.

In some embodiments, the angle, $\theta z$, between the central axis of the neck and the z-axis of the mouth can range from 0° to 180°, from 0° to 90°, from 90° to 180°, from 120° to 180°, or any amount or range therein in increments of 1°. In some embodiments, the angle, $\theta z$, between the central axis of the neck and the z-axis of the mouth can range from 1° to 30°, from 2° to 30°, from 3° to 30°, from 4° to 30°, from 5° to 30°, 6° to 30°, from 7° to 30°, from 8° to 30°, from 9° to 30°, from 10° to 30°, from 15° to 30°, from 20° to 30°, from 25° to 30°, or any range or amount therein in increments of 1°. In some embodiments, the angle, $\theta z$, between the central axis of the neck and the z-axis of the mouth can range from 1° to 45°, from 2° to 45°, from 3° to 45°, from 4° to 45°, from 5° to 45°, 6° to 45°, from 7° to 45°, from 8° to 45°, from 9° to 45°, from 10° to 45°, from 15° to 45°, from 20° to 45°, from 25° to 45°, from 30° to 45°, from 35° to 45°, from 40° to 45°, from, or any range or amount therein in increments of 1°. In some embodiments, the angle, $\theta z$, can range from 1° to 60°, from 2° to 60°, from 3° to 60°, from 4° to 60°, from 5° to 60°, 6° to 60°, from 7° to 60°, from 8° to 60°, from 9° to 60°, from 10° to 60°, from 15° to 60°, from 20° to 60°, from 25° to 60°, from 30° to 60°, from 35° to 60°, from 40° to 60°, from 45° to 60°, from 50° to 60°, from 55° to 60°, or any range or amount therein in increments of 1°. In some embodiments, the angle, $\theta z$, between the central axis of the neck and the z-axis of the mouth can range from 1° to 90°, from 2° to 90°, from 3° to 90°, from 4° to 90°, from 5° to 90°, 6° to 90°, from 7° to 90°, from 8° to 90°, from 9° 90°, from 10° to 90°, from 15° to 90°, from 20° to 90°, from 25° to 90°, from 30° to 90°, from 35° to 90°, from 40° to 90°, from 45° to 90°, from 50° to 90°, from 55° to 90°, from 60° to 90°, from 65° to 90°, from 70° to 90°, from 75° to 90°, from 80° to 90°, from 85° to 90°, or any range or amount therein in increments of 1°. In some embodiments, the angle, $\theta z$, between the central axis of the neck and the z-axis of the mouth can range from 1° to 120°, from 2° to 120°, from 3° to 120°, from 4° to 120°, from 5° to 120°, 6° to 120°, from 7° to 120°, from 8° to 120°, from 9° 120°, from 10° to 120°, from 15° to 120°, from 20° to 120°, from 25° to 120°, from 30° to 120°, from 35° to 120°, from 40° to 120°, from 45° to 120°, from 50° to 120°, from 55° to 120°, from 60° to 120°, from 65° to 120°, from 70° to 120°, from 75° to 120°, from 80° to 120°, from 85° to 120°, from 90° to 120°, from 95° to 120°, from 100° to 120°, from 110° to 120°, from 115° to 120°, or any range or amount therein in increments of 1°.

In some embodiments, the angle, $\theta z$, between the central axis of the neck and the z-axis of the mouth can range from 25° to 55°, from 10° to 110°, from 20° to 110°, from 25° to 110°, from 30° to 110°, from 35° to 110°, from 40° to 110°, from 45° to 110°, from 10° to 100°, from 20° to 100°, from 25° to 100°, from 30° to 100°, from 35° to 100°, from 40° to 100°, from 45° to 100°, or any range therein in increments of 1°. In some embodiments, the angle, $\theta z$, between the central axis of the neck and the z-axis of the mouth can range from 2° to 40°, from 3° to 35°, from 4° to 30°, from 5° to 25°, from 5° to 40°, from 5° to 35°, from 10° to 40°, from 10° to 35°, from 10° to 25°, from 15° to 40°, from 15° to 35°, from 15° to 25°, or any range or amount therein in increments of 1°. In some embodiments, the angle, $\theta z$, between the central axis of the neck and the z-axis of the mouth can be 0°, 1.0°, 2.0°, 3.0°, 4.0°, 5.0°, 6.0°, 7.0°, 8.0°, 9.0°, 10.0°, 11.0°, 12.0°, 13.0°, 14.0°, 15.0°, 16.0°, 17.0°, 18.0°, 19.0°, 20.0°, 21.0°, 22.0°, 23.0°, 24.0°, 25.0°, 26.0°, 27.0°, 28.0°, 29.0°, 30.0°, 31.0°, 32.0°, 33.0°, 34.0°, 35.0°, 36.0°, 37.0°, 38.0°, 39.0°, 40.0°, 41.0°, 42.0°, 43.0°, 44.0°, 50.0°, 55.0°, 60.0°, 65.0°, 70.0°, 75.0°, 80.0°, 85.0°, 90.0°, 95.0°, 100.0°, 105.0°, 110.0°, 115.0°, 120.0°, 125.0°, 130.0°, 135.0°, 140.0°, 145.0°, 150.0°, 155.0°, 160.0°, 165.0°, 170.0°, 175.0°, 180.0°, or any angle, $\theta z$, or range therein in 1° increments.

Blood vessel lumen diameters range considerably in size, becoming quite large, perhaps larger than practical for vascular entry to a subject in some embodiments. In larger vessels, the skilled artisan can opt for eccentric cutting to remove a larger region than the diameter of the cutter assembly without adding or exchanging the cutter for other larger tools for removal. The cutter can be biased off-center within the larger blood vessels to create added sweep.

Inducing a deflection into the systems and devices can be used to induce a "sweep", and this produces an effective "sweep diameter" to help the cutter 200 reach the lumen walls of large blood vessels and increase the centrifugal force realized by an excised tissue against the wall of the cutter, helping to ensure the tissue remains in the cutter head 220. As the deflection increases, the sweep increases and centrifugal force increases. Likewise, as the deflection decreases, the sweep decreases and centrifugal force decreases. As such, the sweep can be selected and designed into the systems and devices by the user to obtain the desired function of increasing reach and centrifugal force.

In some embodiments, the length of deflection, or sweep, can be referred to as the "deflection distance" and can be used to define the sweep that is induced in the thrombectomy device. The sweep can be obtained in any manner devisable by the skilled artisan and can be defined, in some embodiments, as the distance of the cutter head from the axis of rotation 270. The sweep can be defined, in some embodiments, as the deflection distance, which is the point on the leading edge 205 that is at the greatest distance from the axis of rotation 270.

In some embodiments, the sweep can be adjustable, such that the systems and devices can be equipped with a gauge on a handle of the systems and devices that indicate the sweep diameter obtained through an angle induced on a component of the system to create sweep. The inducing of a curve on a component of the system can be done in variety of methods, including those known to one of skill, such as through the use of a tendon to tension a component to induce the curve, or through the use of a material having a memory that contains the curve as a built-in shape during it's formation.

Cutting Heads can be Configured to Induce Sweep and Centrifugal Force

Sweep, So, can be designed into a cutting head by selecting an angle, ¢, between the head 220 and neck 225 of the cutter 200, providing a desired deflection distance from axis of rotation 270. The sweep increases the reach of the device within a vessel, or the diameter that can be reached by the cutting edge 205 of the tubular cutting head 220 of the device 200. In addition, the sweep can add centrifugal force to the cutting head, so that excised tissue receives additional force to aid in it's retention in the cutter head 220. In some embodiments, the sweep, So, can be easily estimated using the equation $So = L_D \sin \phi$. The sweep adds a "deflection distance" of the cutting edge 205 from the axis of rotation 270, where the sweep is 0 where $\phi = 0°$, and the sweep is a maximum of $L_D$, the length of the deflected portion of the cutting device, where $\phi = 90°$.

Figure 2H:
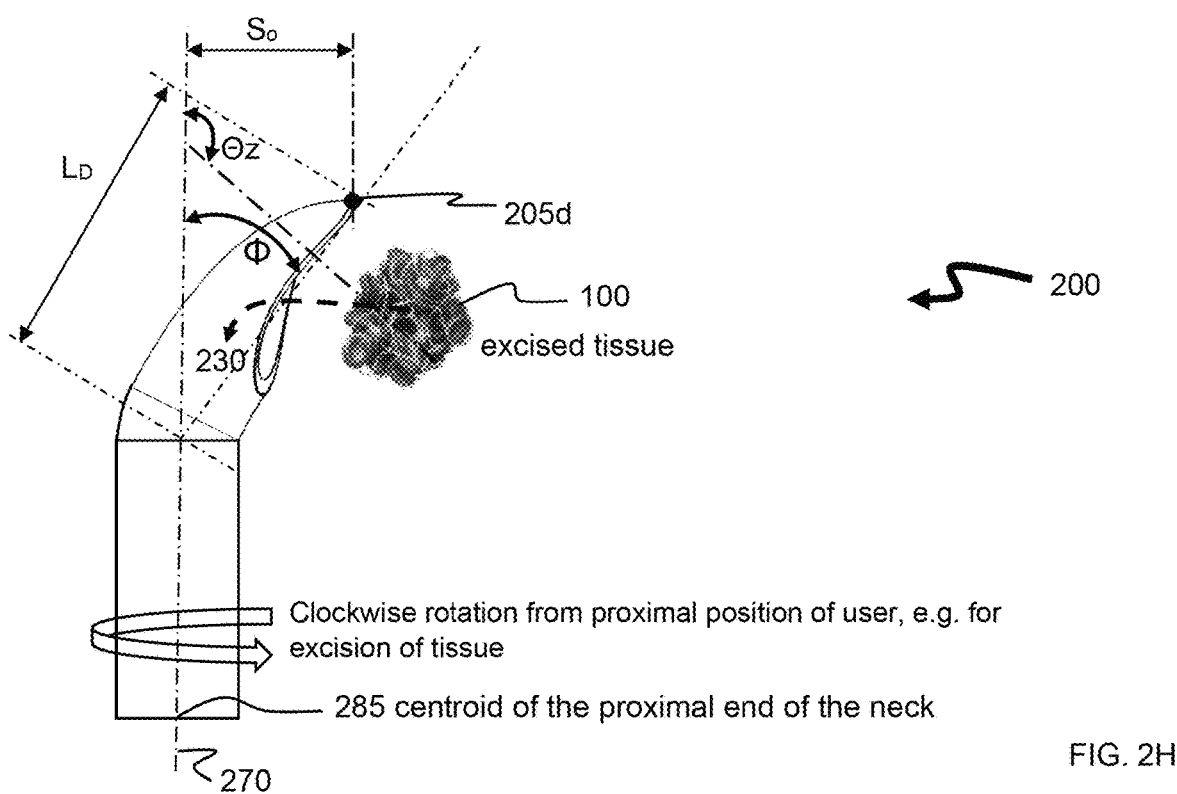

FIG. 2H illustrates how sweep can be introduced to a cutter 200 by inducing an angle, $\phi$, between the neck 225 and the head 220, in some embodiments. Introduction of sweep increases the reach of the cutting surface within a vessel, as well as introduce an addition of centrifugal force to help retain an excised tissue in the head 220 of the tubular cutter 200 after excision of the excised tissue from a target site in a subject. The angle, $\theta z$, can be selected to increase the reach of the cutter 200 and create a centrifugal force inside the mouth of the cutter to increase retention of the excised tissue in the head 220 after excision of the tissue from the subject, for example, excision of a thrombus from a vasculature. The leading edge 205 of the cutter 200 is further distanced from the axis of rotation 270, resulting in an increased reach of the leading edge 205, and increase in centrifugal force created during the rotation. The sweep in this embodiment can be defined as the deflection distance, So, which is the distance from the axis of rotation 270 to the point 205d, which is at the greatest distance from the axis of rotation 270.

The angle, $\theta z$, correlates with an angle, $\phi$, which creates the sweep in the head 220 of the cutter 200. In some embodiments, the angle, $\phi$, can range from 0° to 90°, from 1° to 90°, from 2° to 90°, from 3° to 90°, from 4° to 90°, from 5° to 90°, from 6° to 90°, from 7° to 90°, from 8° to 90°, from 9° to 90°, from 10° to 90°, from 15° to 90°, from 20° to 90°, from 25° to 90°, from 30° to 90°, from 35° to 90°, from 40° to 90°, from 45° to 90°, from 50° to 90°, or any amount or range therein in increments of 1°. In some embodiments, the angle, $\phi$, can range from 60° to 90°, from 70° to 90°, from 80° to 90°, or any amount or range therein in increments of 1°. In some embodiments, the angle, $\phi$, can range from 0° to 60°, from 5° to 60°, from 10° to 60°, from 15° to 60°, from 20° to 60°, from 25° to 60°, from 30° to 60°, from 35° to 60°, from 40° to 60°, from 45° to 60°, from 50° to 60°, from 55° to 60°, or any amount or range therein in increments of 1°. In some embodiments, the angle, $\phi$, can range from 0° to 45°, from 5° to 45°, from 10° to 45°, from 15° to 45°, from 20° to 45°, from 25° to 45°, from 30° to 45°, from 35° to 45°, from 40° to 45°, or any amount or range therein in increments of 1°. In some embodiments, the angle, $\phi$, can range from 5° to 30°, from 10° to 30°, from 15° to 30°, from 20° to 30°, from 25° to 30°, or any amount or range therein in increments of 1°. In some embodiments, the angle, $\phi$, can be 0°. In some embodiments, the angle, $\phi$, can be 0°, 1.0°, 2.0°, 3.0°, 4.0°, 5.0°, 6.0°, 7.0°, 8.0°, 9.0°, 10.0°, 11.0°, 12.0°, 13.0°, 14.0°, 15.0°, 16.0°, 17.0°, 18.0°, 19.0°, 20.0°, 21.0°, 22.0°, 23.0°, 24.0°, 25.0°, 26.0°, 27.0°, 28.0°, 29.0°, 30.0°, 31.0°, 32.0°, 33.0°, 34.0°, 35.0°, 36.0°, 37.0°, 38.0°, 39.0°, 40.0°, 41.0°, 42.0°, 43.0°, 44.0°, 50.0°, 55.0°, 60.0°, 65.0°, 70.0°, 75.0°, 80.0°, 85.0°, 90.0°, 95.0°, 100.0°, 105.0°, 110.0°, 115.0°, 120.0°, 125.0°, 130.0°, 135.0°, 140.0°, 145.0°, 150.0°, 155.0°, 160.0°, 165.0°, 170.0°, 175.0°, 180.0°, or any angle or range therein in 1° increments.

The thrombectomy devices drive the cutters with a flexible rotating shaft having a proximal end, a distal end, and a lumen, the tubular cutter operably connected with the distal end of the flexible rotating shaft. In some embodiments, the tubular cutter can be configured with

- a head having a distal end with a smooth, non-cutting surface, and a mouth with a rim and a z-axis, the rim having a cutting edge configured for removing a tissue from a target site within a blood vessel in a subject when rotating the tubular cutter within the blood vessel of the subject; and,
- a neck operably connected to the head, the neck having a throat with a central axis at an angle, $\theta z$, ranging from 0° to 180° from the z-axis of the mouth, the throat in communication with the lumen of the flexible rotating shaft for transport of the tissue away from the target site out of the subject.

The cutter 200 is attached to a flexible rotating shaft 305. In some embodiments, the cutter can be operably attached to the flexible rotating shaft using a friction fitting. In some embodiments, the flexible rotating shaft can be allowed slip on the base of the cutter when engaged with a thrombus and meeting a maximum torque limit.

In some embodiments, an outer sheath 307 or outer catheter 307 can be used for safely delivering the flexible rotating shaft 305 and cutting head 200 to a target site in a subject for tissue removal. In some embodiments, any outer sheath used can be used to deliver the flexible rotating shaft and cutting head and can be referred to as a "delivery sheath", "delivery catheter", "guide sheath", "guide catheter", and the like. In some embodiments, the delivery catheter has a bending stiffness that is greater than the bending stiffness of the flexible rotating shaft. In some embodiments, the combined stiffness of the flexible rotating shaft and the delivery catheter are minimized to help guide the flexible rotating shaft to the target site of the thrombus in the blood vessel.

The devices, systems, and methods taught herein can also include an annulus between the outer sheath and the flexible rotating shaft to allow for a step of introducing a fluid including, for example, a contrast agent, a drug, saline, or a combination thereof, to visualize the procedure, remove air, aid in clot removal, lubricate the spinning of the flexible rotating shaft in the outer sheath, or a combination thereof.

Flexible Rotating Shafts can be Configured to Induce Sweep and Centrifugal Force Another way to create sweep, or a deflection distance, is to induce an angle, θm, on the flexible rotating shaft. The angle, θm, can be induced on the flexibly rotating shaft 305 using a tendon, in some embodiments, or perhaps a memory curve, in some embodiments, and can range from 0° to 180°, or any amount or range therein in increments of 1°.

Figure 3A:
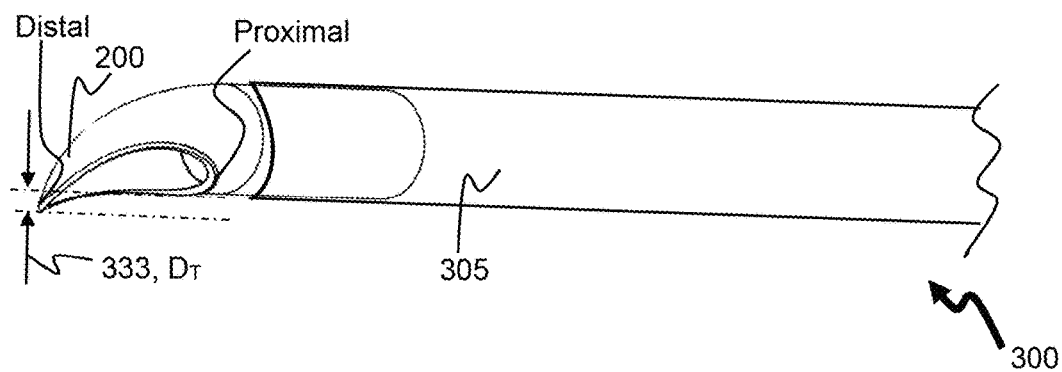
FIGS. 3A-3I illustrate thrombectomy tubular cutter systems, according to some embodiments.
Figure 3B:
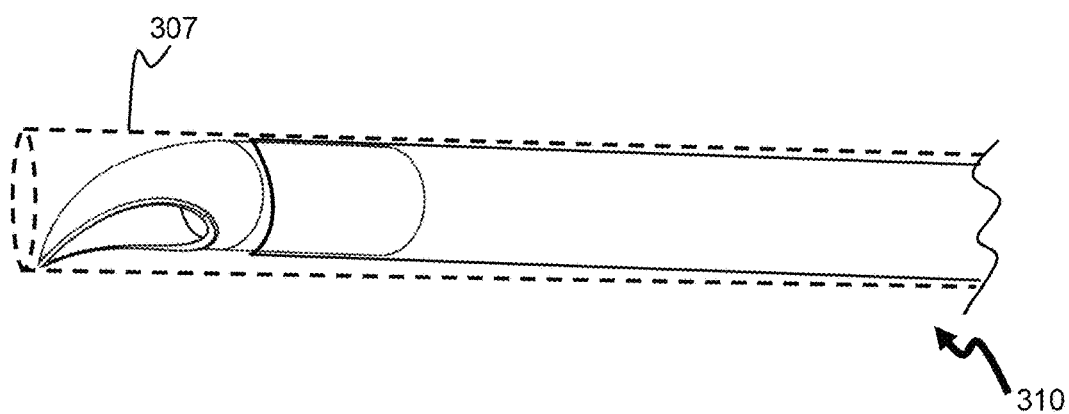
Figure 3C:
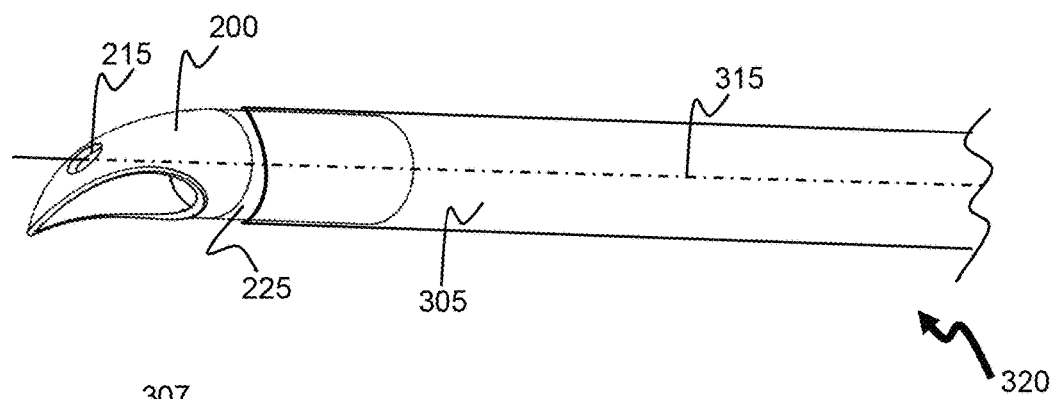
Figure 3D:
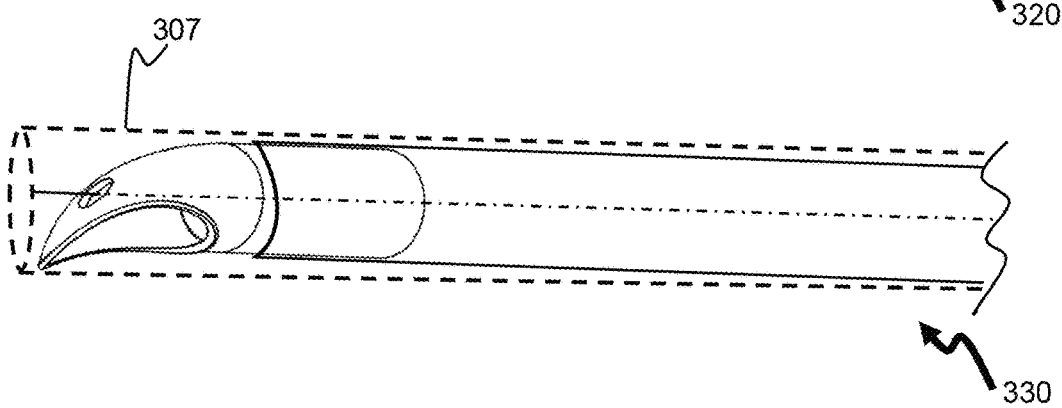

FIGS. 3A-3I illustrate thrombectomy tubular cutter systems, according to some embodiments. FIGS. 3A and 3B show thrombectomy tubular cutter systems 300,310 that do not include the optional guidewire port 215. FIG. 3A shows thrombectomy tubular cutter system 300 including the thrombectomy tubular cutter 200 operatively connected to the distal end of a flexible rotating shaft 305. FIG. 3B shows system 310 which includes system 300 with a delivery catheter 307. FIG. 3C shows thrombectomy tubular cutter system 320 including the thrombectomy tubular cutter 200 operatively connected to the distal end of a flexible rotating shaft 305, the thrombectomy tubular cutter 200 having guidewire port 215. FIG. 3D shows system 330 which includes system 320 with a delivery catheter 307. The neck of the thrombectomy tubular cutter 225 and the flexible rotating shaft 305 can share a central axis 315.

As shown in FIG. 3A, the tubular cutter 200 can be configured to have a talon-like shape, in some embodiments, in which the distal end of the rim extends a distance, $D_T$, from the proximal end of the rim at the top of the tubular cutter 200. In some embodiments, the distance, $D_T$, can range from 0.1 mm to 3.0 mm, from 0.2 mm to 3.0 mm, from 0.3 mm to 3.0 mm, from 0.3 mm to 3.0 mm, from 0.4 mm to 3.0 mm, from 0.5 mm to 3.0 mm, from 0.6 mm to 3.0 mm, from 0.7 mm to 3.0 mm, from 0.8 mm to 3.0 mm, from 0.9 mm to 3.0 mm from 1.0 mm to 3.0 mm, from 1.1 mm to 3.0 mm, from 1.2 mm to 3.0 mm, from 1.3 mm to 3.0 mm, from 1.4 mm to 3.0 mm, from 1.5 mm to 3.0 mm, from 1.6 mm to 3.0 mm, from 1.7 mm to 3.0 mm, from 1.8 mm to 3.0 mm, from 1.9 mm to 3.0 mm, from 2.0 mm to 3.0 mm, from 2.1 mm to 3.0 mm, from 2.2 mm to 3.0 mm, from 2.3 mm to 3.0 mm, from 2.4 mm to 3.0 mm, from 2.5 mm to 3.0 mm, from 2.6 mm to 3.0 mm, from 2.7 mm to 3.0 mm, from 2.8 mm to 3.0 mm, from 2.9 mm to 3.0 mm, or any range or amount therein in increments of 0.01 mm. In some embodiments, the distance, $D_T$, can range from 0.1 mm to 2.0 mm, from 0.2 mm to 2.0 mm, from 0.3 mm to 2.0 mm, from 0.3 mm to 2.0 mm, from 0.4 mm to 2.0 mm, from 0.5 mm to 2.0 mm, from 0.6 mm to 2.0 mm, from 0.7 mm to 2.0 mm, from 0.8 mm to 2.0 mm, from 0.9 mm to 2.0 mm, from 1.0 mm to 2.0 mm, from 1.1 mm to 2.0 mm, from 1.2 mm to 2.0 mm, from 1.3 mm to 2.0 mm, from 1.4 mm to 2.0 mm, from 1.5 mm to 2.0 mm, from 1.6 mm to 2.0 mm, from 1.9 mm to 2.0 mm, from 1.8 mm to 2.0 mm, from 1.9 mm to 2.0 mm, or any range or amount therein in increments of 0.01 mm. In some embodiments, the distance, $D_T$, can range from 0.1 mm to 1.0 mm, from 0.2 mm to 1.0 mm, from 0.3 mm to 1.0 mm, from 0.3 mm to 1.0 mm, from 0.4 mm to 1.0 mm, from 0.5 mm to 1.0 mm, from 0.6 mm to 1.0 mm, from 0.7 mm to 1.0 mm, from 0.8 mm to 1.0 mm, from 0.9 mm to 1.0 mm, or any range or amount therein in increments of 0.01 mm.

In some embodiments, the angle, θm, induced on the flexible rotating shaft can range from 0° to 180°, from 0° to 170°, from 0° to 160°, from 0° to 150°, from 0° to 140°, from 0° to 130°, from 0° to 120°, from 0° to 110°, from 0° to 100°, from 0° to 90°, from 0° to 45°, or any amount or range therein in increments of 1°. In some embodiments, the angle, θm, induced on the flexibly rotating shaft 305 can range from 0° to 30°, from 1° to 30°, from 2° to 30°, from 3° to 30°, from 4° to 30°, from 5° to 30°, 6° to 30°, from 7° to 30°, from 8° to 30°, from 9° to 30°, from 10° to 30°, from 15° to 30°, from 20° to 30°, from 25° to 30°, or any range or amount therein in increments of 1°. In some embodiments, the angle, θm, induced on the flexibly rotating shaft 305 can range from 0° to 45°, from 1° to 45°, from 2° to 45°, from 3° to 45°, from 4° to 45°, from 5° to 45°, 6° to 45°, from 7° to 45°, from 8° to 45°, from 9° to 45°, from 10° to 45°, from 15° to 45°, from 20° to 45°, from 25° to 45°, from 30° to 45°, from 35° to 45°, from 40° to 45°, from, or any range or amount therein in increments of 1°. In some embodiments, the angle, θm, induced on the flexibly rotating shaft 305 can range from 0° to 60°, from 1° to 60°, from 2° to 60°, from 3° to 60°, from 4° to 60°, from 5° to 60°, 6° to 60°, from 7° to 60°, from 8° to 60°, from 9° to 60°, from 10° to 60°, from 15° to 60°, from 20° to 60°, from 25° to 60°, from 30° to 60°, from 35° to 60°, from 40° to 60°, from 45° to 60°, from 50° to 60°, from 55° to 60°, or any range or amount therein in increments of 1°. In some embodiments, the angle, θm, induced on the flexibly rotating shaft 305 can range from 0° to 90°, from 1° to 90°, from 2° to 90°, from 3° to 90°, from 4° to 90°, from 5° to 90°, 6° to 90°, from 7° to 90°, from 8° to 90°, from 9° 90°, from 10° to 90°, from 15° to 90°, from 20° to 90°, from 25° to 90°, from 30° to 90°, from 35° to 90°, from 40° to 90°, from 45° to 90°, from 50° to 90°, from 55° to 90°, from 60° to 90°, from 65° to 90°, from 70° to 90°, from 75° to 90°, from 80° to 90°, from 85° to 90°, or any range or amount therein in increments of 1°. In some embodiments, the angle, θm, induced on the flexibly rotating shaft 305 can be 0°, 1.0°, 2.0°, 3.0°, 4.0°, 5.0°, 6.0°, 7.0°, 8.0°, 9.0°, 10.0°, 11.0°, 12.0°, 13.0°, 14.0°, 15.0°, 16.0°, 17.0°, 18.0°, 19.0°, 20.0°, 21.0°, 22.0°, 23.0°, 24.0°, 25.0°, 26.0°, 27.0°, 28.0°, 29.0°, 30.0°, 31.0°, 32.0°, 33.0°, 34.0°, 35.0°, 36.0°, 37.0°, 38.0°, 39.0°, 40.0°, 41.0°, 42.0°, 43.0°, 44.0°, 50.0°, 55.0°, 60.0°, 65.0°, 70.0°, 75.0°, 80.0°, 85.0°, 90.0°, 95.0°, 100.0°, 105.0°, 110.0°, 115.0°, 120.0°, 125.0°, 130.0°, 135.0°, 140.0°, 145.0°, 150.0°, 155.0°, 160.0°, 165.0°, 170.0°, 175.0°, 180.0°, or any angle or range therein in 1° increments.

As such, where there is an angle induced in the flexible rotating shaft, the outer sheath can be designed to straighten the flexible rotating shaft for delivery into a subject. In some embodiments, the outer sheath can be referred to as a "straightening-sheath", "straightening-catheter", and the like, as well as "delivery sheath", "delivery catheter", "guiding sheath", "guiding catheter", and the like. In some embodiments, the straightening catheter can have a bending stiffness that is the same, or similar to, the bending stiffness of the flexible rotating shaft.

Figure 3E:
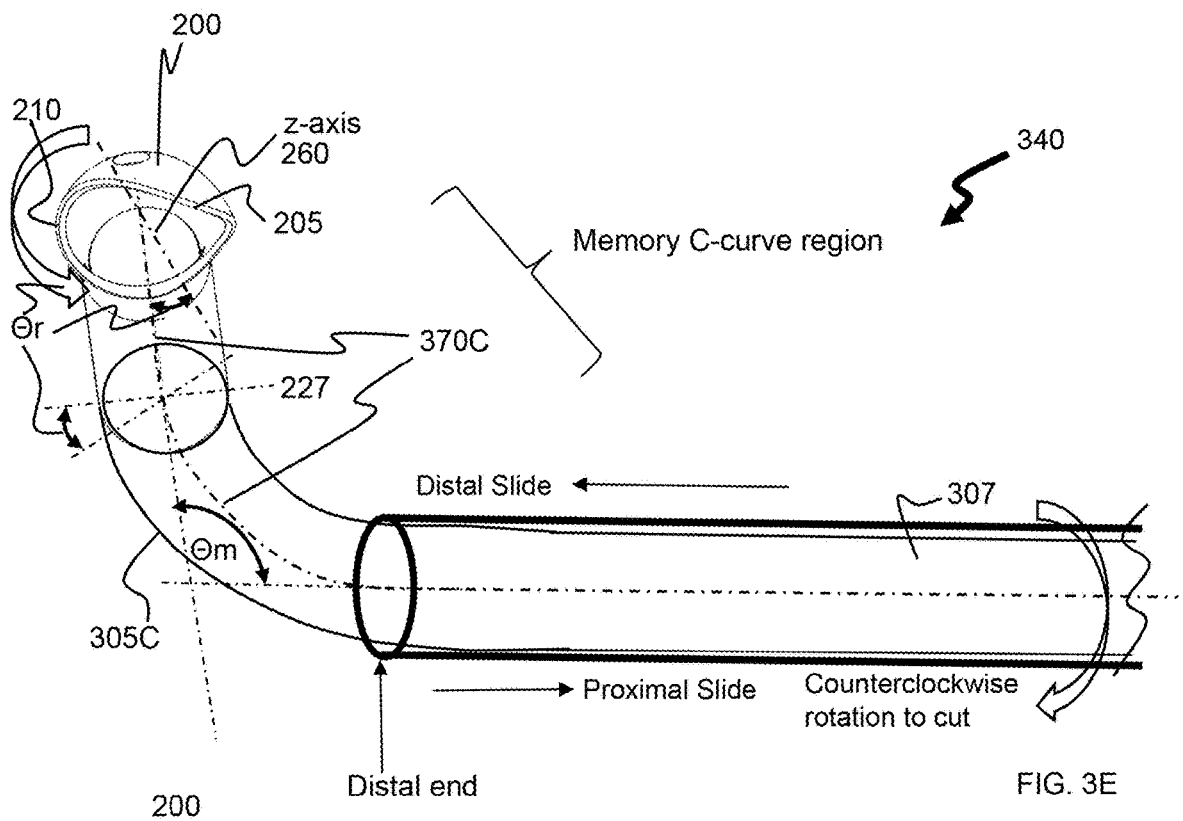

FIG. 3E shows a memory-shaft system 340 which includes a straightening-catheter 307 that is slidably translational over a memory-shaped flexible rotating shaft 305C. In this embodiment the flexible rotating shaft has a memory C-curve with an angle, θm, which is pre-shaped and elastic, and curved axis 370C that lies on a plane shared by the curve in the curved axis 370C. Due to the placement of the cutting edge 205, the device shown in FIG. 3E requires a counter-clockwise rotation to cut, from the proximal perspective of the person using the device.

The straightening-sheath has the function of straightening the memory C-curve of the memory-shaped rotating shaft 305C for delivery into a blood vessel of a subject. The straightening-sheath/catheter 307 has a proximal end (not shown) and a distal end. A distal slide of the straightening-sheath/catheter 307 from a position in which the distal end of the straightening-sheath/catheter 307 is proximal to the induced angle to gradually removes curvature from the C-curve. Likewise, a proximal slide of the straightening-sheath/catheter 307 from a position in which the distal end of the straightening-sheath/catheter 307 is distal to the memory C-curve gradually re-establishes curvature to the C-curve.

A braid-pattern construction can be used, in some embodiments, to achieve a desired material strength in the delivery catheter, flexible rotating shaft, or a combination thereof. In some embodiments, a spiral pattern construction can be used to achieve a desired material strength in the delivery catheter, flexible rotating shaft, or a combination thereof. In some embodiments, the straightening-sheath can include a braid-pattern construction which can be fabricated using any material known to be suitable to the skilled artisan. The braid-pattern construction, for example, can be selected to include any sort of braiding material deemed acceptable by one of skill for the intended use. For example, the braid-pattern or the spiral pattern can be include use of a metal, a polymer braiding, a fiber, or a combination thereof. An suitable medical grade material known to be suitable to the skilled artisan can be used.

Figure 3F:
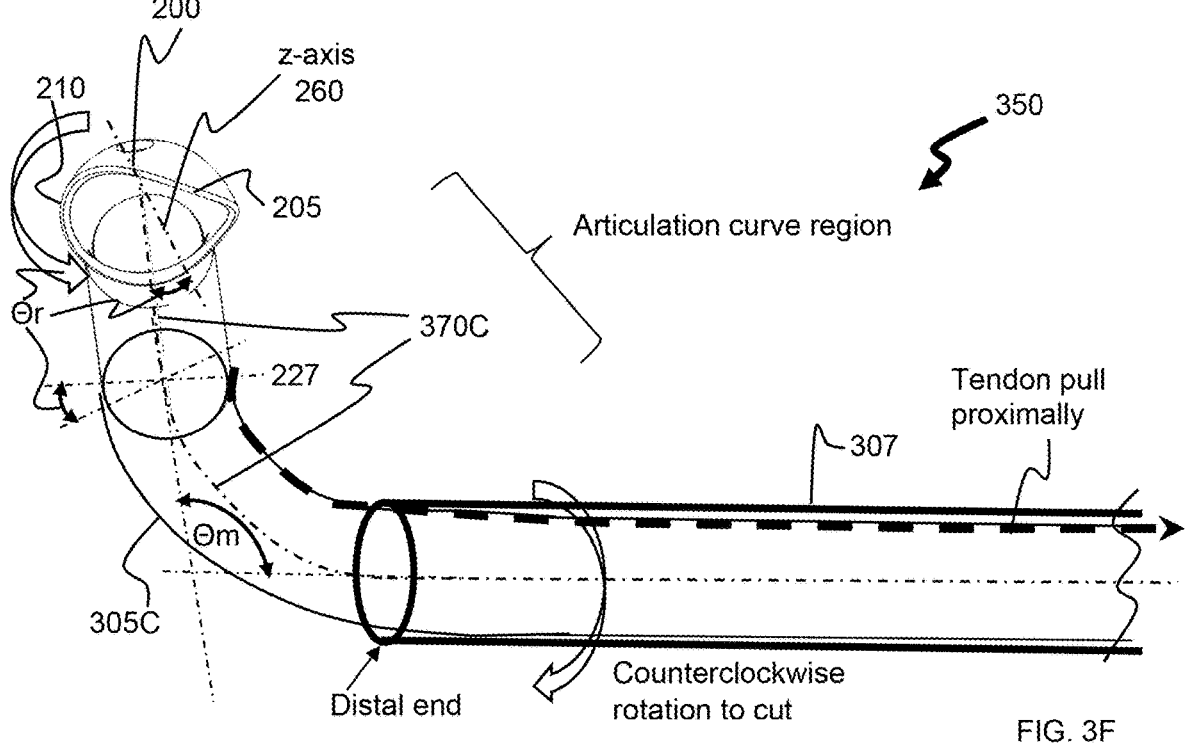

FIG. 3F shows a tendon-shaft system 350 which includes inducing a curve with angle, θm, on the flexible rotating shaft by applying tension to a tendon that integrated with the flexible rotating shaft, according to some embodiments. In some embodiments, the angle, θm, is induced on the flexible rotating shaft by the tendon can be straightened by releasing the tension on the tendon. In some embodiments, the angle, θm, is induced on the flexible rotating shaft can be straightened by pushing the tendon distally. In some embodiments, the angle, θm, is induced on the flexible rotating shaft can be straightened using a straightening catheter 307 that is slidably translational over the flexible rotating shaft 305C which, in this embodiment has a curve on curved axis 370C that lies on a plane shared by the curve.

Regardless of how the angle, θm, may be induced on the flexible rotating shaft, the tubular cutter 200 can have it's z-axis 260 rotated at an angle, θr, from an orthogonal position of the z-axis with respect to the plane, maintaining an orthogonal relationship with curved axis 370C, such that the cutting edge 205 leads the trailing edge 210 in the amount of the angle, θr, relative to the plane upon which the curved axis 370C lies. To clarify, the rotation of the cutter 200 to open the mouth to the target site is a rotating of the median plane 227 away from the plane shared by the curve in the deflection, where θr=0 is where the median plane 227 is coincident with the plane shared by the axis of the curve formed by the deflection. A rotation of θr>0 is a rotation of the median plane away from it's coincident relationship with the plane shared by the axis of the curve formed by the deflection, and the rotation of θr>0 functions to open the mouth of the head 220 toward the target site.

The amount of the angle θr is 0° where the position of the z-axis 260 is orthogonal to the plane upon which the curved axis 370C lies. The angle increases as the z-axis 260 is rotated relative to the 0° orthogonal position of the z-axis with respect to the plane, while maintaining an orthogonal relationship with curved axis 370C. As the angle increases the cutting edge 205 leads the trailing edge 210 in the amount of the angle θr. In some embodiments, the angle θr can range from 1° to 90°, from 2° to 90°, from 3° to 90°, from 4° to 90°, from 5° to 90°, 6° to 90°, from 7° to 90°, from 8° to 90°, from 9° 90°, from 10° to 90°, from 15° to 90°, from 20° to 90°, from 25° to 90°, from 30° to 90°, from 35° to 90°, from 40° to 90°, from 45° to 90°, from 50° to 90°, from 55° to 90°, from 60° to 90°, or any range or amount therein in increments of 1°. In some embodiments, the angle θr can range from 1° to 60°, from 2° to 60°, from 3° to 60°, from 4° to 60°, from 5° to 60°, 6° to 60°, from 7° to 60°, from 8° to 60°, from 9° to 60°, from 10° to 60°, from 15° to 60°, from 20° to 60°, from 25° to 60°, from 30° to 60°, from 35° to 60°, from 40° to 60°, from 45° to 60°, from 50° to 60°, from 55° to 60°, or any range or amount therein in increments of 1°. In some embodiments, the angle θr can range from 1° to 45°, from 2° to 45°, from 3° to 45°, from 4° to 45°, from 5° to 45°, 6° to 45°, from 7° to 45°, from 8° to 45°, from 9° 45°, from 10° to 45°, from 15° to 45°, from 20° to 45°, from 25° to 45°, from 30° to 45°, from 35° to 45°, from 40° to 45°, or any range or amount therein in increments of 1°. In some embodiments, the angle θr can range from 1° to 45°, from 2° to 40°, from 3° to 35°, from 4° to 30°, from 5° to 25°, 5° to 45°, from 5° to 40°, from 5° to 35°, from 5° to 30°, from 10° to 45°, 10° to 40°, from 10° to 35°, from 10° to 30°, from 10° to 25°, from 15° to 45°, 15° to 40°, from 15° to 35°, from 15° to 30°, from 15° to 25°, or any range or amount therein in increments of 1°. In some embodiments, the angle θr can be 1.0°, 2.0°, 3.0°, 4.0°, 5.0°, 6.0°, 7.0°, 8.0°, 9.0°, 10.0°, 11.0°, 12.0°, 13.0°, 14.0°, 15.0°, 16.0°, 17.0°, 18.0°, 19.0°, 20.0°, 21.0°, 22.0°, 23.0°, 24.0°, 25.0°, 26.0°, 27.0°, 28.0°, 29.0°, 30.0°, 31.0°, 32.0°, 33.0°, 34.0°, 35.0°, 36.0°, 37.0°, 38.0°, 39.0°, 40.0°, 41.0°, 42.0°, 43.0°, 44.0°, 45.0°, 55°, 60°, 65°, 70°, 75°, 80°, 85°, 90°, or any range or amount therein in increments of 1°.

Figure 3G:
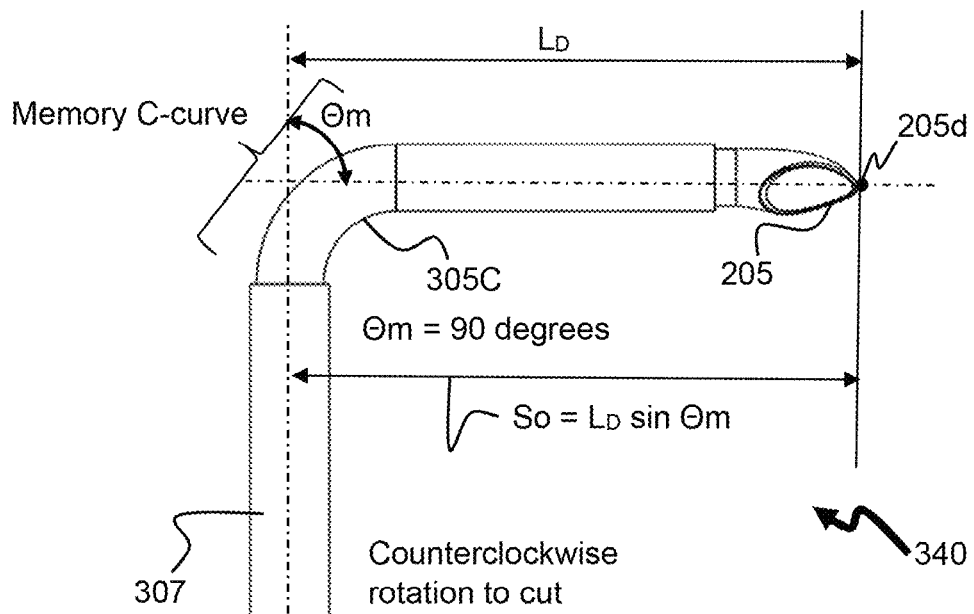
Figure 3H:
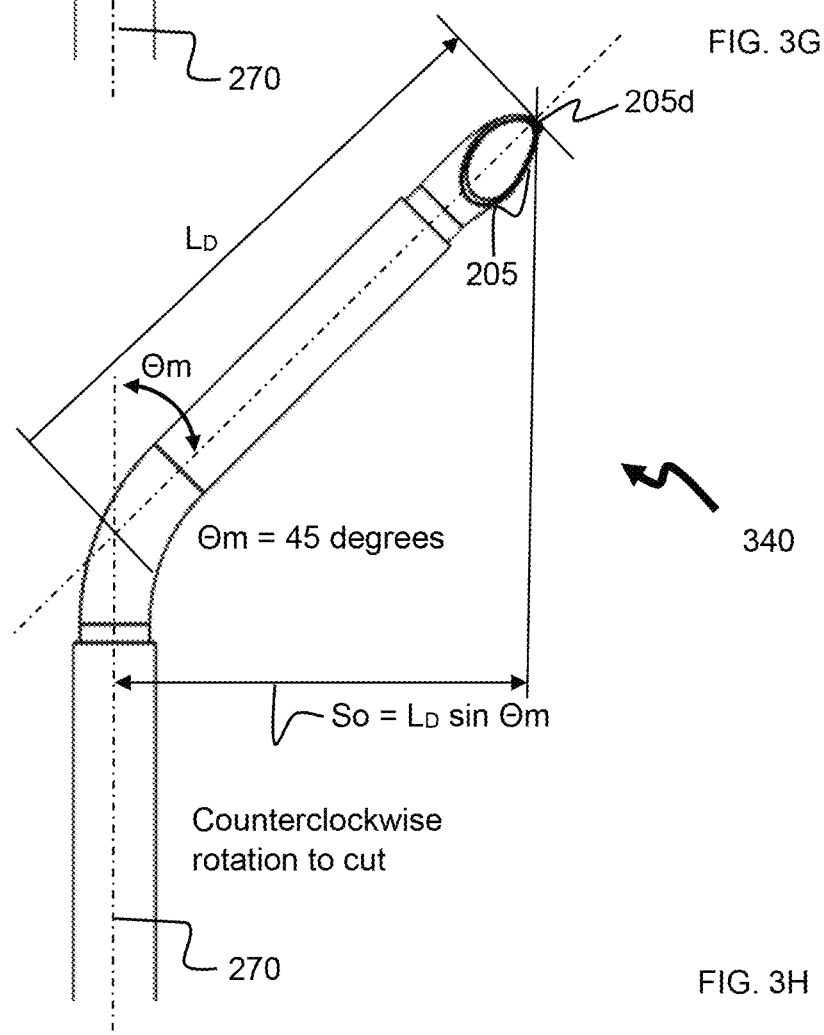

FIGS. 3G and 3H show the angle, θm, induced as the memory curve on the flexibly rotating shaft 305 memory-shaft system 340, in some embodiments. Due to the placement of the cutting edge 205, the device shown in FIG. 3G requires a counterclockwise rotation to cut, from the perspective of the person using the device. In FIG. 3G, the angle, θm, induced as the memory curve on the flexibly rotating shaft 305 memory-shaft system 340 can range from 0° to 180°, from 0° to 90°, from 90° to 180°, from 5° to 45°, from 10° to 45°, from 15° to 30°, from 20° to 60°, from 25° to 55°, from 30° to 45°, from 10° to 120°, from 20° to 120°, from 25° to 120°, from 30° to 120°, from 35° to 120°, from 40° to 120°, from 45° to 120°, from 10° to 110°, from 20° to 110°, from 25° to 110°, from 30° to 110°, from 35° to 110°, from 40° to 110°, from 45° to 110°, from 10° to 100°, from 20° to 100°, from 25° to 100°, from 30° to 100°, from 35° to 100°, from 40° to 100°, from 45° to 100°, from 10° to 90°, from 20° to 90°, from 25° to 90°, from 30° to 90°, from 35° to 90°, from 40° to 90°, from 45° to 90°, from 50° to 90°, from 55° to 90°, from 60° to 90°, from 65° to 90°, from 70° to 90°, from 75° to 90°, from 80° to 90°, or any range therein in increments of 1°. In some embodiments, the angle, θm, between the central axis of the neck and the z-axis of the mouth can be 10°, 15°, 20°, 25°, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, 150°, 155°, 160°, 165°, 170°, 175°, 180°, or any angle, θm, therein in 1° increments.

The angle, θm, deflects a distal portion of the thrombectomy device, the distal portion beginning at the apex of the angle formed by the memory C-curve. As can be seen from FIGS. 3G and 3H, the angle, θm, in some embodiments, can be used to provide a "sweep" or a "deflection distance" of the cutting edge 205 from the axis of rotation 270. The sweep, So, can be designed by selection of the angle, θm, of the memory C-curve, or by selection of the angle, θm, of the angle induced by a tendon, to provide a desired deflection distance from axis of rotation 270. The sweep increases the reach of the device within a vessel, or the diameter that can be reached by the cutting edge 205 of the tubular cutting head 220 of the device 200. The sweep in FIGS. 3G and 3H is the deflection distance, So, which is measured from the axis of rotation 270 to the point 205d on the leading edge 205, because the point 205d is at the greatest distance from the axis of rotation 270. The sweep can be easily estimated using So=$L_D$ sin θm, where the sweep is 0 where θm=0°, and the sweep is a maximum of $L_D$, the length of the deflected portion of the cutting device, where θm=90°.

Figure 3I:
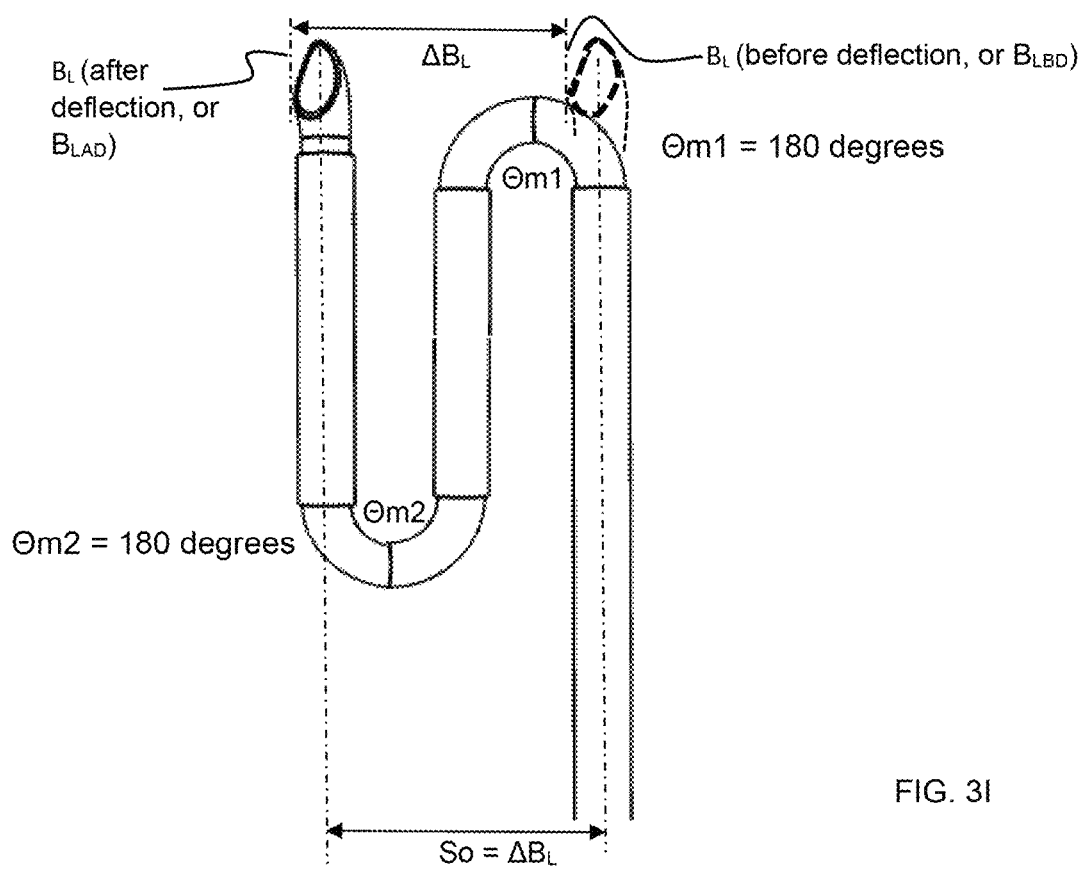

It should be appreciated that the sweep facilitates the use of the thrombectomy devices in larger vasculature. As such, any method of obtaining sweep to extend the reach of the cutter and add centrifugal force is contemplated in the embodiments. For example, more than one angle, θm, can be used to deflect a flexible rotating shaft. In some embodiments, the memory curve can be S-shaped, including an angle, θm1, and an angle, θm2, and the total sweep, So, is the total effect of the angle, θm1, and the angle, θm2, on the deflection distance. FIG. 3I provides an illustration of such an S-curve. It should be appreciated that although estimated deflection distances using So=$L_D$ sin θm can be fairly accurate where θm is 90° or less, these estimates start to become less accurate as θm increases above 90°, because the curve in the angle due to the physicality of the flexible rotating shaft introduces error. Moreover, the calculation is not useful at all for FIG. 3I, as the calculation of [So1=$L_D$ sin θm1]+ [So2=$L_D$ sin θm2]=0 where θm1 and θm2 are both 180°, and this is clearly not the case, as the curve in the combined angles due to the physicality of the flexible rotating shaft actually creates the deflection distance.

The teachings provided herein include methods of creating a deflection distance, in which the configuration of a device taught herein deflects the leading edge of the cutter away from the axis of rotation. As can be seen, the deflection distance can be created using any manner devised by one of skill to deflect the leading edge away from the axis of rotation, so that a sweep that increases the cutting diameter of the cutter results. Just as $B_L$ is measured at the furthest point away from and normal to the axis of rotation on the leading edge, the deflection distance can be measured as Δ $B_L$=$B_L$ (after deflection, or $B_{LAD}$)–$B_L$ (before deflection, or $B_{LBD}$), Referring to FIG. 3I, for example, it can be seen that So=Δ$B_L$, in this embodiment. As such, in some embodiments, it can be seen that So=Δ$B_L$=sweep=deflection distance.

In some embodiments, the deflection distance can range from 0.1 mm-30.0 mm, from 0.2 mm-30.0 mm, from 0.3 mm-30.0 mm, from 0.4 mm-30.0 mm, from 0.5 mm-30.0 mm, from 1.0 mm-30.0 mm, from 2.0 mm-30.0 mm, from 3.0 mm-30.0 mm, from 4.0 mm-30.0 mm, from 5.0 mm-30.0 mm, from 6.0 mm-30.0 mm, from 7.0 mm-30.0 mm, from 8.0 mm-30.0 mm, from 9.0 mm-30.0 mm, from 10.0 mm-30.0 mm, from 11.0 mm-30.0 mm, from 12.0 mm-30.0 mm, from 13.0 mm-30.0 mm, from 14.0 mm-30.0 mm, from 15.0 mm-30.0 mm, from 16.0 mm-30.0 mm, from 17.0 mm-30.0 mm, from 18.0 mm-30.0 mm, from 19.0 mm-30.0 mm, or any range or amount therein in increments of 0.1 mm. In some embodiments, the deflection distance can range from 0.1 mm-20.0 mm, from 0.2 mm-20.0 mm, from 0.3 mm-20.0 mm, from 0.4 mm-20.0 mm, from 0.5 mm-20.0 mm, from 1.0 mm-20.0 mm, from 2.0 mm-20.0 mm, from 3.0 mm-20.0 mm, from 4.0 mm-20.0 mm, from 5.0 mm-20.0 mm, from 6.0 mm-20.0 mm, from 7.0 mm-20.0 mm, from 8.0 mm-20.0 mm, from 9.0 mm-20.0 mm, from 10.0 mm-20.0 mm, from 11.0 mm-20.0 mm, from 12.0 mm-20.0 mm, from 13.0 mm-20.0 mm, from 14.0 mm-20.0 mm, from 15.0 mm-20.0 mm, from 16.0 mm-20.0 mm, from 17.0 mm-20.0 mm, from 18.0 mm-20.0 mm, from 19.0 mm-20.0 mm, or any range or amount therein in increments of 0.1 mm. In some embodiments, the deflection distance can range from 0.5 mm-19.0 mm, from 1.0 mm-18.0 mm, from 2.0 mm-17.0 mm, from 3.0 mm-16.0 mm, from 4.0 mm-15.0 mm, from 5.0 mm-14.0 mm, from 6.0 mm-13.0 mm, from 7.0 mm-12.0 mm, from 8.0 mm-10.0 mm, or any range or amount therein in increments of 0.1 mm. In some embodiments, the deflection distance can be 0.1 mm, 0.2 mm, 0.3 mm, 0.4 mm, 0.5 mm, 1.0 mm, 2.0 mm, 3.0 mm, 4.0 mm, 5.0 mm, 6.0 mm, 7.0 mm, 8.0 mm, 9.0 mm, 10.0 mm, 11.0 mm, 12.0 mm, 13.0 mm, 14.0 mm, 15.0 mm, 16.0 mm, 17.0 mm, 18.0 mm, 19.0 mm, 20.0 mm, 21.0 mm, 22.0 mm, 23.0 mm, 24.0 mm, 25.0 mm, 26.0 mm, 27.0 mm, 28.0 mm, 29.0 mm, 30.0 mm, or any amount or range therein in increments of 0.1 mm.

Component Characteristics

The components of the devices and systems can be designed to have desirable characteristics. The desirable characteristics can be obtained from material selection and the design of the materials to obtain a desired range of functions.

In some embodiments, the flexible rotating shaft may be fabricated from a polymer tube, a metal tube with slots for flexibility (for example, a type 304 stainless steel tube or the like), or a composite of polymer and metal. For a composite material, a metal coil, mesh, or braid can be laminated, using perhaps a polymer coating or molecular coating, for increased corrosion resistance, contamination control, and heat stability. In some embodiments, the polymer may be PEBAX, nylon, polyimide, PEEK, polyethylene, fluoropolymer (PTFE, ETFE, PVDF, FEP), or any combination thereof. The single molecule may be fluoro silane, in some embodiments. The dimensions of the tube may depend at least partially on the intended use of the thrombectomy device/apparatus/system.

It should be appreciated that, in some embodiments, the flexible, rotating shaft 305 can have a bending stiffness that is suitable for directing the cutting head to the target sight of the thrombus in a blood vessel. In some embodiments, the flexible, rotating shaft 305 can have an axial stiffness that is sufficient to transfer an axial force to the tubular cutter during operation of the thrombectomy device. Likewise, In some embodiments, the flexible, rotating shaft 305 can have a torsional stiffness that is sufficient to transfer torque from the proximal end of the flexible rotating shaft to the distal end of the flexible rotating shaft to rotate the tubular cutter during operation of the thrombectomy device.

The sheath/delivery catheter 307 can be "relatively stiff" compared to the flexible rotating shaft, in some embodiments, in that it can be designed to be substantially stiffer than the flexible rotating shaft 305C. As such, the sheath/delivery catheter 307 is relatively stiffer than the flexible rotating shaft 305C, such that a tendon (bold dashed line) can be pulled proximally to induce the memory curve region. The sheath/delivery catheter 307 can have the same or similar stiffness compared to the flexible rotating shaft.

One of skill will appreciate that control of the flexural stiffness of the device will allow additional control of the cutter to the user of the device. As such, in some embodiments, any device taught herein can be designed to obtain a desired amount of deflection to direct the cutter a desired surface of the vascular lumen wall. One of skill will appreciate that there are methods to vary the flexural stiffness of the flexible rotating shaft, the delivery sheath, or a combination thereof. The stiffness or flexibility of the components may be adjusted, for example, by varying the composition and/or structure of materials. In some embodiments, to increase flexural stiffness, the filaments on the flexible rotating shaft, the delivery sheath, or a combination thereof, can be bound together with stiffer material, or the flexural stiffness can be increased (or reduced) by increasing (or decreasing) the filament size.

In addition to providing the proper flexural stiffness and torsional stiffness for maneuverability and function, the devices also need the required axial tensile stiffness for a better response of the thrombectomy devices to push and pull. Axial tensile stiffness is the resistance to stretch or contraction of along the length of the component under axial loading and is in units of N/mm. Key components in the design, in some embodiments, include a desired axial tensile stiffness in the delivery sheath and the flexible rotating shaft.

The flexural stiffness of the delivery catheter could be similar to, equal to, or greater than the flexible rotating shaft, in some embodiments. The ratio of flexural stiffness of the flexible rotating shaft to the flexural stiffness of the delivery catheter can range from 0.03 to 1.0 in some embodiments, 0.03 to 0.30 in some embodiments, 0.05 to 0.25 in some embodiments, 0.06 to 0.30 in some embodiments, from 0.5 to 1.0, from 0.6 to 1.0, from 0.7 to 1.0, from 0.8 to 1.0, from 0.9 to 1.0, or any range or amount therein in increments of 0.01. In some embodiments, the ratio of flexural stiffness of the flexible rotating shaft to the flexural stiffness of the delivery catheter can be 0.10, 0.20, 0.30, 0.40, 0.40, 0.40, 0.40, 0.40, 0.40, 0.40 or any ratio or range therein in increments of 0.01. In some embodiments, however, the flexural stiffness of the delivery catheter is 2× 3×, or 4× greater than the flexural stiffness of the flexible rotating shaft, or any range or amount therein in increments of 0.1×.

In some embodiments, a straightening-sheath is merely configured to have a minimal stiffness suitable to straighten the flexible rotating shaft for delivery to a target site in a subject. In some embodiments, the force required to bend the straightening-sheath is greater than the force required to bend the flexible rotating shaft, for example, perhaps to bend memory-shaped C-curve portion of the flexible rotating shaft. In some embodiments, the force required to bend the straightening-sheath is greater than the force required to bend the flexible rotating shaft, and in some embodiments the memory C-curve, by 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, or any amount or range therein in amounts of 0.1%. In some embodiments, the force required to bend the straightening-sheath is greater than the force required to bend the flexible rotating shaft, and in some embodiments the memory C-curve, by a range of 1%-50%, 2%-50%, 3%-50%, 4%-50%, 5%-50%, 6%-50%, 7%, 8%-50%, 9%-50%, 10%-50%, 11%-50%, 12%-50%, 13%-50%, 14%-50%, 15%-50%, 16%-50%, 17%-50%, 18%-50%, 19%-50%, 20%-50%, 21%-50%, 22%-50%, 23%-50%, 24%-50%, 25%-50%, or any amount or range therein in amounts of 0.1 In some embodiments, the force required to bend the straightening-sheath is greater than the force required to bend the flexible rotating shaft, and in some embodiments the memory C-curve, can be 2×, 3×, or 4× greater than the force required to bend the memory-shaped C-curve, or any amount or range therein in amounts of 0.1×.

The stiffness of the straightening-sheath can affect the ability of the straightening-sheath to remove the memory-C-curve of the flexible rotating shaft, but it should be appreciated that the stiffness needs to be limited due to the adverse effects of the stiffness of the combination of device components on the friction applied to the vascular lumen wall. As such, it is desirable to minimize device stiffness to target a tissue location for treatment and direct the tubular head to the target area.

In some embodiments, a desirable stiffness of the straightening-sheath can range from 15 $Nmm^2$ to 900 $Nmm^2$, 30 $Nmm^2$ to 800 $Nmm^2$, from 20 $Nmm^2$ to 200 $Nmm^2$, 400 $Nmm^2$ to 800 $Nmm^2$, or any amount or range therein in increments of 1 $Nmm^2$. In some embodiments, a desirable stiffness of the straightening-sheath can be dependent on the location of the stiffness measurement along the sheath, for example, to add flexibility at a distal region of the sheath and a relative stiffness at a proximal region of the sheath, where the border between distal and proximal is at the midpoint of the sheath as defined by the length of the sheath in the subject during an interventional procedure. In some embodiments, a desired stiffness in a distal region of a straightening sheath can range from 20 $Nmm^2$ to 200 $Nmm^2$, from 30 $Nmm^2$ to 100 $Nmm^2$, or any amount or range therein in increments of 1 $Nmm^2$. In some embodiments, a desired stiffness in a proximal region of a sheath can range from 300 $Nmm^2$ to 900 $Nmm^2$, from 400 $Nmm^2$ to 800 $Nmm^2$, or any amount or range therein in increments of 1 $Nmm^2$. In some embodiments, a desired combined stiffness at any point on the thrombectomy device, whether in proximal or distal portion of the device, can be 10 $Nmm^2$, 20 $Nmm^2$, 30 $Nmm^2$, 40 $Nmm^2$, 50 $Nmm^2$, 60 $Nmm^2$, 70 $Nmm^2$, 80 $Nmm^2$, 90 $Nmm^2$, 100 $Nmm^2$, 200 $Nmm^2$, 300 $Nmm^2$, 400 $Nmm^2$, 500 $Nmm^2$, 600 $Nmm^2$, 700 $Nmm^2$, 800 $Nmm^2$, 900 $Nmm^2$, or any amount or range therein in increments of 1 $Nmm^2$.

The axial strength of the flexible rotating shaft, delivery catheter, or the combination thereof, is also a design feature. In some embodiments, the flexible rotating shaft, delivery catheter, or the combination thereof, can be configured to have a column strength suitable to withstand pushing into a subject without increasing the diameter of In some embodiments, the flexible rotating shaft, delivery catheter, or the combination thereof, to an undesirable amount. As such, In some embodiments, the flexible rotating shaft, delivery catheter, or the combination thereof, can be configured to have a column strength suitable to withstand pulling out of a subject without reducing the diameter of the flexible rotating shaft, delivery catheter, or the combination thereof, to an undesirable amount. In some embodiments, the undesirable amount of increase in diameter of the flexible rotating shaft, delivery catheter, or the combination thereof, upon pushing into a subject is less than 1%, less than 2%, less than 3%, less than 4%, less than 5%, less than 6%, less than 7%, less than 8%, less than 9%, less than 10%, less than 11%, less than 12%, less than 13%, less than 14%, less than 15%, less than 16%, less than 17%, less than 18%, less than 19%, less than 20%, or any amount or range therein in amounts of 0.1%; and, in some embodiments, the increase in diameter of the flexible rotating shaft, delivery catheter, or the combination thereof, upon pushing into a subject can range from 0%-20%, 1%-20%, 2%-20%, 3%-20%, 4%-20%, 5%-20%, 6%-20%, 7%-20%, 8%-20%, 9%-20%, 10%-20%, or any amount or range therein in amounts of 0.1%. In some embodiments, the undesirable amount of decrease in diameter of the flexible rotating shaft, delivery catheter, or the combination thereof, upon pulling out of a subject is less than 1%, less than 2%, less than 3%, less than 4%, less than 5%, less than 6%, less than 7%, less than 8%, less than 9%, less than 10%, less than 11%, less than 12%, less than 13%, less than 14%, less than 15%, less than 16%, less than 17%, less than 18%, less than 19%, less than 20%, or any amount or range therein in amounts of 0.1%; and, in some embodiments, the decrease in diameter of the flexible rotating shaft, delivery catheter, or the combination thereof, upon pulling out of a subject can range from 0%-20%, 1%-20%, 2%-20%, 3%-20%, 4%-20%, 5%-20%, 6%-20%, 7%-20%, 8%-20%, 9%-20%, 10%-20%, or any amount or range therein in amounts of 0.1%.

Generally speaking, in some embodiments, the outer diameter of the tubular cutter and/or flexible rotating shaft can range from 2.0 mm-10.0 mm, from 2.5 mm-9.5 mm, from 3.0 mm-9.0 mm, from 3.5 mm-8.5 mm, from 4.0 mm-8.0 mm, from 4.5 mm-7.5 mm, from 5.0 mm-7.0 mm, or any amount or range therein in increments of 0.1 mm. In some embodiments, the outer diameter of the tubular cutter can be 2.0 mm, 2.2 mm, 2.4 mm, 2.6 mm, 2.8 mm, 3.0 mm, 3.2 mm, 3.4 mm, 3.6 mm, 3.8 mm, 4.0 mm, 4.2 mm, 4.4 mm, 4.6 mm, 4.8 mm, 5.0 mm, 5.2 mm, 5.4 mm, 5.6 mm, 5.8 mm, 6.0 mm, 6.2 mm, 6.4 mm, 6.6 mm, 6.8 mm, 7.0 mm, 7.2 mm, 7.4 mm, 7.6 mm, 7.8 mm, 8.0 mm, 8.2 mm, 8.4 mm, 8.6 mm, 8.8 mm, 9.0 mm, 9.2 mm, 9.4 mm, 9.6 mm, 9.8 mm, 10.0 mm, or any amount or range therein in increments of 0.1 mm.

For example, in some variations the outer diameter of the tube may be limited to about 2.2 mm, while in other variations the outer diameter of the tube may be limited to about 1.6 mm, and others can range from as much as 2.0 mm to 10.0 mm, 3.0 mm to 9.0 mm, 4.0 mm to 8.0 mm, 5.0 mm to 7.0 mm, or any amount or range therein in increments of 0.1 mm. In some embodiments, the wall thickness of the tube may be limited to about 0.05 to 1 mm. In some embodiments, the wall thickness of the tube may be limited to 0.1 mm to 0.2 mm. In some embodiments, the overall length of the tube of the flexible rotating shaft may range from about 500 mm to 1500 mm (about 20 inches to about 60 inches), from about 500 mm to 1400 mm, from about 500 mm to 1300 mm, from about 500 mm to 1200 mm, from about 500 mm to 1100 mm, from about 500 mm to 1000 mm, or any amount or range therein in increments of 1 mm.

Figure 4A:
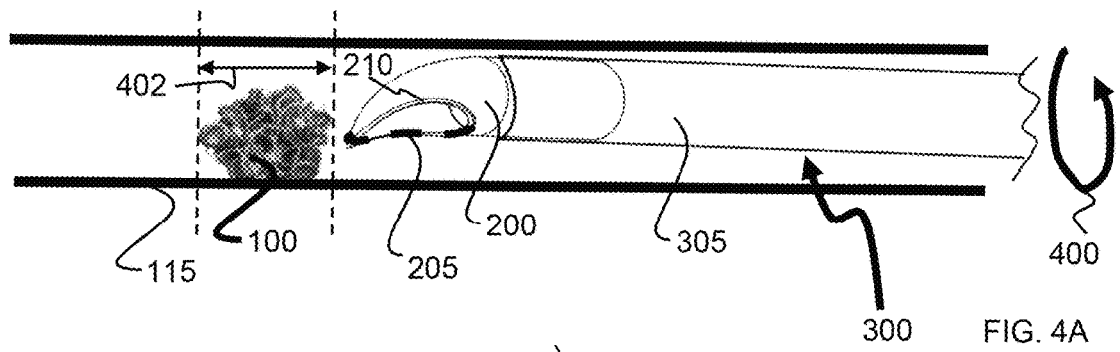
FIGS. 4A-4D illustrate the configuration of a rotating thrombectomy tubular cutter system for removing a thrombus, according to some embodiments.
Figure 4B:
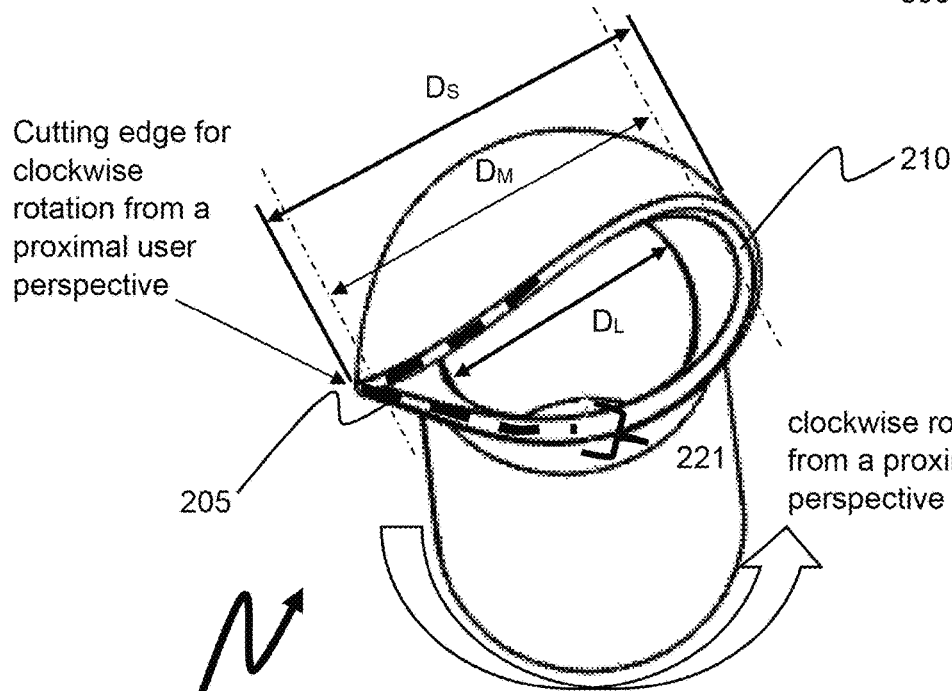

FIGS. 4A-4D illustrate the configuration of a rotating thrombectomy tubular cutter system for removing a thrombus, according to some embodiments. FIG. 4A shows system 300 approaching a target site 402 to rotate 400 the head of the thrombectomy tubular cutter 200 to remove thrombus 100 from within blood vessel 115. The rotating 400 of the head of the thrombectomy tubular cutter 200 can be in a clockwise direction, or counterclockwise direction, when viewed from a position that is proximal to the thrombus 100. The rotating 400 separates the thrombus 100 from the blood vessel 115, for example by tubular cutting the cutting edge 205 through the interface between the thrombus 100 and the luminal wall of the blood vessel 115. In some embodiments, the cutting edge 205 removes a portion of the thrombus 100 without contacting the luminal wall of the blood vessel 115 by cutting through the thrombus 100 to remove just a portion of the thrombus. After the rotating 400 and tubular cutting of the thrombus 100, the thrombus 100 is captured in the mouth 220 of the thrombectomy tubular cutter 200 for removal from the blood vessel 115. FIG. 4B shows the shape of the rim 221 of the mouth 220, having a diameter $D_S$, which can be any shape that will facilitate the tubular cutting of a thrombus within a blood vessel. The cutting edge 205 is positioned for a clockwise rotation, as seen from a user's position proximal to the head of the cutter, the cutting edge highlighted by the dashed-line in FIG. 4B.

One of skill should appreciate that the rim 221 of the mouth 220 can have any shape that facilitates thrombus removal, and often the shape can be undulating, helical, serrated, sinusoidal, straight, or some combination of such features. In some embodiments, all surfaces of the rim 221 can contact the same plane. However, in some embodiments, some surfaces of the rim 221 do not contact the same plane as other surfaces of the rim 221. In some embodiments only a select few surfaces of the rim 221 of the mouth 220 contact the same plane. For example, in some embodiments, only 2, 3, or 4 surfaces of the rim 221 of the mouth 220 contact the same plane.

FIG. 4B, for example, shows a rim 221 of the mouth 220 having an elliptical shape having an axis that is rotated counter clockwise from the axis of the lumen of the neck of the thrombectomy tubular cutter when viewed from a top-down perspective to the thrombectomy tubular cutter. Cutters with a rim 221 such as FIG. 4G can have only 2 surfaces that contact a plane that is parallel to a horizontal plane that dissects the thrombectomy device. This configuration results from the "helical" nature of the relative shapes of the cutting edge 205 and trailing edge 210. The cutting edge 205 is also designed for a clockwise rotation using the right-hand helical shape of the cutting edge 205, again viewed from a user's position proximal to the head of the cutter, the cutting edge shown by the dashed-line in FIG. 4B. On the contrary, a cutting edge for a counterclockwise rotation when viewed from a position proximal to the head of the cutter would have a left-hand helical shape.

Figure 4C:
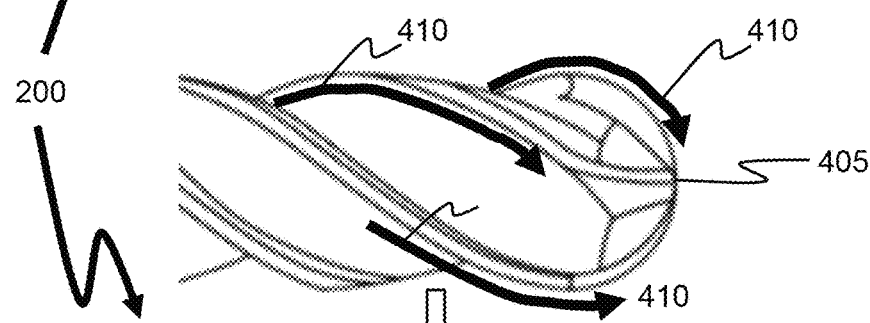
Figure 4D:
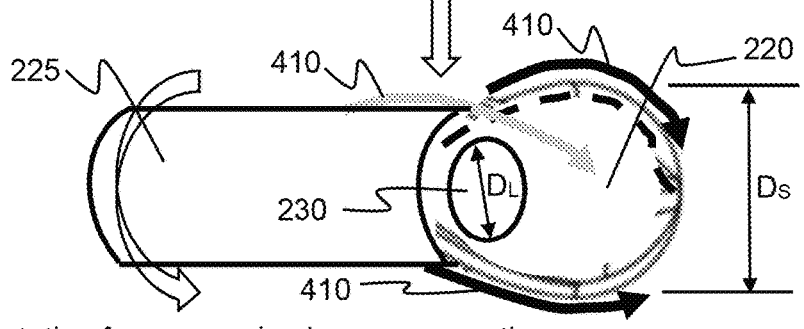

FIG. 4C shows how a right-hand helical drill bit can be used, in some embodiments, to create a thrombectomy tubular cutter 200. A drill bit can be created by selecting a surgical grade metal using well-known drill bit manufacturing techniques. The bit will be sized such that the distance between opposite flute edges matches the desired width, or diameter of the tubular cutter, $D_S$, of the thrombectomy tubular cutter 200. The point 405 of the bit can serve as the distal end of the thrombectomy tubular cutter 200, and the body of the bit can be ground to form a mouth 220 for the thrombectomy tubular cutter 200. The helical shapes of the flutes 410 can be ground to form the rim 221 of the mouth 220, where cutting edge 205 and trailing edge 210 are formed by the flutes of the bit. The shank (not shown) of the bit can be bored-out to create a lumen 230 having a desired diameter, $D_L$, in the neck of the thrombectomy tubular cutter 200. FIG. 4D illustrates the transformation of the drill bit shown in FIG. 4C. As noted above, a right-hand helical bit would be used for a clockwise rotation when viewed from a position proximal to the head of the cutter, whereas a left-hand helical bit (not shown) would be used for a counterclockwise rotation when viewed from a position proximal to the head of the cutter.

Mouth Orientation can Add to Sweep by Providing Bias

The inlet of the mouth has a major axis that can oriented at an angle, $\theta_B$, from the orientation of the central axis of the neck of the tubular cutter. The angle, $\theta_B$, can be measured on a horizontal plane that bisects the central axis of the neck of the tubular cutter to separate the top of the tubular cutter from the bottom of the tubular cutter.

Figure 5A:
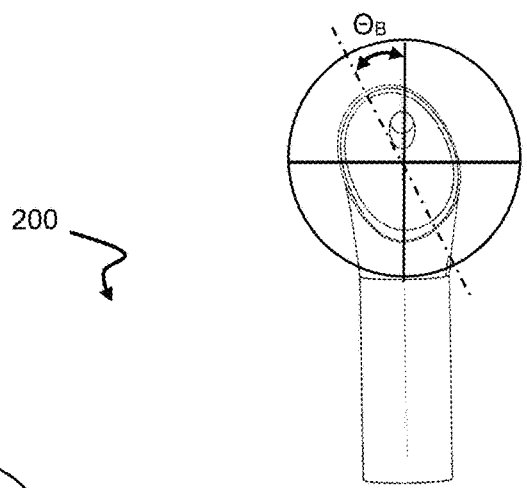
FIGS. 5A-5L illustrate a variety of mouth shapes and sweep offsets, according to some embodiments.

FIGS. 5A-5L illustrate a variety of mouth shapes and sweep offsets, according to some embodiments. It should be appreciated that any mouth shape that facilitates the removal of a thrombus from the luminal wall of a vessel can be used. As shown in FIG. 5A, the rim 221 of the mouth 220 can be elliptical with an axis (a major axis) and a mathematical center point.

In some embodiments, the major axis of the ellipse can be rotated about the mathematical center point. In some embodiments, the inlet of the mouth has a major axis that is oriented at an angle, $\theta_B$, from the orientation of the central axis of the neck of the tubular cutter, wherein $\theta_B$ is measured on a horizontal plane that bisects the central axis of the neck of the tubular cutter to separate the top of the tubular cutter from the bottom of the tubular cutter.

In some embodiments, the angle or rotation of the mouth, $\theta_B$, can range from 1° to 90°, from 2° to 90°, from 3° to 90°, from 4° to 90°, from 5° to 90°, 6° to 90°, from 7° to 90°, from 8° to 90°, from 9° 90°, from 10° to 90°, from 15° to 90°, from 20° to 90°, from 25° to 90°, from 30° to 90°, from 35° to 90°, from 40° to 90°, from 45° to 90°, from 50° to 90°, from 55° to 90°, from 60° to 90°, or any range or amount therein in increments of 1°. In some embodiments, the angle, $\theta_B$, can range from 1° to 60°, from 2° to 60°, from 3° to 60°, from 4° to 60°, from 5° to 60°, 6° to 60°, from 7° to 60°, from 8° to 60°, from 9° to 60°, from 10° to 60°, from 15° to 60°, from 20° to 60°, from 25° to 60°, from 30° to 60°, from 35° to 60°, from 40° to 60°, from 45° to 60°, from 50° to 60°, from 55° to 60°, or any range or amount therein in increments of 1°. In some embodiments, the angle, $\theta_B$, can range from 1° to 45°, from 2° to 45°, from 3° to 45°, from 4° to 45°, from 5° to 45°, 6° to 45°, from 7° to 45°, from 8° to 45°, from 9° 45°, from 10° to 45°, from 15° to 45°, from 20° to 45°, from 25° to 45°, from 30° to 45°, from 35° to 45°, from 40° to 45°, or any range or amount therein in increments of 1°. In some embodiments, the angle, $\theta_B$, can range from 1° to 45°, from 2° to 40°, from 3° to 35°, from 4° to 30°, from 5° to 25°, 5° to 45°, from 5° to 40°, from 5° to 35°, from 5° to 30°, from 10° to 45°, 10° to 40°, from 10° to 35°, from 10° to 30°, from 10° to 25°, from 15° to 45°, 15° to 40°, from 15° to 35°, from 15° to 30°, from 15° to 25°, or any range or amount therein in increments of 1°. In some embodiments, the angle, $\theta_B$, can be 1.0°, 2.0°, 3.0°, 4.0°, 5.0°, 6.0°, 7.0°, 8.0°, 9.0°, 10.0°, 11.0°, 12.0°, 13.0°, 14.0°, 15.0°, 16.0°, 17.0°, 18.0°, 19.0°, 20.0°, 21.0°, 22.0°, 23.0°, 24.0°, 25.0°, 26.0°, 27.0°, 28.0°, 29.0°, 30.0°, 31.0°, 32.0°, 33.0°, 34.0°, 35.0°, 36.0°, 37.0°, 38.0°, 39.0°, 40.0°, 41.0°, 42.0°, 43.0°, 44.0°, 45.0°, 55.0°, 60.0°, 65.0°, 70.0°, 75.0°, 80.0°, 85.0°, 90.0°, or any range or amount therein in increments of 1°. The angle, $\theta_B$, alters the mouth orientation and can add to sweep by providing bias as described herein. As the angle, $\theta_B$, is increased, bias increases and sweep increases.

Figure 5B:
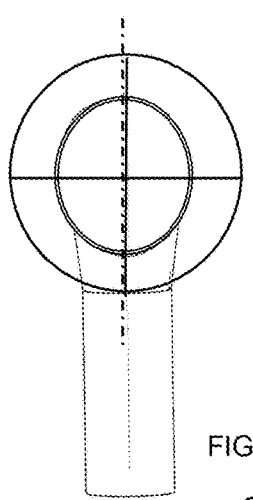
Figure 5C:
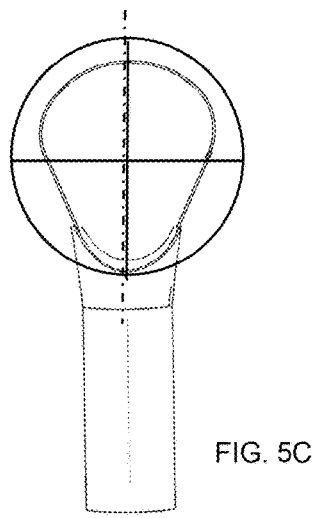
Figure 5D:
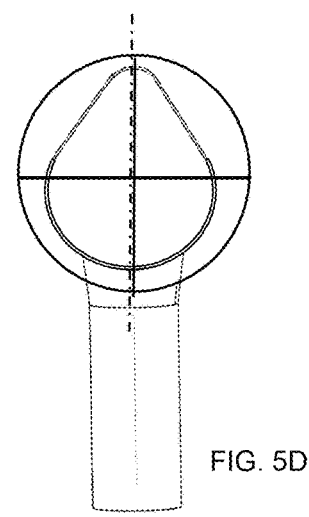
Figure 5E:
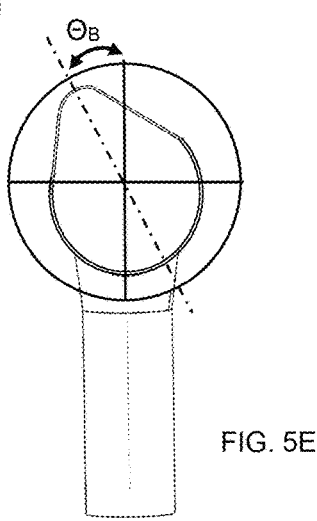
Figure 5F:
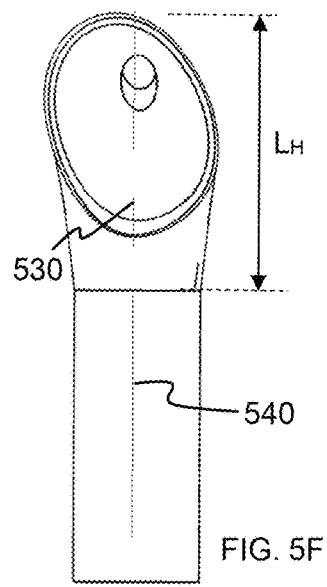

In some embodiments, as shown in FIG. 5B, the rim 221 of the mouth 220 can be circular with a mathematical center point to serve as a point of reference for mouth orientation relative to the neck of the thrombectomy device. In some embodiments, as shown in FIGS. 5C-5E, the rim 221 of the mouth 220 can be pear-shaped with an axis (a major axis) and a mathematical center point, wherein the wider part of the pear-shape can be located in proximal or distal location with no rotation of the major axis about the mathematical center point. In some embodiments, the major axis of the pear-shape can be rotated about the mathematical center point.

Head Tilt to Add Sweep

FIGS. 5F-5L show how to design a sweep offset, $S_O$, by selecting an offset angle, $\theta_O$, which adds "head tilt" in the cutter to offset the central axis of the head 220 of the tubular cutter 200 from the central axis of the neck 225 of the tubular cutter. The sweep offset allows the thrombectomy tubular cutter 200 to sweep beyond the diameter of the tubular cutter, $D_S$. Using the length of the head, $L_H$, of the thrombectomy tubular cutter 200 as a constant, the selection of the offset angle, $\theta_O$, provides the desired sweep offset, $S_O$ to increasing the cutting diameter inside the blood vessel for removal of a blood clot from a subject. In some embodiments, the diameter of the tubular cutter, $D_S$, is limited to 4 mm maximum to limit the size of the point of entry of the thrombectomy tubular cutter into the blood vessel of the subject. If the blood vessel is the iliac vein, the diameter can be, for example, about 10 mm in diameter. As such, it would be beneficial to offset the sweet of the head of the thrombectomy tubular cutter 200 to gain a much larger cutting diameter of the 4 mm thrombectomy tubular cutter in the iliac vein. For example, Using $S_O = L_H \sin \theta_O$; where $D_S$ is 4 mm, and $L_H$ is 6 mm, then $S_O$=6 mm sin 5=0.5 mm, where the offset angle, $\theta_O$, is selected as 5 degrees in FIG. 5F.

Figure 5G:
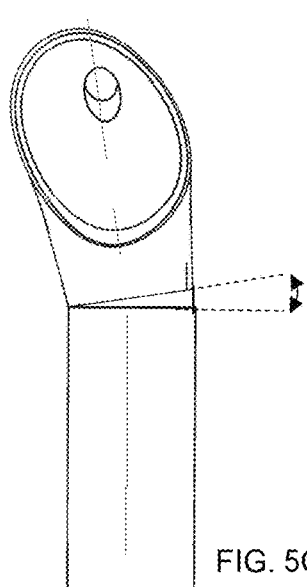

$S_O$=6 mm sin 10=1.0 mm, where the offset angle, $\theta_O$, is selected as 10 degrees in FIG. 5G.

Figure 5H:
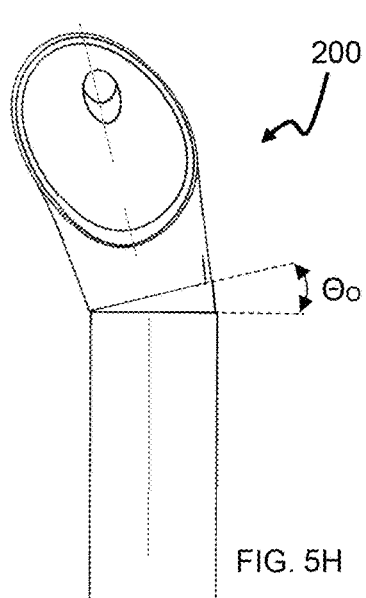

$S_O$=6 mm sin 15=1.6 mm, where the offset angle, $\theta_O$, is selected as 15 degrees in FIG. 5H.

Figure 5I:
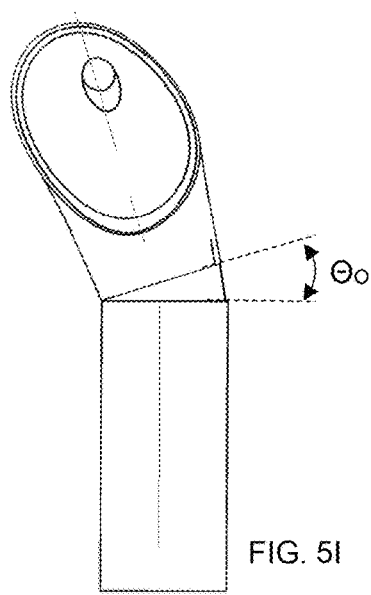
Figure 5J:
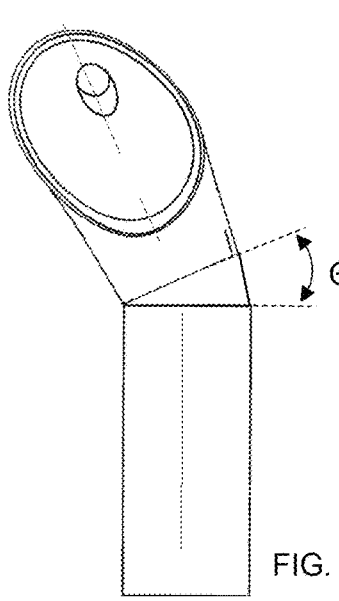
Figure 5K:
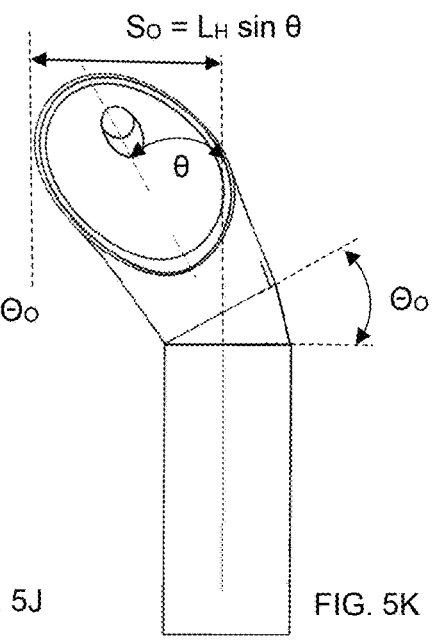

$S_O$=6 mm sin 20=2.1 mm, where the offset angle, $\theta_O$, is selected as 20 degrees in FIG. 5I $S_O$=6 mm sin 25=2.5 mm, where the offset angle, $\theta_O$, is selected as 25 degrees in FIG. 5J $S_O$=6 mm sin 30=3.0 mm, where the offset angle, $\theta_O$, is selected as 30 degrees in FIG. 5K $S_O$=6 mm sin 35=3.4 mm, where the offset angle, $\theta_O$, is selected as 35 degrees (not shown)

Figure 5L:
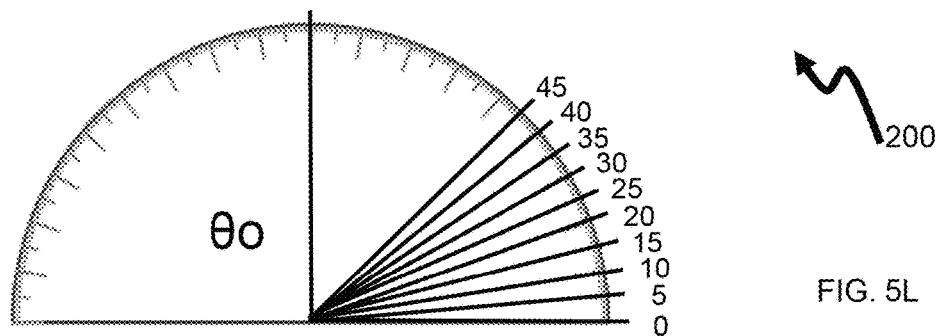

A protractor is shown in FIG. 5L illustrating angles ranging from 0 degrees to 45 degrees for convenience of reference. Using the above as an example of a design choice, an offset angle, $\theta_O$, which can be referred to as a lateral angle, lateral offset angle, or head tilt, of 25 degrees provides a sweep offset of 2.8 mm, which means that the thrombectomy tubular cutter 200 will have a cutting diameter of 4 mm+2.8 mm+2.8 mm=9.6 mm on a full rotation which will more effectively tubular cutter a thrombus 100 out of the iliac vein of the subject. As can be seen, the skilled artisan can control the sweep of the thrombectomy tubular cutter 200 by selecting the diameter of the tubular cutter, $D_S$, and the length of the head, $L_H$, and the offset angle, $\theta_O$.

In some embodiments, the lateral offset angle, $\theta_O$, can range from 0° to 90°, from 1° to 90°, from 2° to 90°, from 3° to 90°, from 4° to 90°, from 5° to 90°, from 6° to 90°, from 7° to 90°, from 8° to 90°, from 9° to 90°, from 10° to 90°, from 15° to 90°, from 20° to 90°, from 25° to 90°, from 30° to 90°, from 35° to 90°, from 40° to 90°, from 45° to 90°, from 50° to 90°, or any amount or range therein in increments of 1°. In some embodiments, the lateral offset angle, $\theta_O$, can range from 60° to 90°, from 70° to 90°, from 80° to 90°, or any amount or range therein in increments of 1°. In some embodiments, the lateral offset angle, $\theta_O$, can range from 0° to 60°, from 5° to 60°, from 10° to 60°, from 15° to 60°, from 20° to 60°, from 25° to 60°, from 30° to 60°, from 35° to 60°, from 40° to 60°, from 45° to 60°, from 50° to 60°, from 55° to 60°, or any amount or range therein in increments of 1°. In some embodiments, the lateral offset angle, $\theta_O$, can range from 0° to 45°, from 5° to 45°, from 10° to 45°, from 15° to 45°, from 20° to 45°, from 25° to 45°, from 30° to 45°, from 35° to 45°, from 40° to 45°, or any amount or range therein in increments of 1°. In some embodiments, the lateral offset angle, $\theta_O$, can range from 5° to 30°, from 10° to 30°, from 15° to 30°, from 20° to 30°, from 25° to 30°, or any amount or range therein in increments of 1°. In some embodiments, the lateral offset angle, $\theta_O$, can be 0°, 1 degree, 2 degrees, 3 degrees, 4 degrees, 5 degrees, 6 degrees, 7 degrees, 8 degrees, 9 degrees, 10 degrees, 11 degrees, 12 degrees, 13 degrees, 14 degrees, 15 degrees, 16 degrees, 17 degrees, 18 degrees, 19 degrees, 20 degrees, 21 degrees, 22 degrees, 23 degrees, 24 degrees, 25 degrees, 26 degrees, 27 degrees, 28 degrees, 29 degrees, 30 degrees, 31 degrees, 32 degrees, 33 degrees, 34 degrees, 35 degrees, 36 degrees, 37 degrees, 38 degrees, 39 degrees, 40 degrees, 41 degrees, 42 degrees, 43 degrees, 44 degrees, 45 degrees, or any amount or range therein in increments of 0.1 degrees. In some embodiments, the offset angle, Bo, can be selected to range from 1 degree to 45 degrees, from 1 degree to 40 degrees, from 1 degree to 35 degrees, from 1 degree to 30 degrees, from 1 degree to 25 degrees, from 1 degree to 20 degrees, from 1 degree to 15 degrees, from 1 degree to 10 degrees, from 1 degree to 5 degrees, or any amount or range therein in increments of 0.1 degrees.

Design of the Cutting Edge

Figure 6A:
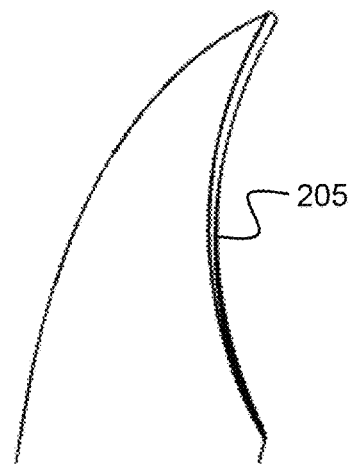
FIGS. 6A-6F illustrate a variety of rim and cutting edge shapes, according to some embodiments.
Figure 6B:
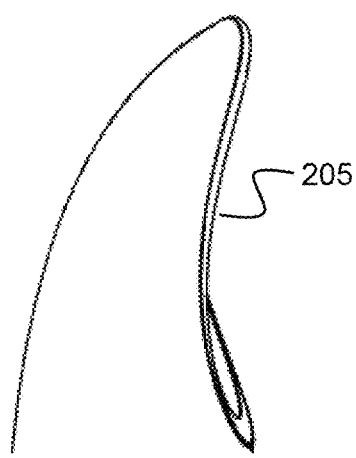
Figure 6C:

FIGS. 6A-6F illustrate a variety of rim and cutting edge shapes, according to some embodiments. In some embodiments, the cutting edge 205 and the trailing edge 210 each follow a parabolic equation of the general form $y=a(x-h)^2+k$, where a "+a" indicates that the parabola opens up, and a "−a" indicates that the parabola opens downward, and (h,k) indicates the position of the parabola's vertex, and the value of "a" dictates the steepness the parabola where, as the absolute value of "a" increases, the steepness of the parabola increases. The steepness of the parabola is the maximum slope possible, regardless of whether the slope is positive or negative, on a line tangent to the parabola. If the cutting edge 205 and the trailing edge 210 align, or at least "substantially" align, both parabola have the same or similar coordinates for the vertex which tells us whether the cutting edge, and both have the same or similar coefficient "a". The parabola "substantially" align when the alignment is close enough to believe that they may be the same, and there is little-to-no difference seen by a user of the device in removing the same or similar thrombus type from subjects. FIG. 6A illustrates equal parabolic, upward-opening curves that are aligned between the cutting edge 205 and the trailing edge 210 on the rim 221 of the mouth 220, meaning both parabola have the same or similar coordinates for the vertex, and both have the same or similar coefficient "a". FIG. 6B illustrates slightly unequal parabolic, upward-opening curves that when aligning the cutting edge 205 and the trailing edge 210 of the rim 221 of the mouth 220, appearing as though the k values are the same or similar because the vertical aligning is the same or similar, but the h values are significantly different because the parabola do not align horizontally, shifted left or right, of each other; the "a" coefficient appears the same or similar as the parabola have similar steepness. FIG. 6C can be explained similar to FIG. 6B, with the difference being that the difference in h values for the vertices are even more different than in FIG. 6B. As such, the shapes of the rims, namely the cutting edge and trailing edge, can be described and varied using the parabolic equation $y=a(x-h)^2+k$, varying the relative values of a, h, and/or k between the parabolic shapes of the cutting edge 205 and the trailing edge 210.

Figure 6D:
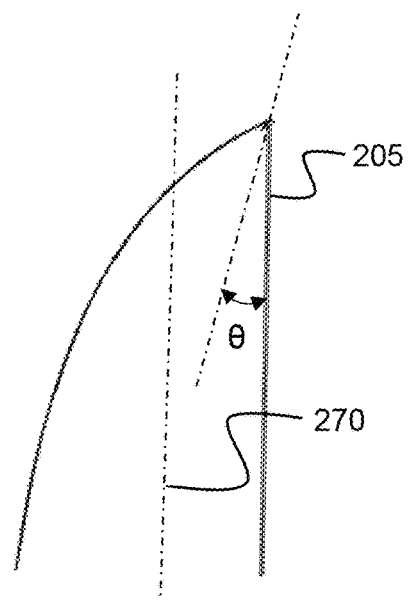

FIG. 6D illustrates how the cutting edge 205 can be linear in some embodiments, and the linear cutting edge 205 can lie on a plane having a major axis that is parallel to the axis 270 of the lumen of the neck of the thrombectomy device. In some embodiments, the linear cutting edge 205 can lie on a plane having a major axis that is at an angle, θ, relative to the axis 270 of the lumen of the neck of the thrombectomy device, where θ can have an angle that ranges from 1 degree to 20 degrees, from 1 degree to 18 degrees, from 1 degree to 16 degrees, from 1 degree to 14 degrees, from 1 degree to 12 degrees, from 1 degree to 10 degrees, from 1 degree to 8 degrees, from 1 degree to 6 degrees, from 1 degree to 4 degrees, or any angle or range therein in amounts of 1 degree. In some embodiments, the angle can be selected from the group consisting of 1 degree, 2 degrees, 3 degrees, 4 degrees, 5 degrees, 6 degrees, 7 degrees, 8 degrees, 9 degrees, 10 degrees, 11 degrees, 12 degrees, 13 degrees, 14 degrees, 15 degrees, 16 degrees, 17 degrees, 18 degrees, 19 degrees, and 20 degrees.

Figure 6E:
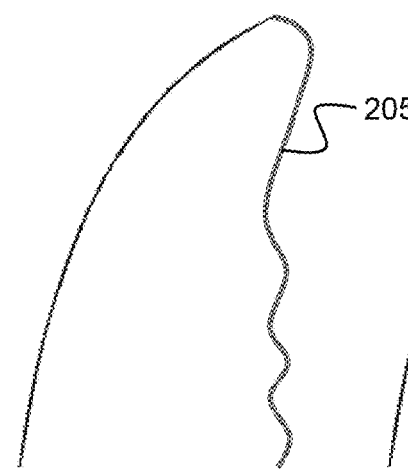
Figure 6F:
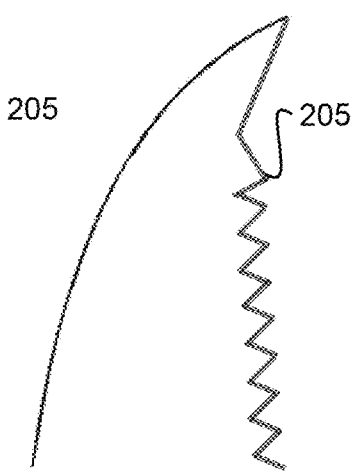

FIG. 6E illustrates how the cutting edge 205 can be undulating in some embodiments, and each undulation can be the same as the others, following the same or similar parabolic equation, or each undulation can have a parabolic equation that is independently selected, such that only some of the undulations share the same or substantially similar parabolic equation, or none of the undulations share the same or similar parabolic equation. Here we note that "substantially similar" parabolic equations can be close enough to visually conclude that they might be the same and would not be expected to perform differently in a thrombectomy. FIG. 6F illustrates how the cutting edge 205 can be serrated in some embodiments, and each serration can be the same or substantially similar to the others. Here we note that "substantially similar" serrations can be close enough to visually conclude that they might be the same and would not be expected to perform differently in a thrombectomy.

Figure 7A:
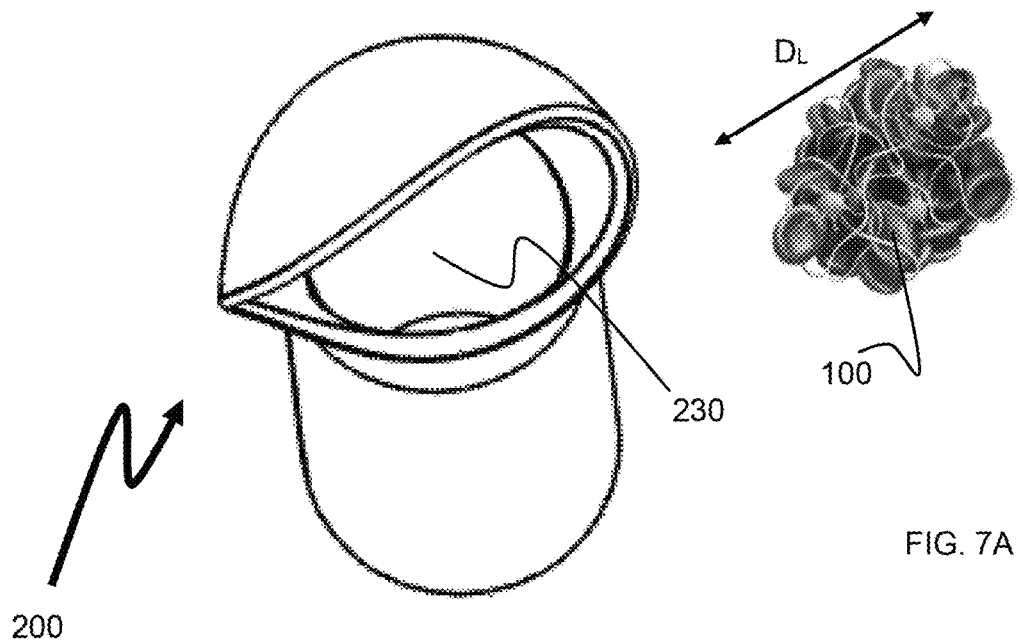
FIGS. 7A and 7B illustrate the size of a tubular cutter of thrombus relative to the size of the lumen in the neck of the thrombectomy tubular cutter, showing how the size of the mouth of the tubular cutter can affect the passage of the thrombus through the lumen, according to some embodiments.
Figure 7B:
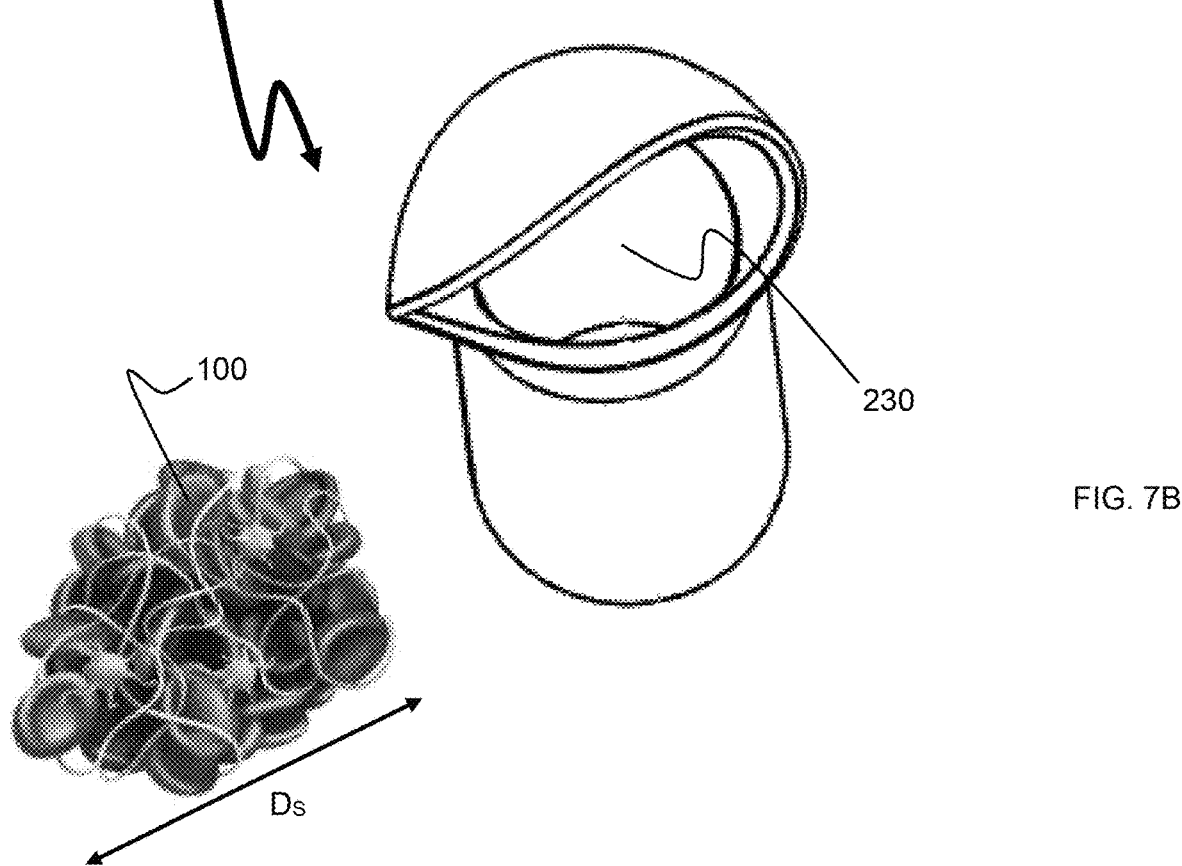

FIGS. 7A and 7B illustrate the size of a tubular cutter of thrombus relative to the size of the lumen in the neck of the thrombectomy tubular cutter, showing how the size of the mouth of the tubular cutter can affect the passage of the thrombus through the lumen, according to some embodiments. Referring back to FIG. 4B for detail, the mouth of the cutter can be designed to have an inlet diameter, $D_M$, that is smaller than the lumen $D_L$ of the flexible rotating shaft 305, to help ensure that a blood clot 100 captured by the thrombectomy tubular cutter 200 will not clog the flexible rotating shaft 305 during a thrombus removal. In some embodiments, the inlet of the mouth of the tubular cutter can have a cross-sectional area that is equal to, or less than, cross-sectional area of the lumen of the flexible, rotating shaft. In some embodiments, the inlet of the mouth of the tubular cutter can have a cross-sectional area that is greater than the lumen of the flexible, rotating shaft.

Since the actual relative differences between $D_M$ and $D_L$ can depend on the size of the cutting head, it should be appreciated that the sizing of the mouth and the lumen can be expressed as a ratio, where the ratio of $D_M/D_L$ can range from 0.20 to 1.00, from 0.30 to 1.00, from 0.40 to 1.00, from 0.50 to 1.00, from 0.60 to 1.00, from 0.70 to 1.00, from 1.00 to 2.00, from 1.00 to 1.90, from 1.00 to 1.80, from 1.00 to 1.70, from 1.00 to 1.60, from 1.00 to 1.50, from 1.00 to 1.45, from 1.00 to 1.40, from 1.00 to 1.35, from 1.00 to 1.30, from 1.00 to 1.25, from 1.00 to 1.20, from 1.00 to 1.15, from 1.00 to 1.10, from 1.00 to 1.05, or any ratio or range therein in increments of 0.01. In some embodiments, the $D_M$ is greater than $D_L$ by 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or any amount or range therein in increments of 0.1%. In some embodiments, the $D_M$ is greater than $D_L$ by 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or any amount or range therein in increments of 0.1%.

The lumen of the flexible rotating shaft can be approximated by the lumen of the neck of the thrombectomy tubular cutter 200 in some embodiments. It is reasonable that the diameter of the lumen of the neck of the thrombectomy tubular cutter can be, perhaps, smaller than the lumen of the flexible rotating shaft and, as such, can also be limited for thrombus size. As such, the diameter of the lumen $D_L$, of the neck 225 of the thrombectomy tubular cutter 200 can be sized as equal to or greater than the diameter of the inlet of the thrombectomy tubular cutter $D_M$. In some embodiments, $D_M < D_L$. In some embodiments, $D_M = D_L$. In some embodiments, $D_M > D_L$.

One of skill will appreciate that the "cleared diameter" of a vessel can be used to describe the diameter of the lumen of the blood vessel after passage of the thrombectomy tubular cutter through the lumen of the vessel. Since the vessel is often elastic, the cleared diameter of the lumen of a blood vessel may or may not be equal to the diameter of the cutter 200, namely the diameter of the head/mouth 220. The cleared diameter of the head/mouth 220 can be greater than the outer diameter of the neck 225 and, in some embodiments, the cleared diameter of the head/mouth 220 can be equal to than the outer diameter of the neck 225. In some embodiments, the cleared diameter of the head/mouth 220 can be less than the outer diameter of the neck 225.

In some embodiments, the relative sizes of the device components can have a significant impact on the movement of the device within a vessel lumen. In some embodiments, the cutter diameter can be configured to be greater than, and in some embodiments at least 10% greater, at least 20% greater, or at least 30% greater than the diameter of the flexible rotating shaft. The ratio of cutter diameter to the diameter of the flexible rotating shaft can range from 1.1 to 1.6 in some embodiments, 1.3 to 1.5 in some embodiments, 1.2 to 1.4 in some embodiments, 1.3 to 1.4 in some embodiments, or any range therein. In some embodiments, the ratio of cutter diameter to the diameter of the flexible rotating shaft can be 0.8, 0.9, 1.0, 1.1, 1.2, 1.3, 1.4, 1.5, 1.6, 1.7, 1.8, 1.9, 2.0, or any ratio therein in increments of 0.05, in some embodiments. In some embodiments, however, the cutter diameter is 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, or any percent therein in increments of 0.5%, greater than, or less than, the diameter of the flexible rotating shaft.

Systems

It should be appreciated that systems can also be assembled to include any devices taught herein. In some embodiments, a system can include a thrombectomy device taught herein and a delivery catheter. In some embodiments, a system can include a thrombectomy device taught herein and a guidewire. In some embodiments, a system can include a thrombectomy device taught herein, a guidewire, and a delivery catheter.

In some embodiments, a system can include a thrombectomy device taught herein and a vacuum port for connecting to a vacuum source. In some embodiments, a system can include a thrombectomy device taught herein, a guidewire, a delivery catheter, a vacuum port for connecting to a vacuum source, and the vacuum source. In some embodiments, the thrombectomy devices can include a vacuum port configured for operable communication with any vacuum source to facilitate transport of an excised tissue out of the subject. In some embodiments, a system can include a thrombectomy device taught herein having a vacuum port, wherein the vacuum port is in operable connection with an aspiration manifold for removal of a thrombus from the system, the aspiration manifold including a vented shaft with an aspiration hole configured for the removal of the thrombus away from the target site and out of the subject.

In some embodiments, the thrombectomy devices can have a handle that includes a motor operably connected to the flexible rotating shaft to turn the flexible rotating shaft to excise a tissue from a subject. In some embodiments, the thrombectomy devices can have a handle that includes a motor operably connected to a positive displacement pump having a flexible driveshaft, the motor configured to provide a rotational torque to the flexible driveshaft that actuates the positive displacement pump to transport thrombus tissue away from the target site and out of the subject.

In some embodiments, the thrombectomy devices can have a handle that includes a motor operably connected to a screw pump having a flexible driveshaft operably connected to a helical screw, the motor configured to provide a rotational torque to the flexible driveshaft that actuates the helical screw to transport thrombus tissue away from the target site and out of the subject.

In some embodiments, the thrombectomy devices can have a handle with a motor; and a flexible driveshaft operably connected to a helical screw; wherein, the motor is operably connected to
  a drive assembly that includes the flexible rotating shaft and the tubular cutter, the motor configured to provide a rotational torque to the flexible rotating shaft for rotating the tubular cutter and cutting the thrombus; and,
  the flexible driveshaft for rotating the helical screw to transport thrombus tissue away from the target site and out of the subject.

In some embodiments, the thrombectomy device can have a handle that includes a motor operably connected to a drive assembly that includes the flexible rotating shaft and the tubular cutter, the motor can be configured to provide a rotational torque to the flexible, rotating shaft for rotating the tubular cutter. The position of the cutting edge on the tubular cutter will determine whether the cutting head is rotated clockwise or counterclockwise as viewed from a position of the user that is proximal to the cutting head.

Figure 8:
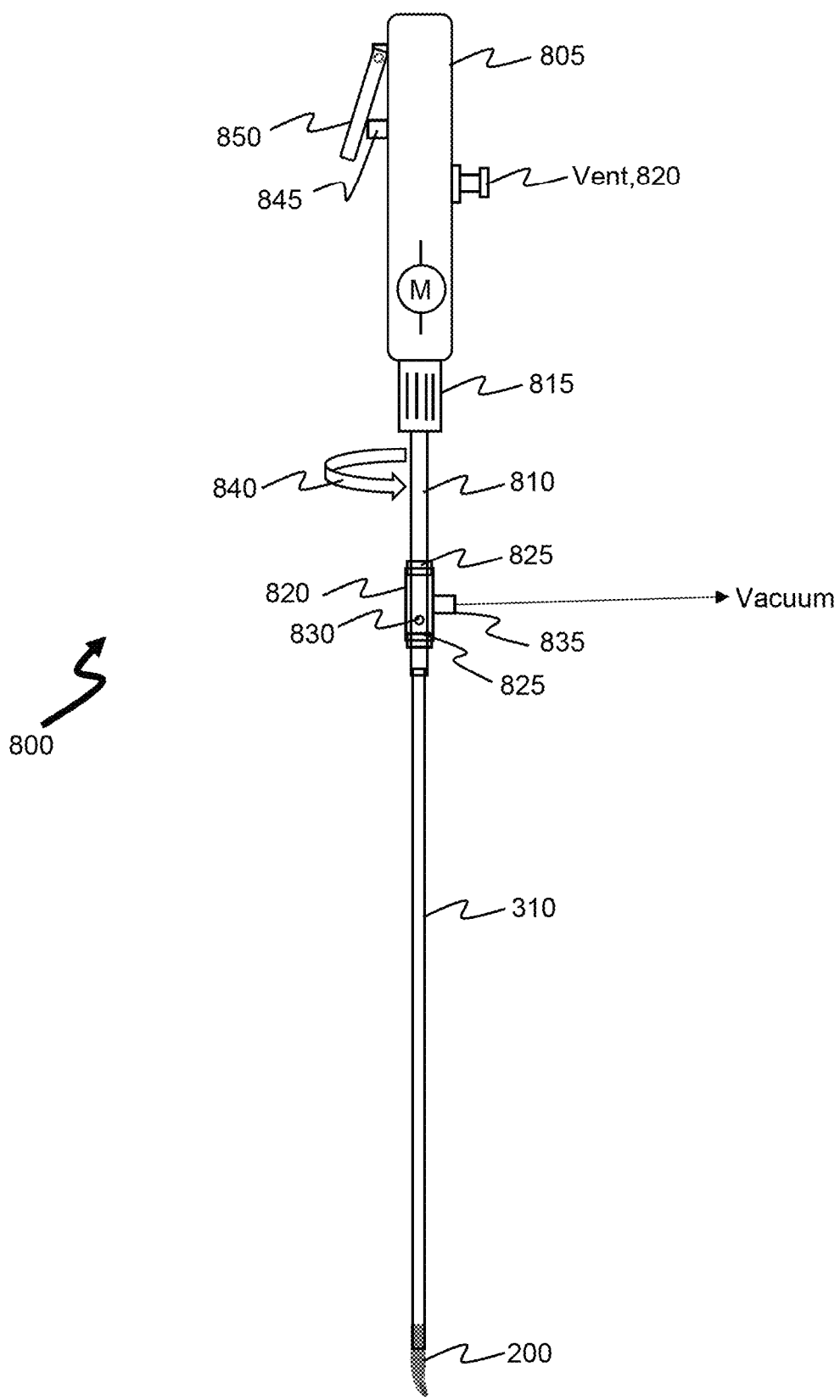
FIG. 8 illustrates a thrombectomy system having a motorized handle for rotating the thrombectomy tubular cutter, according to some embodiments.

FIG. 8 illustrates a thrombectomy system having a motorized handle for rotating the thrombectomy tubular cutter, according to some embodiments. The thrombectomy tubular cutter 200 is operatively connected to a flexible rotating shaft 310 which is operatively connected to a manifold 820 at fitting 825. The manifold 820 has an aspiration port 830 for discharging thrombus 100 through vacuum discharge port 835 using vacuum. The manifold 820 is operatively connected to a vent tube 810 that is connected to vent 820 in the handle 805. The handle 805 contains motor, M, for rotating 840 the vent tube 810 which in turn rotates the flexible, rotating shaft and the thrombectomy tubular cutter 200 from removal of a thrombus 100. The motor can operate using any source of power and, in some embodiments, the power is a battery source (not shown) located in the handle 805. The actuation of the rotation 840 through the motor, M, occurs through depression of a switch 845. In some embodiments, the switch 845 can be actuated using a squeeze trigger 850. Placing a seal over vent 820 allows vacuum to reach the lumen of the thrombectomy tubular cutter for vacuum removal of the thrombus 100 which can then be discharged through aspiration port 830 via the manifold 820.

Figure 9A:
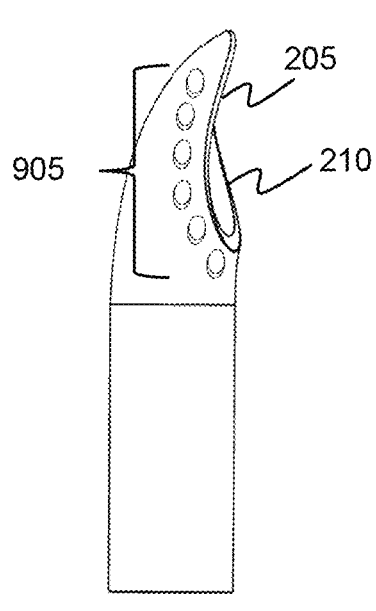
FIGS. 9A, 9B, 9D, 9E, and 9F illustrate blood filtration ports in the thrombectomy tubular cutter, according to some embodiments.
Figure 9B:
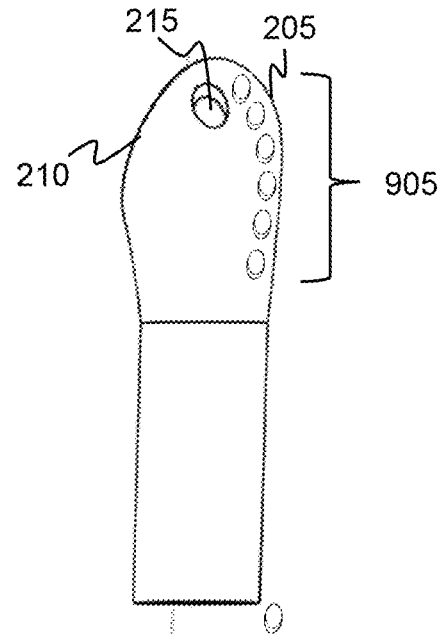
Figure 9D:
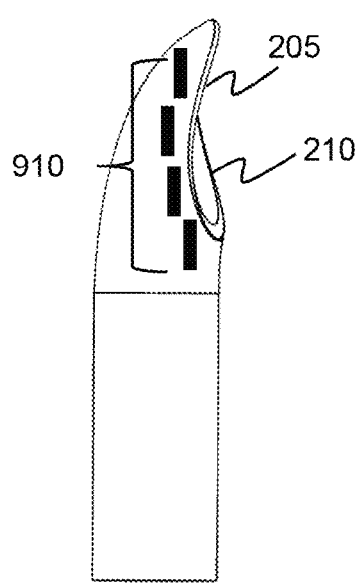
Figure 9E:
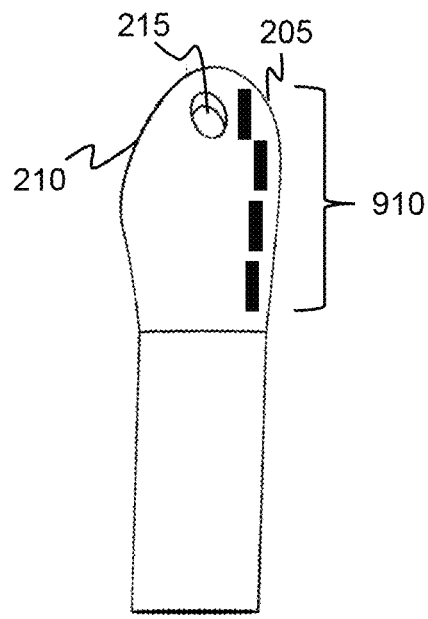
Figure 9F:

FIGS. 9A, 9B, 9D, 9E, and 9F illustrate blood filtration ports in the thrombectomy tubular cutter, according to some embodiments. The blood filtration ports 905,910 are a feature that facilitates the collection of thrombus tissue will allowing the blood to be released back into the blood vessel. Such ports can be any shape desired for optimal release of blood while tubular cutting and capturing a thrombus under vacuum. In some embodiments, as shown in FIGS. 9A and 9B, the blood filtration ports are round or elliptical 905. In some embodiments, as shown in FIGS. 9D and 9E, the blood filtration ports are square or rectangular 910. Any polygon or shape can be used, in some embodiments. Some alternate shapes contemplated for optimal filtration of thrombus from blood are provided in FIG. 9F. The blood filtration ports need to have a minimum size that allows the passage of all blood cells. For example, in some embodiments, the blood filtration ports can have a diameter (or effective diameter) as small as about 20 um to allow for the passage of monocytes.

In some embodiments, the blood filtration ports can have a diameter ranging from about 20 um to 2 mm, from about 20 um to 1 mm, from about 20 um to 0.5 mm, from about 20 um to 0.2 mm, from about 20 um to 0.1 mm, from about 20 um to 90 um, from about 20 um to 80 um, from about 20 um to 70 um, from about 20 um to 60 um, from about 20 um to 50 um, from about 20 um to 40 um, from about 20 um to 30 um, or any diameter or range therein in amounts of 1 um. In some embodiments, the shape of the blood filtration ports are not circular or elliptical, for example, and the minimum dimension is at least 20 um, the diameter possibly ranging from at least 20 um to 200 um, 20 um to 100 um, 50 um to 100 um, 50 um to 150 um, 75 um to 125 um, or any amount or range therein in increments of 1 um.

In some embodiments, the blood filtration ports can have a diameter ranging from about 40 um to 2 mm, from about 40 um to 1 mm, from about 40 um to 0.5 mm, from about 40 um to 0.2 mm, from about 40 um to 0.1 mm, from about 40 um to 90 um, from about 40 um to 80 um, from about 40 um to 70 um, from about 40 um to 60 um, from about 40 um to 50 um, or any diameter or range therein in amounts of 1 um. In some embodiments, the shape of the blood filtration ports are not circular or elliptical, for example, and the diameter is at least 40 um and can range from at least 40 um to 200 um, 40 um to 100 um, or any amount or range therein in increments of 1 um. In some embodiments, the blood filtration ports can have a minimum dimension of 10 um, 15 um, 20 um, 25 um, 30 um, 35 um, 40 um, 45 um, 50 um, 55 um, 60 um, 65 um, 70 um, 75 um, 80 um, 85 um, 90 um, 95 um, 100 um, 105 um, 110 um, 115 um, 120 um, 125 um, 130 um, 135 um, 140 um, 145 um, 150 um, or any dimension or range therein in increments of 1 um. The maximum dimension of a blood filtration port can be, for example, 100 um, 150 um, 200 um, 250 um, 300 um, 350 um, 400 um, 450 um, 500 um, or any amount therein in increments of 10 um.

In some embodiments, the blood filtration ports can be placed closer to the cutting edge of the thrombectomy tubular cutter than the trailing edge of the thrombectomy tubular cutter. In some embodiments, the blood filtration ports can be placed closer to the trailing edge of the thrombectomy tubular cutter than the cutting edge of the thrombectomy tubular cutter. In some embodiments, the blood filtration ports can cover the head 220 of the thrombectomy tubular cutter in an amount of 1, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or any amount or range therein in increments of 0.1%. In some embodiments, the blood filtration ports can cover the head 220 of the thrombectomy tubular cutter in a range of 1% to 10%, 1% to 15%, 1% to 20%, 1% to 25%, 1% to 30%, 1% to 40%, 1% to 50%, or any amount or range therein in increments of 0.1%. In some embodiments, the blood filtration ports can cover the head 220 of the thrombectomy tubular cutter in a range of 3% to 10%, 3% to 15%, 3% to 20%, 3% to 25%, 3% to 30%, 3% to 40%, 3% to 50%, or any amount or range therein in increments of 0.1%. In some embodiments, the blood filtration ports can cover the head 220 of the thrombectomy tubular cutter in a range of 5% to 10%, 5% to 15%, 5% to 20%, 5% to 25%, 5% to 30%, 5% to 40%, 5% to 50%, or any amount or range therein in increments of 0.1%. Any number of blood filtration ports can be used. In some embodiments, this percent coverage can translate to 1 port, 2 ports, 3 ports, 4 ports, 5 ports, 6 ports, 7 ports, 8 ports, 9 ports, 10 ports, 11 ports, 12 ports, 13 ports, 14 ports, 15 ports, 16 ports, 17 ports, 18 ports, 19 ports, 20 ports, 25 ports, 30 ports, 35 ports, 40 ports, 45 ports, 50 ports, or more, and any range of number of ports therein.

The blood filtration ports can be open ports in some embodiments, and one-way valves in some embodiments. The one-way valves would be operable to allow blood to leave the lumen of the thrombectomy tubular cutter through the ports, but not enter the lumen of the thrombectomy tubular cutter through the ports. In some embodiments, the one-way valve can be a flap valve, or a butterfly valve. In some embodiments, the one-way valve can be referred to as a non-return valve and can be selected from the group consisting of duckbill valves, cross slit valves, dispensing valves, flange valves, flap valves, and combinations thereof. Any one-way valve known to one of skill to work in such a micro environment can be used.

Those of skill understand that guidewires can be used to locate a diseased region, or target region, in a blood vessel. Also, a guidewire can be used to direct the thrombectomy devices taught herein over the target region. In some embodiments, the guidewire lumen diameter can range in size from 0.01 to 0.20 inches, from 0.01 to 0.18 inches, from 0.01 to 0.15 inches, from 0.01 to 0.10 inches, or any range therein in some embodiments. In some embodiments, the guidewire lumen diameter can range from 0.01 to 0.14 inches. In some embodiments, the guidewire lumen diameter is 0.01 inches (0.254 mm), 0.02 inches (0.508 mm), 0.04 inches (1.016 mm), 0.06 inches (1.524 mm), 0.08 inches (2.032 mm), 0.10 inches (2.540 mm), 0.12 inches (3.048 mm), 0.14 inches (3.556 mm), 0.16 inches (4.064 mm), 0.18 inches (4.572 mm). 0.20 inches (5.080 mm), or any diameter therein in increments of 0.01 inches (0.254 mm).

The tissue removed by the devices taught herein can be removed mechanically, by vacuum displacement, by a positive displacement pump, or some combination thereof. In some embodiments, the thrombectomy device has a handle that includes a motor operably connected to a positive displacement pump having a flexible driveshaft, the motor configured to provide a rotational torque to the flexible rotating shaft that actuates the positive displacement pump to transport thrombus tissue away from the tubular cutter.

In some embodiments, the thrombectomy devices can have a screw pump with a rotating helical screw for removing thrombus tissue from the blood vessel, and the right hand or left hand direction of the helix will determine whether the screw pump is rotated clockwise or counterclockwise as viewed from a proximal position of the user that is proximal to the cutting head. The cutting head and the screw pump can be rotated in the same direction in some embodiments, or opposite directions in other embodiments. A right-hand helical screw could be used for a clockwise rotation of the screw when viewed from a position proximal to the head of the cutter, whereas a left-hand helical screw (not shown) could be used for a counterclockwise rotation of the screw when viewed from a position proximal to the head of the cutter.

Figure 10A:
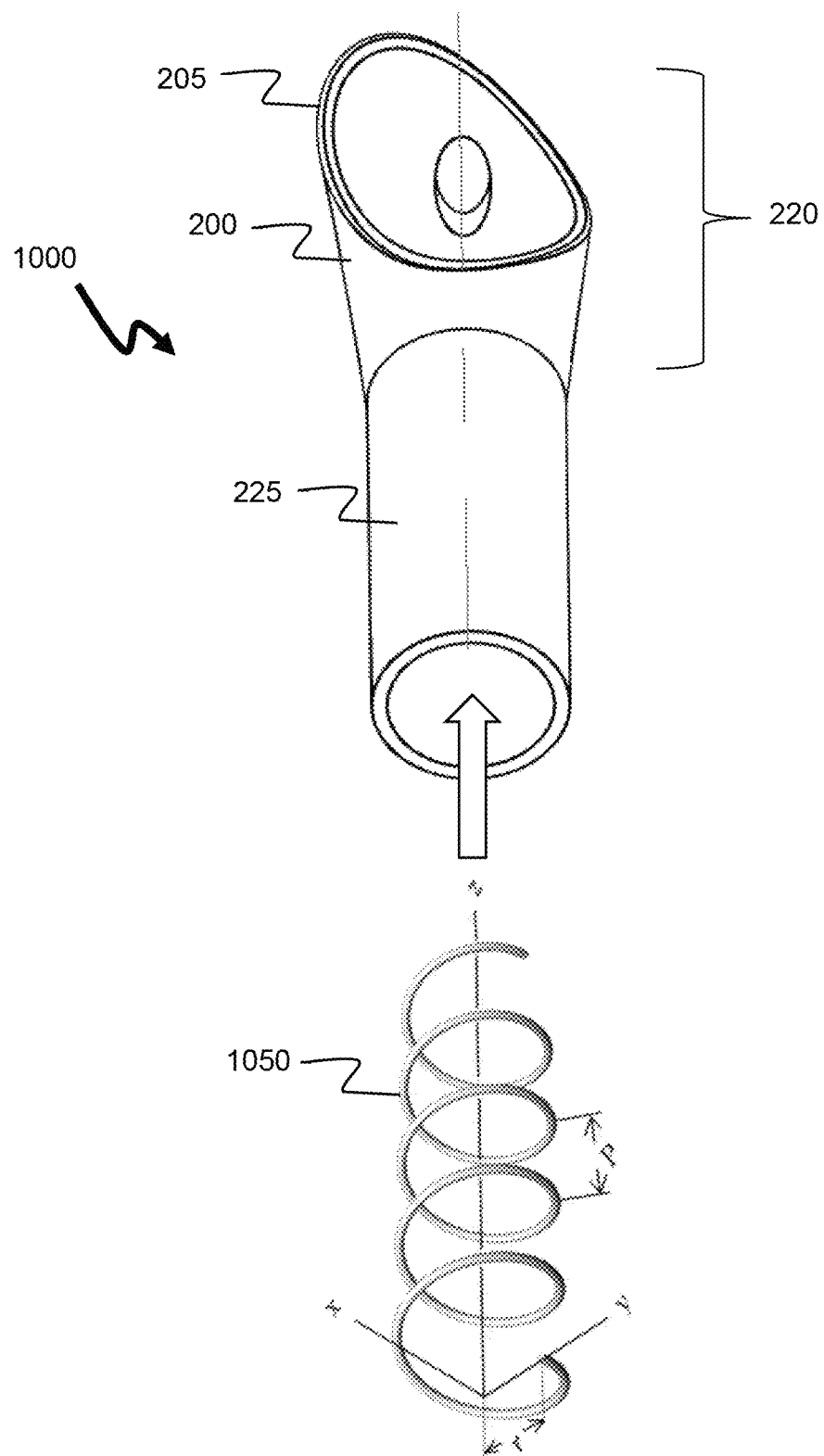
FIGS. 10A and 10B illustrate a rotational shaft of a thrombectomy tubular cutter system having a positive displacement pump, according to some embodiments.
Figure 10B:
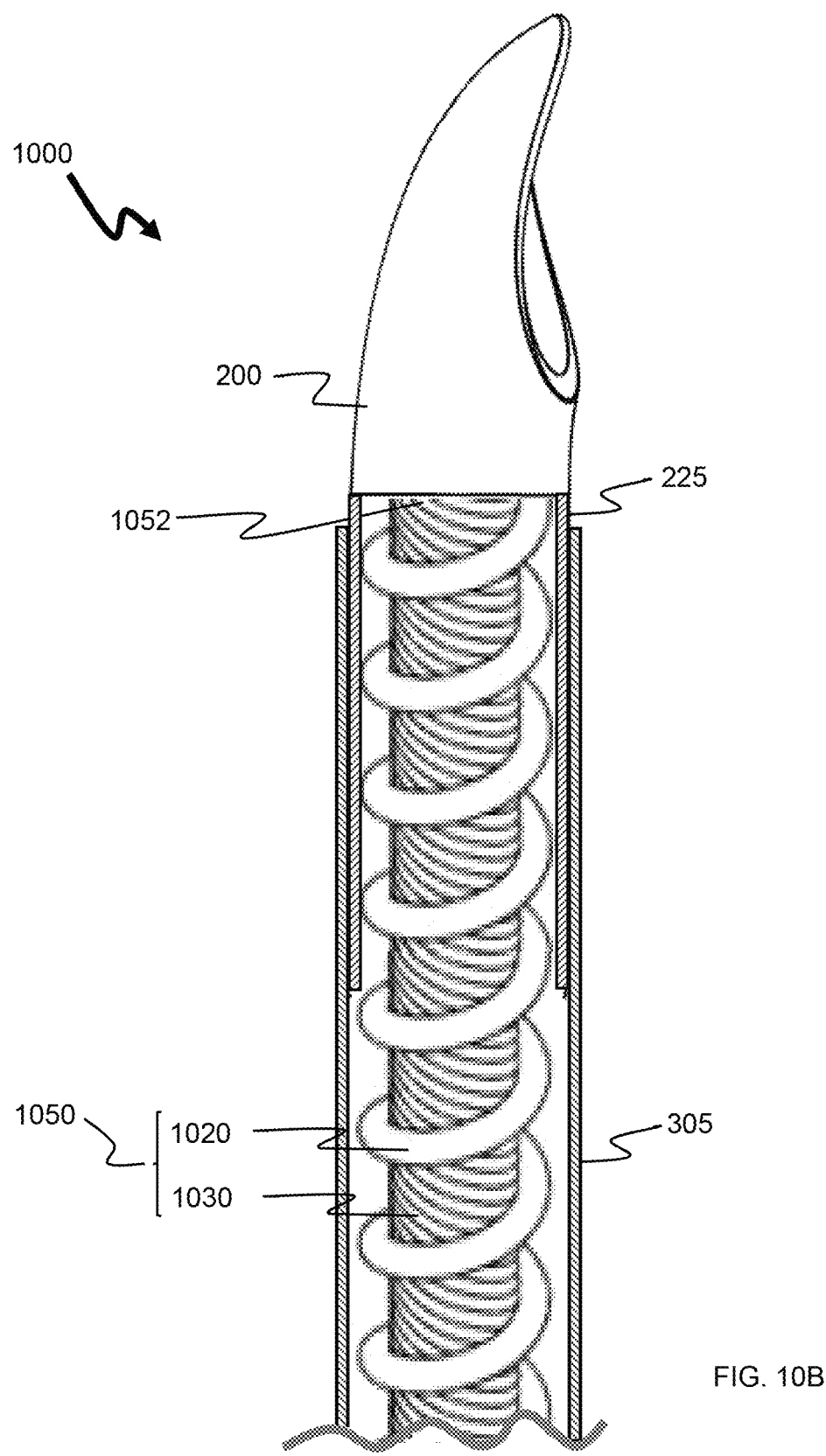

FIGS. 10A and 10B illustrate a rotational shaft of a thrombectomy tubular cutter system having a positive displacement pump, according to some embodiments. In some embodiments, thrombectomy tubular cutter system 1000 includes a drive assembly that includes the flexible, rotating shaft 305 (not shown) that operably connects to the neck 225, for example, by friction fit, mechanical interlock, or adhesion, and turns the head/mouth 220, in a clockwise rotation from the perspective of the user at the proximal end of the device, to cut and remove the thrombus 100 (not shown) from the vascular lumen.

As shown in FIG. 10A, positive displacement pump 1050 is a helical screw 1050 that can be a helical-shaped wire that is fixably attached to the lumen of the neck 225 of the thrombectomy tubular cutter 200, such that a rotation of the thrombectomy tubular cutter 200 is necessary a rotation of the helical screw 1050 to convey thrombus tissue proximally through the thrombectomy tubular cutter 200. The helical-shaped wire can be designed to conform to the lumen of the neck 225 of the thrombectomy device 200 by selecting a radius, r, that matches the radius of the lumen of the neck 225 of the thrombectomy device 200. The pitch of the helix, P, can be selected to obtain an effective transport of thrombus tissue. The positive displacement pump 1050 can be further assisted by configuring the system such that the positive displacement pump is in communication with a vacuum source (not shown) to draw the excised tissue out of the subject.

In some embodiments, the thrombectomy device has a handle that includes a motor operably connected to a screw pump having a drive assembly (not shown) operably connected to the thrombectomy tubular cutter 200 to turn the head 200 to cut the thrombus tissue 100, and concurrently turn the helical screw 1050 that is fixably attached to the lumen of the neck 225 of the thrombectomy tubular cutter 200. The motor can be configured to provide a rotational torque to the thrombectomy tubular cutter that actuates the cutting of the thrombus tissue and the transport of the thrombus tissue proximally with the helical screw. The helical-shaped wire can be a right-handled helix much like a right-handed drillbit, or a left-handed helix, much like a left-handed drillbit, where the right-handed helix is used when turning the thrombectomy tubular cutter 200 clockwise when viewed from a position proximal to the thrombectomy tubular cutter 200, and the left-handed helix is used when turning the thrombectomy tubular cutter 200 counterclockwise when viewed from a position proximal to the thrombectomy tubular cutter 200. As noted, a source of vacuum can be used to facilitate removal of the excised tissue from the subject.

FIG. 10B illustrates a cross-section of the neck and flexible, rotational shaft of a thrombectomy tubular cutter system having a positive displacement pump, according to some embodiments. As shown in FIG. 10B, the positive displacement pump can rotate with the drive assembly, and independent of the thrombectomy tubular cutter 200 in some embodiments. For example, the positive displacement pump can have a rotating screw pump 1050 with a helical screw 1020 to move the thrombus tissue. In some embodiments, the positive displacement pump can rotate independent of the rotation of the drive assembly for the cutting head 200. In some embodiments, the positive displacement pump can be a screw pump 1050 configured with a helical screw 1020 located on a flexible driveshaft 1030 that rotates independent of the rotation of the cutting head 200. As noted, a source of vacuum can be used to facilitate removal of the excised tissue from the subject.

As such, the thrombectomy devices can have a handle with a motor; and a flexible driveshaft operably connected to a helical screw; wherein, the motor is operably connected to a drive assembly that includes the flexible rotating shaft and the tubular cutter, the motor configured to provide a rotational torque to the flexible rotating shaft for rotating the tubular cutter and cutting the thrombus; and, a flexible driveshaft 1030 within the flexible rotating shaft 305 for rotating the helical screw to transport thrombus tissue away from the tubular cutter.

Indications and Design of Devices

The versatile devices, systems, and methods taught herein can handle each of the variety of soft, tough, fibrous, and hard tissue effectively, and as such, can be used in thrombectomies and atherectomies. A thrombectomy is the removal of a blood clot from a blood vessel. Blood clots are made up of platelets and a meshwork of protein strands called fibrin. Clots in arteries have a different composition than clots in veins, in which clots in arteries contain mostly platelets and clots in veins contain mostly fibrin. Common applications for thrombectomies include any location in a blood vessel where a thrombus may occur. The thrombectomy removes the blood clot from the wall of a blood vessel to help alleviate symptoms of the condition, as well as the downstream complications that can include further vasculature complications, and perhaps even death from the release of an embolus. Atherosclerosis is also referred to as plaque on the luminal wall of an artery, and plaque includes deposits of fatty substances, cholesterol, cellular waste products, calcium, and fibrin. Both the atherosclerosis and thrombus pose a risk of fragmenting into the blood stream, and moving to the heart, brain, or lungs, causing health complications and often proving to be fatal. The devices, systems, and methods taught herein can be used to treat all such indications that involve the removal of tissue from a blood vessel.

The thrombus can be in a vein as a venous thrombosis, or an artery as an arterial thrombosis. An indication of particular importance is the removal of a thrombus from a pulmonary artery, also referred to as a pulmonary embolism. The size of the artery or vein can be used to select the size, or diameter of the head 220, of the thrombectomy tubular cutter 200. Peripheral vascular disease in the legs is an example of a condition that can be treated using the thrombectomy devices taught herein.

In some embodiments, the diameter of a target blood vessel can be used to size the diameter, $D_S$, of the head of the tubular cutter 200. In some embodiments, the diameter of the target blood vessel can be a reference point as the maximum diameter to use as the diameter of the head 220 of the tubular cutter. However, in some embodiments, the blood vessel is much larger than the diameter, $D_S$, of the tubular cutter 200.

It should be appreciated blood vessels of a wide range of lumen diameters can be treated. The lumen diameters can range for example, from about 2.0 mm to about 30.0 mm, from about 3.0 mm to about 25.0 mm, from about 4.0 mm to about 24.0 mm, from about 5.0 mm to about 23.0 mm, from about 6.0 mm to about 25.0 mm, from about 7.0 mm to about 21.0 mm, from about 8.0 mm to about 20.0 mm, or any range or amount therein in increments of 0.1 mm. In some embodiments, the lumen diameters of the blood vessels treated can be 2.0 mm, 3.0 mm, 4.0 mm, 5.0 mm, 6.0 mm, 7.0 mm, 8.0 mm, 9.0 mm, 10.0 mm, 11.0 mm, 12.0 mm, 13.0 mm, 14.0 mm, 15.0 mm, 16.0 mm, 17.0 mm, 18.0 mm, 19.0 mm, 20.0 mm, 21.0 mm, 22.0 mm, 23.0 mm, 24.0 mm, 25.0 mm, 26.0 mm, 27.0 mm, 28.0 mm, 29.0 mm, 30.0 or any range or amount therein in increments of 1.0 mm.

In some embodiments, the diameter, $D_S$, of the head 220 of the tubular cutter 200 is selected to be reduced from the diameter of the target vessel in an amount of at least 1%, 5%, 10%, 15%, 20%, 25%, 30%, 35%, 40%, 45%, 50%, or any amount or range therein in increments of 1%. In some embodiments, the diameter, $D_S$, of the head 220 of the tubular cutter is selected to be reduced from the diameter of the target vessel in an amount ranging from 1% to 10%, from 1% to 15%, from 1% to 20%, from 1% to 25%, from 1% to 30%, from 1% to 40%, from 1% to 50%, or any amount or range therein in increments of 1%. In some embodiments, the diameter, $D_S$, of the head 220 of the tubular cutter is selected to be reduced from the diameter of the target vessel in an amount ranging from 5% to 10%, from 5% to 15%, from 5% to 20%, from 5% to 25%, from 5% to 30%, from 5% to 40%, from 5% to 50%, or any amount or range therein in increments of 0.1%.

The main targets and indications for use with the devices, systems, and methods taught herein includes the removal of venous thrombus. In some embodiments, the systems, devices, and methods can be configured for removal of a venous thrombus, and the lumen diameters of the blood vessels treated can range, for example, from about 4.0 mm to about 16.0 mm, or any amount or range therein in increments of 1.0 mm. In these embodiments, the outer diameter of the tubular cutter and/or the flexible rotating tube can range from about 4 mm to about 8 mm, or any amount or range therein in increments of 1.0 mm.

In some embodiments, the systems, devices, and methods taught herein can be configured for removal of a pulmonary arterial thrombus, and the lumen diameters of the blood vessels treated can range, for example, from about 6.0 mm to about 25.0 mm, or any amount or range therein in increments of 0.1 mm. In these embodiments, the outer diameter of the tubular cutter and/or the flexible rotating tube can range from about 4 mm to about 8 mm, or any amount or range therein in increments of 0.1 mm.

Table 1 provides examples of some venous lumen diameters in mm for veins which can be treated with the devices taught herein.

TABLE 1

Examples of some venous lumen diameters in mm.

| Vein | Average (mm) | Std dev (mm) |
|---|---|---|
| Common femoral | 13.7 | 2.8 |
| Superficial femoral proximal | 9.2 | 1.8 |
| Superficial femoral half | 8.2 | 1.5 |
| Superficial femoral distal | 8.5 | 1.4 |
| Popliteal | 8.9 | 1.8 |
| Long saphenous proximal | 5.0 | 0.9 |
| Long saphenous half | 4.0 | 1.0 |
| Long saphenous distal | 3.0 | 0.6 |
| Short saphenous | 2.9 | 1.0 |
| Posterior tibial 1 | 3.3 | 0.6 |
| Posterior tibial 2 | 3.5 | 0.7 |
| Anterior tibial 1 | 2.4 | 0.5 |
| Anterior tibial 2 | 2.3 | 0.6 |
| Peroneal 1 | 3.0 | 0.8 |
| Peroneal 2 | 3.0 | 0.9 |
| Gastrocnemial 1 | 3.2 | 1.0 |
| Gastrocnemial 2 | 2.9 | 0.7 |
| Common Iliac vein (8-10 mm) | 13.0 | 2.4 |
| External Iliac vein | 8.0 | |
| Internal Iliac vein | 4.0 | |

In some embodiments, a treated vein can have a lumen diameter ranging from 4 mm to 18 mm. In some embodiments, the diameter of the vein can range from 1 mm to 10 mm, from 2.0 mm to 10 mm, from 3.0 mm to 10 mm, from 4.0 mm to 10 mm, from 5.0 mm to 10 mm, from 6.0 mm to 10 mm, from 7.0 mm to 10.0 mm, from 8.0 mm to 10.0 mm or any range or amount therein in increments of 1.0 mm. In some embodiments, the treated vein can have a lumen diameter selected from the group consisting of 2.0 mm, 3.0 mm, 4.0 mm, 5.0 mm, 6.0 mm, 7.0 mm, 8.0 mm, 9.0 mm, 10.0 mm, or any amount or range therein in increments of 1.0 mm. In some embodiments, the treated vein can have a lumen diameter selected from the group consisting of 11.0 mm, 12.0 mm, 13.0 mm, 14.0 mm, 15.0 mm, 16.0 mm, 17.0 mm, 18.0 mm, 19.0 mm, 20.0 mm, 21.0 mm, 22.0 mm, 23.0 mm, 24.0 mm, 25.0 mm, 26.0 mm, 27.0 mm, 28.0 mm, 29.0 mm, 30.0 mm or any amount or range therein in increments of 1.0 mm.

Clots in the venous system can vary greatly in size, and the thrombectomy tubular cutter will need to be sized accordingly. In some embodiments, a thrombus can have a clot diameter ranging from about 1.0 mm to about 18.0 mm. In embodiments involving deep vein thrombosis, for example, a thrombus can be found in larger veins and have a clot diameter ranging from about 3.0 mm to about 8.0 mm. In some embodiments, a thrombus can be found in the common iliac veins and the inferior vena cava having a clot diameter ranging from about 7.0 mm to about 17.0 mm. In some embodiments, a thrombus can be found in the external iliac veins and common femoral veins having a clot diameter ranging from about 5 mm to about 14 mm. In some embodiments, a thrombus can be found in the superficial femoral, deep femoral and popliteal veins having a clot diameter ranging from about 4 mm to about 10 mm. And, in some embodiments, a thrombus can be found in the calf veins ranging from about 4 mm to about 8 mm.

Any vein can be treated using the devices, systems, and methods taught herein. In some embodiments, the devices, systems, and methods are designed for treating the iliac veins. And, in some embodiments, the devices, systems, and methods are designed for treating the popliteal veins. In some embodiments, the devices, systems, and methods are designed for treating any veins from the popliteal veins to the iliacs.

As noted, the devices, systems, and methods are directed mainly toward thrombectomies. However, in some embodiments, the systems, devices, and methods can be configured for treatment of arteries, or atherectomies. Table 1 provides examples of some arterial lumen diameters in mm for arteries which can be treated with the devices taught herein.

TABLE 2

| Artery | Average (mm) |
| --- | --- |
| Aorta | 17-35 |
| Main pulmonary artery | 18.5-29.5 |
| Right pulmonary artery | 12.4-19.8 |
| Left pulmonary artery | 14.3-22.1 |
| Superior femoral | 5-7 |
| Popliteal | 3.5-4.5 |
| Anterior tibial | 3.0 |
| Tibioperoneal trunk | 2.5 |
| Posterior tibial | 2.0 |
| Peroneal | 2.0 |

The superior femoral artery, located about mid-femur, generally has a diameter of about 5 to 7 mm, or about 0.2 to 0.25 inch. As the artery descends below the knee, the popliteal artery generally has a diameter of about 4 to 4.5 mm (0.157 inch to 0.177 inch), and then reduces to about 3.5 mm (0.137 inch) as you move in the direct of the subject's foot. The popliteal artery branches again into the anterior tibial artery and the tibioperoneal trunk, reducing further in diameter to about 3.0 mm and then about 2.5 mm or about 0.118 inch to 0.098 inch. The tibioperoneal trunk further subdivides into the posterior tibial and peroneal arteries, further reducing in diameter to about 2.0 mm (0.078 inch). In some embodiments, the diameters of the peripheral arteries of the leg can vary, typically, from about 2 mm to about 7 mm. Any blood vessel can contain plaque and be a prospective target area for the thrombectomy devices taught herein. For example, coronary arteries are about 3 mm in size, varies from 2.5-4.5 in diameter, and coronary arteries can be prospective target areas for the devices taught herein if designed for use in an atherectomy.

For smaller clots, the diameter of the cutter can range from about 1.0 mm to about 3.0 mm in some embodiments, 1.5 mm to 4.0 mm in some embodiments, or any range therein in increments of 0.10 mm. In some embodiments, the diameter of the cutter can be about 1.0 mm, about 2.0 mm, about 3.0 mm, about 4.0 mm, about 5.0 mm, or any diameter therein, or range therein, in increments of 0.1 mm.

For larger clots, the diameter of the cutter can range from about 3.0 mm to 9.0 mm in some embodiments, 4.0 mm to 8.0 mm in some embodiments, and 5.0 mm to 7.0 mm in some embodiments, or any amount or range therein in increments of 0.1 mm. In some embodiments, the diameter of a larger cutter can be about 3.0 mm, about 4.0 mm, about 5.0 mm, about 6.0 mm, about 7.0 mm, about 8.0 mm, about 9.0 mm, 10.0 mm or any diameter therein, or range therein, in increments of 0.1 mm.

Although it seems reasonable to simply increase the diameter of the cutter for larger blood vessels, the skilled artisan will realize that the diameter of the cutter can also be limited by physical complications of the patient's anatomy. For example, there can be complications that occur during surgery due to bleeding at the puncture access, tortuous vessels, vessel size variations, and the like. The skilled artisan can use the teachings herein, including cutter size, cutter bias, ratio of leading edge to trailing edge, cutter deflection, selection of stiffness, and any combination thereof, to design a desired thrombectomy device to obtain the desired treatment results.

The skilled artisan will also realize that the length of the cutter has to be limited to have the maneuverability needed. One of skill will realize that the size of the head of the cutter can be any length known to be suitable in the art for the particular treatment. In some embodiments, the length of the head of the cutter can range from about 4.0 mm to about 20.00 mm, from about 4.0 mm to about 18.0 mm, from about 4.0 mm to about 16.0 mm, from about 4.0 mm to about 12.0 mm, or any range or amount therein in increments of 0.10 mm. In some embodiments, the length of the head of the cutter can range from about 6.0 mm to about 20.00 mm, from about 6.0 mm to about 18.0 mm, from about 6.0 mm to about 16.0 mm, from about 6.0 mm to about 12.0 mm, or any range or amount therein in increments of 0.10 mm. In some embodiments, the length of the head of the cutter can range from about 8.0 mm to about 20.00 mm, from about 8.0 mm to about 18.0 mm, from about 8.0 mm to about 16.0 mm, from about 8.0 mm to about 12.0 mm, or any range or amount therein in increments of 0.10 mm. In some embodiments, the length of the head of the cutter can be about 1.0 mm, about 2.0 mm, about 3.0 mm, about 4.0 mm, about 5.0 mm, about 6.0 mm, about 7.0 mm, about 8.0 mm, or any diameter therein, or range therein, in increments of 0.1 mm.

Given the relative sizes of the vessels and devices taught herein, it should be appreciated by the skilled artisan that a thrombectomy device can have a shaft diameter that 2× the size of a shaft used in an atherectomy device. In some embodiments, this is why the torsional stiffness of a thrombectomy device can be 16× that of the atherectomy device, and the flexural stiffness of the thrombectomy devices can be 8× that of the atherectomy device. Likewise, the axial stiffness of the thrombectomy device can be about 2× that of the atherectomy device.

As discussed the devices, systems and methods can be used in thrombectomies and atherectomies, although thrombectomies are the focus. As such, methods of using thrombectomy devices and systems, and methods of using atherectomy devices and systems are provided.

In some embodiments, the teachings are directed to a method of removing tissue from a blood vessel in a subject using a device taught herein, the method comprising:
creating a point of entry in a vascular lumen of the subject;
inserting the device into the vascular lumen;
cutting tissue from the vascular lumen with the cutting head of the device;
and,
removing the device from the vascular lumen of the subject.

In some embodiments, the teachings are directed to a method of performing a thrombectomy in a subject using a thrombectomy device taught herein, the method comprising:
creating a point of entry in a vascular lumen of the subject;
inserting the thrombectomy device into the vascular lumen;
cutting thrombus tissue from the vascular lumen with the cutting head of the thrombectomy device;
and,
removing the thrombectomy device from the vascular lumen of the subject.

In some embodiments, the teachings are directed to a method of performing a atherectomy in a subject using a device taught herein, the method comprising:

creating a point of entry in a vascular lumen of the subject;
inserting the device into the vascular lumen;
cutting tissue from the vascular lumen with the cutting head of the device;
and,
removing the device from the vascular lumen of the subject.

In some embodiments, the methods further include inserting a guidewire in the point of entry and delivering the guidewire to a target location in the vascular lumen of a subject, and guiding the device to the target location on the guidewire.

In some embodiments, the methods further include discharging excised tissue from the vascular lumen with a vacuum.

The devices taught herein include several methods of removing a vascular lesion from within a subject. In fact the lesion can be removed from any blood vessel. In some embodiments, the methods can include creating a point of entry in a vascular lumen of the subject; inserting a thrombectomy device taught herein into the vascular lumen; telescoping the flexible rotating shaft; cutting a thrombus from a wall of a vascular lumen with the cutter of the device; discharging the cut tissue from the vascular lumen which in some embodiments can be facilitated with a vacuum pump; and, removing the device from the vascular lumen of the subject.

In some embodiments, the method of removing a thrombus can include obtaining a thrombectomy device taught herein, creating an opening into the vasculature of a subject having a thrombus, inserting the device in the vasculature of the subject, moving the distal end of the thrombectomy device to the site of the thrombus, removing the thrombus from the subject with the thrombectomy device, and removing the thrombectomy device from the subject.

In some embodiments, the method includes
inserting a device taught herein into a vascular lumen of a subject, the device having a
a flexible rotating shaft with a proximal end, a distal end, and a lumen;
a cutting head in the shape of, for example, a tubular cutter at the distal end of the flexible rotating shaft, the cutting head having a proximal end, and a distal end, the cutting head and configured with
(i) an open mouth that communicates with the lumen of the rotating shaft, the open mouth having (i) an inlet defined by an asymmetric cutting tip on the mouth, the asymmetric cutting tip having a second longitudinal plane bisecting the cutting tip; and (ii) an outlet in communication with the lumen of the rotating shaft; wherein, the second longitudinal plane is not coincident with the first longitudinal plane to provide the asymmetric cutting tip;
(ii) a vacuum port configured for operable communication with vacuum source;
a distal end, a proximal end, a long axis, and a guidewire lumen passing through the device in the direction of the long axis;
advancing the cutter to a target area in the vascular lumen of the subject, the advancing including
cutting vascular tissue from the wall of the vascular lumen, the cutting including rotating the cutter; and,
removing the vascular tissue from the vascular lumen using the positive displacement pump; and,
removing the thrombectomy device from the subject.

Figure 11:
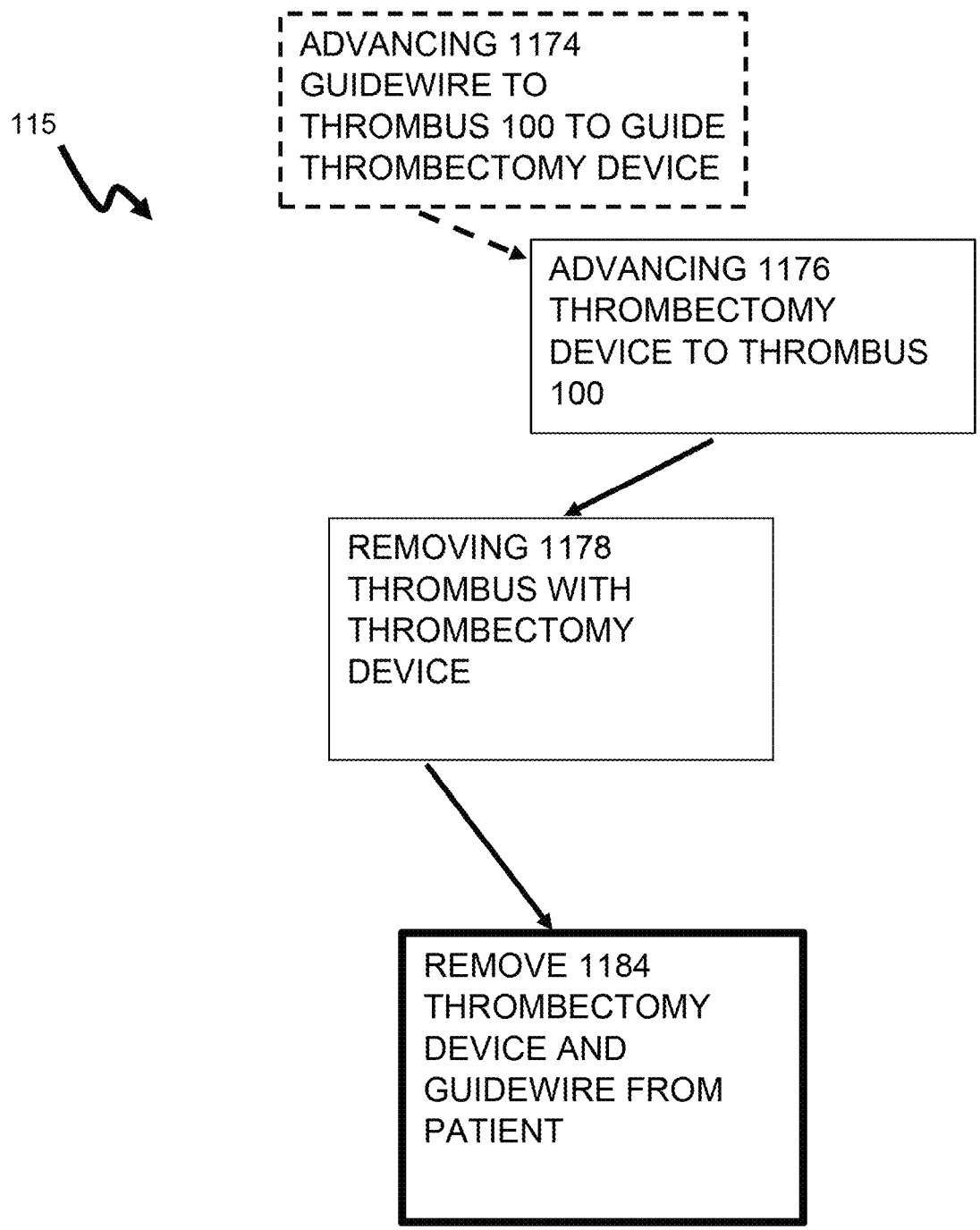
FIG. 11 is a flowchart of a thrombectomy method, according to some embodiments.

FIG. 11 is a flowchart of a thrombectomy method, according to some embodiments. Method 1150 can be used with the thrombectomy devices taught herein to remove a thrombus from a blood vessel. A guidewire is advanced 1174 through a guiding catheter and across a thrombus in the blood vessel in a target area. Once the guidewire is in place at the target area, the thrombectomy device is advanced 1176 to the thrombus on the guidewire. The thrombectomy device is then in proper position to cut and remove 1178 the thrombus in the target area. To complete the procedure, the thrombectomy device and guidewire are removed 1182 from the patient. The dashed line around the guidewire advancing step 1174 shows that the guidewire is optional. As such, in some embodiments, the use of a guidewire is not necessary.

I claim:
1. A thrombectomy device, comprising
a flexible rotating shaft with a proximal end, a distal end, and a lumen;
a curved, tubular cutter operably connected to the distal end of the flexible rotating shaft, the tubular cutter including a head with an axis and a mouth having a z-axis, a neck connected to the head and having an axis of rotation, and an angle, θz, ranging from 90° to 135°, between the z-axis of the mouth and the axis of rotation, the mouth configured with
a leading edge having a highest height, h-leading;
a trailing edge having a lowest height, h-trailing;
a vertical bias ratio of h-leading/h-trailing ranging from 1.05 to 2.0;
a distance, $B_L$, between the axis of rotation and the leading edge;
a distance, $B_T$, between the axis of rotation and the trailing edge; and,
a lateral bias ratio of $B_L/B_T$ ranging from 1.05 to 2.0;
and,
a vacuum port configured for operable communication with a vacuum source to facilitate transport of the tissue out of the subject.

2. The device of claim 1, wherein the cutter is deflected from the axis of rotation to create a deflection distance between the leading edge of the cutter and the axis of rotation.

3. The device of claim 1, wherein the axis of the head is at a vertical angle, ϕ, with the axis of rotation, wherein ϕ ranges from 0° to 90° to create a deflection distance between the leading edge of the cutter and the axis of rotation.

4. The device of claim 1, wherein the axis of the head is at a lateral angle, θo, with the axis of rotation, wherein θo ranges from 0° to 90° to create a deflection distance between the leading edge of the cutter and the axis of rotation.

5. The device of claim 1, wherein the flexible rotating shaft is deflected at an angle, θm, with the axis of rotation to form a curve region in the flexible rotating shaft, wherein θm ranges from 0-90 degrees to create a deflection distance between the leading edge of the cutter and the axis of rotation.

6. The device of claim 5, wherein the z-axis of the mouth is at an angle, θr, from a plane containing the curve region to open the mouth toward the target site for the tissue for removal.

7. The device of claim 5, further comprising a straightening sheath.

8. A system comprising the device of claim 5, the system further comprising a handle that includes a motor operably connected to a drive assembly that includes the flexible rotating shaft and the cutter, the motor configured to provide a rotational movement to the flexible, rotating shaft for rotating the cutter.

9. The system of claim 8, wherein the z-axis of the mouth is an angle, θr, from a plane containing the curve region to open the mouth toward the target site for the tissue for removal.

10. The system of claim 5, further comprising a straightening sheath.

11. A system comprising the device of claim 5, further comprising a vacuum source; wherein the vacuum port is in operable connection with the vacuum source for removal of the tissue from the system.

12. The device of claim 1, wherein the mouth has a cross-sectional area that is equal to, or less than, the lumen of the flexible, rotating shaft.

13. A system comprising the device of claim 1, the system further comprising a handle that includes a motor operably connected to a drive assembly that includes the flexible rotating shaft and the cutter, the motor configured to provide a rotational movement to the flexible, rotating shaft for rotating the cutter.

14. A system comprising the device of claim 1, further comprising a vacuum source, and wherein the vacuum port is in operable connection with the vacuum source for removal of the tissue from the system.

15. A method of performing a thrombectomy using the device of claim 1, the method comprising:
creating a point of entry in a vascular lumen of the subject;
inserting the thrombectomy device into the vascular lumen;
delivering the cutter to the target site having the tissue for removal;
cutting the tissue from the vascular lumen with the cutter; and,
removing the thrombectomy device from the vascular lumen of the subject.

16. The method of claim 15, the method further comprising inserting a guidewire in the point of entry and delivering the guidewire to the target location of the thrombus, and guiding the thrombectomy device to the location of the thrombus on the guidewire.

17. The method of claim 15, the method further comprising discharging the tissue from the vascular lumen with a vacuum.

18. A method of performing a thrombectomy in a subject using the device of claim 5, and the method comprises:
creating a point of entry in a vascular lumen of the subject;
inserting the thrombectomy device into the vascular lumen;
delivering the cutter to the target site having the tissue for removal;
cutting tissue from the vascular lumen with the cutter; and,
removing the thrombectomy device from the vascular lumen of the subject.

19. The method of claim 18, the method further comprising inserting a guidewire in the point of entry and delivering the guidewire to the target location of the tissue, and guiding the cutter to the location of the thrombus on the guidewire.

20. The method of claim 18, the method further comprising discharging the tissue from the vascular lumen with a vacuum.

* * * * *